(12) United States Patent
Scheller et al.

(10) Patent No.: US 9,693,906 B2
(45) Date of Patent: *Jul. 4, 2017

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/805,520

(22) Filed: Jul. 22, 2015

(65) Prior Publication Data

US 2016/0045366 A1 Feb. 18, 2016

Related U.S. Application Data

(63) Continuation of application No. 14/461,926, filed on Aug. 18, 2014, now Pat. No. 9,119,702.

(51) Int. Cl.
*A61B 18/18* (2006.01)
*A61F 9/008* (2006.01)
*A61B 18/22* (2006.01)
*A61B 34/00* (2016.01)
*A61B 18/00* (2006.01)

(52) U.S. Cl.
CPC .......... *A61F 9/00823* (2013.01); *A61B 18/22* (2013.01); *A61B 34/71* (2016.02); *A61F 9/008* (2013.01); *A61B 2018/00964* (2013.01); *A61B 2018/225* (2013.01); *A61B 2018/2238* (2013.01); *A61F 9/00821* (2013.01); *A61F 2009/00872* (2013.01)

(58) Field of Classification Search
CPC ....... A61F 9/00823; A61F 9/008; A61B 34/71
USPC .......................................................... 606/4
See application file for complete search history.

(56) References Cited

U.S. PATENT DOCUMENTS

| 5,190,050 A | 3/1993 | Nitzsche |
| 5,322,055 A * | 6/1994 | Davison ......... A61B 17/320068 601/2 |

(Continued)

FOREIGN PATENT DOCUMENTS

| EP | EP 0900547 B1 | 3/1999 |
| NL | WO 2013/133717 | 9/2013 |
| WO | WO 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include a handle, an actuation structure of the handle, a housing tube, a flexible tube, an optic fiber, and a wire having a pre-formed curve. The flexible tube may be disposed within the housing tube wherein a distal end of the flexible tube projects out from a distal end of the housing tube. The optic fiber may be disposed within an inner bore of the handle, the housing tube, and the flexible tube. The wire may be disposed within the housing tube.

20 Claims, 36 Drawing Sheets

(56) References Cited

U.S. PATENT DOCUMENTS

| | | |
|---|---|---|
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,855,577 A | 1/1999 | Murphy-Chutorian et al. |
| 6,123,699 A | 9/2000 | Webster, Jr. |
| 6,126,654 A | 10/2000 | Giba et al. |
| 6,198,974 B1 | 3/2001 | Webster, Jr. |
| 6,488,695 B1 | 12/2002 | Hickingbotham |
| 6,505,530 B2 | 1/2003 | Adler et al. |
| 6,530,913 B1 | 3/2003 | Giba et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 8/2010 | Mc Gowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,951,245 B2 | 2/2015 | Scheller et al. |
| 8,968,277 B2 | 3/2015 | Scheller et al. |
| 9,023,019 B2 | 5/2015 | Scheller et al. |
| 9,023,020 B2 | 5/2015 | Scheller et al. |
| 2003/0171762 A1* | 9/2003 | Forchette ............ A61B 17/2909 606/139 |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0157985 A1 | 7/2005 | McGowan, Sr. et al. |
| 2005/0272975 A1 | 12/2005 | McWeeny et al. |
| 2005/0277874 A1 | 12/2005 | Selkee |
| 2007/0185514 A1 | 8/2007 | Kirchhevel |
| 2009/0018393 A1 | 1/2009 | Dick et al. |
| 2009/0187170 A1 | 7/2009 | Auld et al. |
| 2009/0312750 A1 | 12/2009 | Spaide |
| 2010/0004642 A1* | 1/2010 | Lumpkin ............... A61B 18/22 606/4 |
| 2010/0268234 A1 | 10/2010 | Aho et al. |
| 2011/0028947 A1 | 2/2011 | Scheller et al. |
| 2012/0116361 A1 | 5/2012 | Hanlon et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |

* cited by examiner

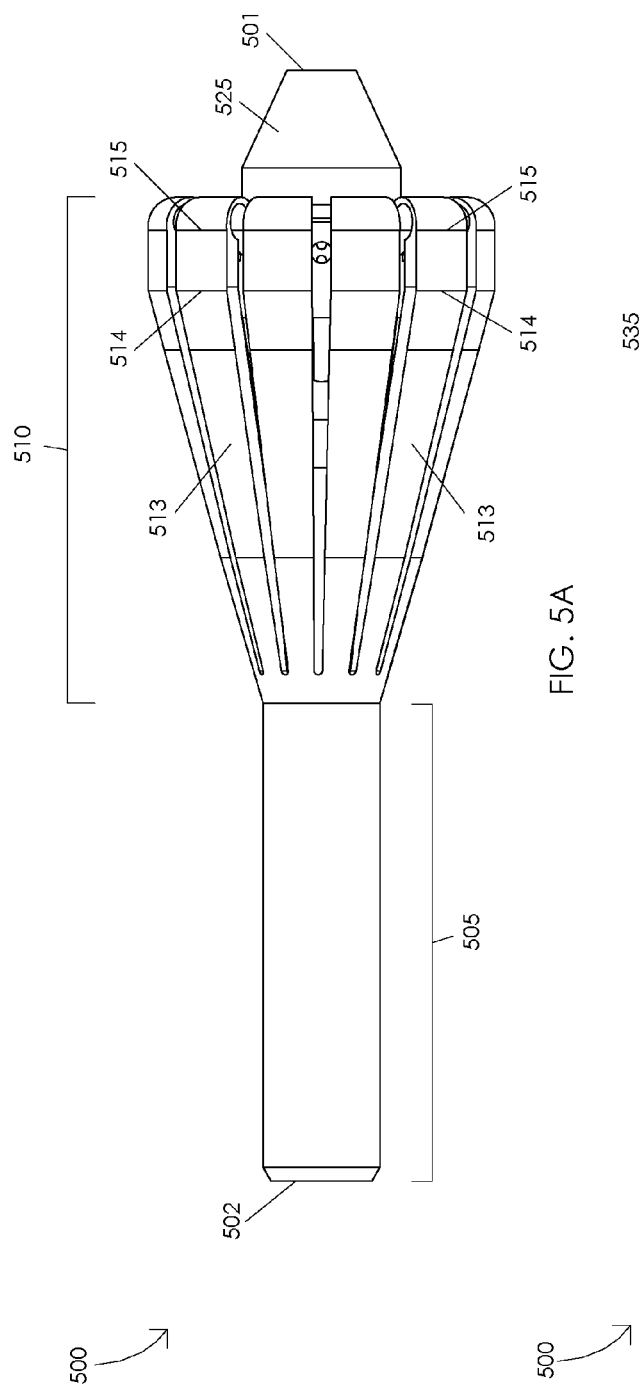
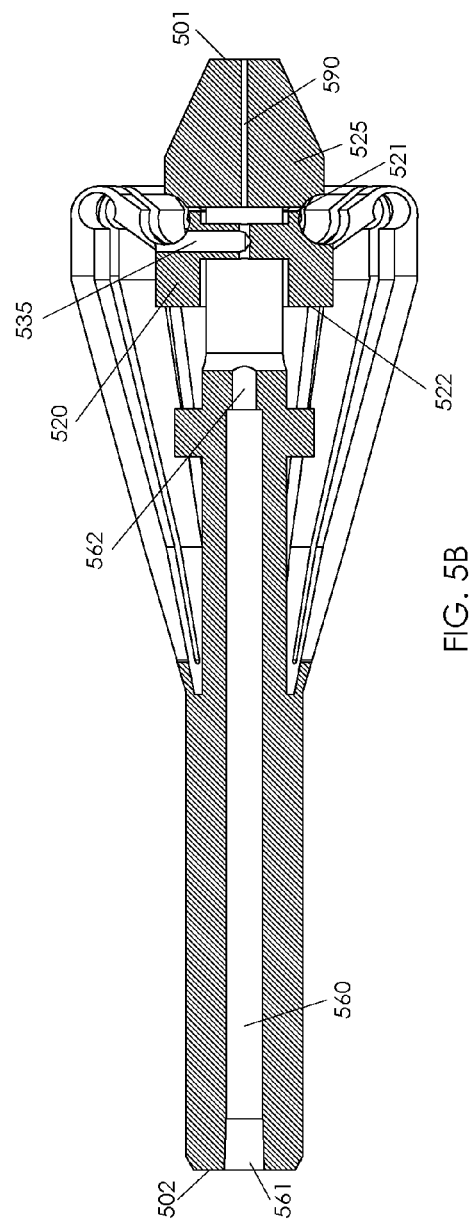
FIG. 5A
FIG. 5B

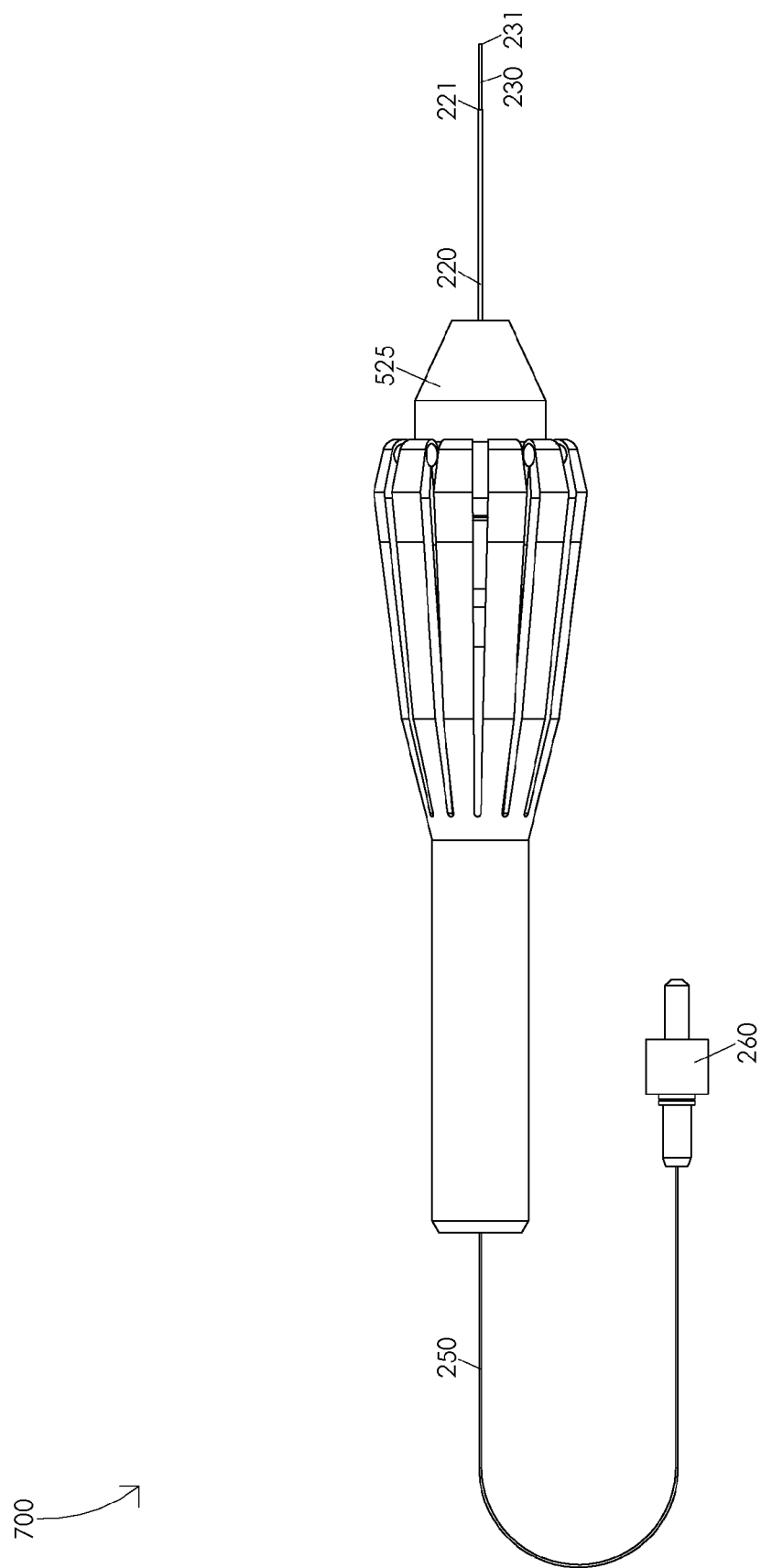

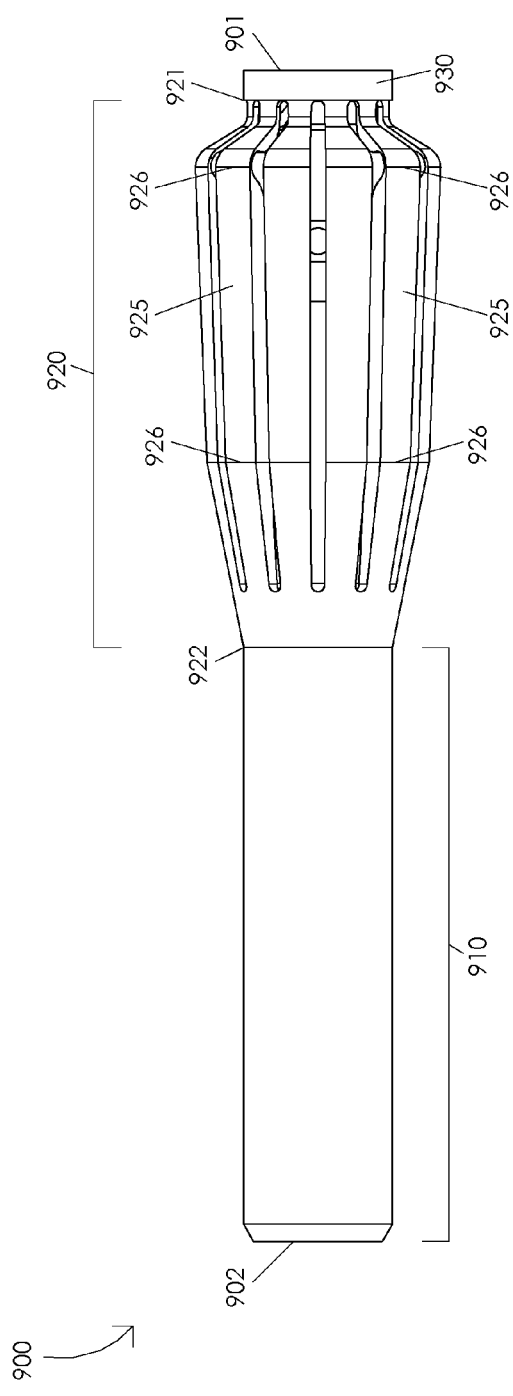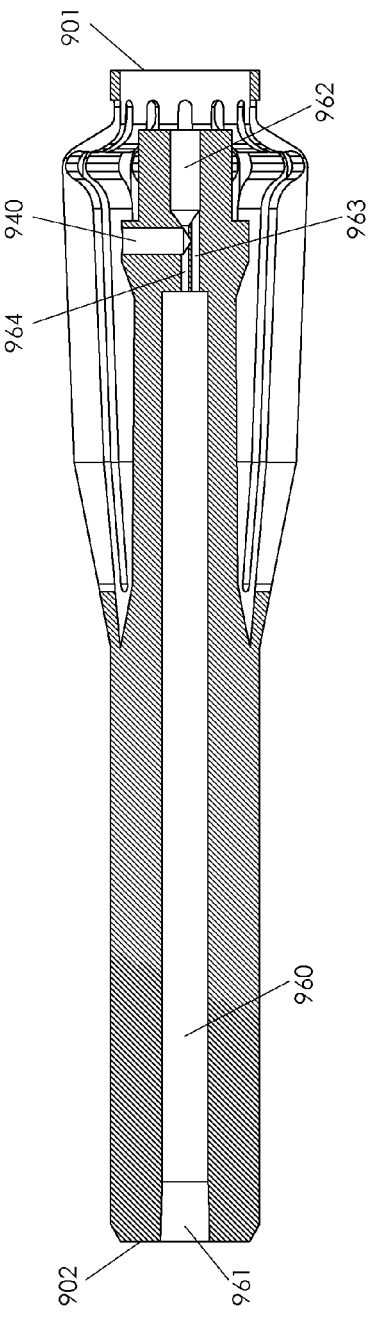
FIG. 9A
FIG. 9B

STEERABLE LASER PROBE

CROSS-REFERENCE TO RELATED APPLICATIONS

This Application is a continuation of prior application Ser. No. 14/461,926, filed Aug. 18, 2014.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle, an actuation structure of the handle, a housing tube, a flexible tube, an optic fiber, and a wire having a pre-formed curve. Illustratively, the flexible tube may be disposed within the housing tube wherein a distal end of the flexible tube projects out from a distal end of the housing tube. In one or more embodiments, the optic fiber may be disposed within an inner bore of the handle, the housing tube, and the flexible tube. Illustratively, the wire may be disposed within the housing tube.

In one or more embodiments, a compression of the actuation structure may be configured to curve the optic fiber. Illustratively, a compression of the actuation structure may be configured to extend the wire relative to the housing tube wherein a portion of the pre-formed curve may be extended into a portion of the flexible tube projecting out from the distal end of the housing tube. In one or more embodiments, an extension of a portion of the pre-formed curve into the portion of the flexible tube projecting out from the distal end of the housing tube may be configured to gradually curve the flexible tube. Illustratively, a gradual curving of the flexible tube may be configured to gradually curve the optic fiber.

In one or more embodiments, a decompression of the actuation structure may be configured to straighten the optic fiber. Illustratively, a decompression of the actuation structure may be configured to retract the wire relative to the housing tube wherein a portion of the pre-formed curve may be retracted out of a portion of the flexible tube projecting out from the distal end of the housing tube. In one or more embodiments, a retraction of a portion of the pre-formed curve out of the portion of the flexible tube projecting out from the distal end of the housing tube may be configured to gradually straighten the flexible tube. Illustratively, a gradual straightening of the flexible tube may be configured to gradually curve the optic fiber.

In one or more embodiments, a decompression of the actuation structure may be configured to curve the optic fiber. Illustratively, a decompression of the actuation structure may be configured to extend the wire relative to the housing tube wherein a portion of the pre-formed curve may be extended into a portion of the flexible tube projecting out from the distal end of the housing tube. In one or more embodiments, an extension of a portion of the pre-formed curve into the portion of the flexible tube projecting out from the distal end of the housing tube may be configured to gradually curve the flexible tube. Illustratively, a gradual curving of the flexible tube may be configured to gradually curve the optic fiber.

In one or more embodiments, a compression of the actuation structure may be configured to straighten the optic fiber. Illustratively, a compression of the actuation structure may be configured to retract the wire relative to the housing tube wherein a portion of the pre-formed curve may be retracted out of a portion of the flexible tube projecting out from the distal end of the housing tube. In one or more embodiments, a retraction of a portion of the pre-formed curve out of the portion of the flexible tube projecting out from the distal end of the housing tube may be configured to gradually straighten the flexible tube. Illustratively, a gradual straightening of the flexible tube may be configured to gradually curve the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 5A and 5B are schematic diagrams illustrating a handle;

FIGS. 7A, 7B, 7C, 7D, and 7E illustrate a gradual curving of an optic fiber;

FIGS. 9A and 9B are schematic diagrams illustrating a handle;

DETAILED DESCRIPTION OF AN ILLUSTRATIVE EMBODIMENT

Figure 1A:
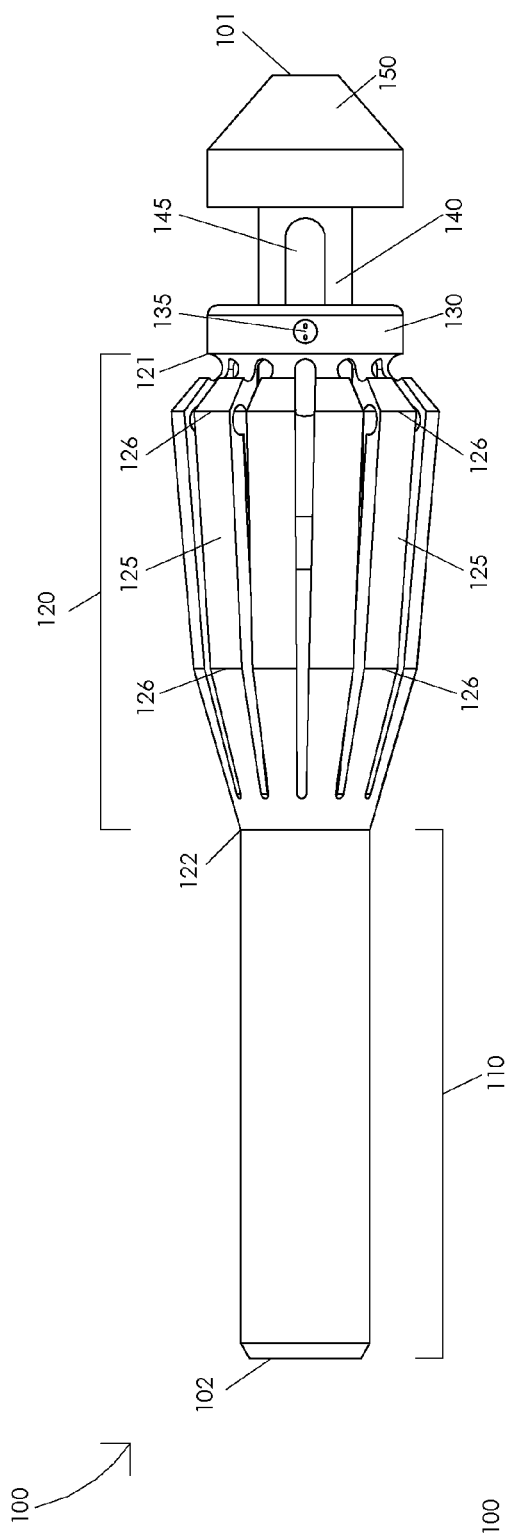
FIGS. 1A and 1B are schematic diagrams illustrating a handle.
Figure 1B:
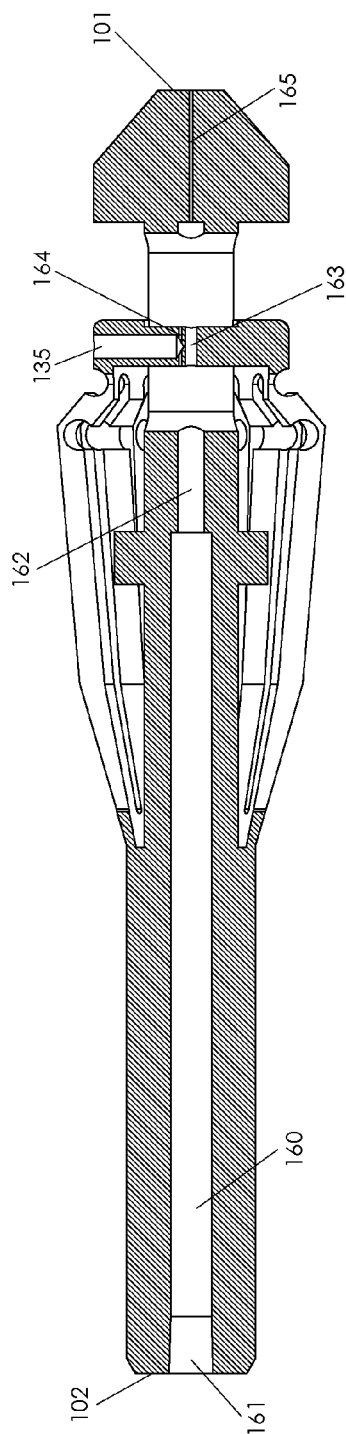

FIGS. 1A and 1B are schematic diagrams illustrating a handle 100. FIG. 1A illustrates a top view of handle 100. In one or more embodiments, handle 100 may comprise a handle distal end 101, a handle proximal end 102, a handle base 110, an actuation structure 120, an actuation ring 130, an actuation mechanism housing 135, a platform base 140, an actuation mechanism guide 145, and a housing tube platform 150. Illustratively, actuation structure 120 may comprise an actuation structure distal end 121 and an actuation structure proximal end 122. In one or more embodiments, actuation structure 120 may comprise a plurality of actuation arms 125. Illustratively, each actuation arm 125 may comprise at least one extension mechanism 126. In one or more embodiments, actuation structure 120 may comprise a shape memory material configured to project actuation structure distal end 121 a first distance from actuation structure proximal end 122, e.g., when actuation structure 120 is fully decompressed. Illustratively, actuation structure 120 may comprise a shape memory material configured to project actuation structure distal end 121 a second distance from actuation structure proximal end 122, e.g., when actuation structure 120 is fully compressed. In one or more embodiments, the second distance from actuation structure proximal end 122 may be greater than the first distance from actuation structure proximal end 122. Actuation structure 120 may be manufactured from any suitable material, e.g., polymers, metals, metal alloys, etc., or from any combination of suitable materials.

Illustratively, actuation structure 120 may be compressed by an application of a compressive force to actuation structure 120. In one or more embodiments, actuation structure 120 may be compressed by an application of one or more compressive forces located at one or more locations around an outer perimeter of actuation structure 120. Illustratively, the one or more locations may comprise any of a plurality of locations around the outer perimeter of actuation structure 120. For example, a surgeon may compress actuation structure 120, e.g., by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 from any rotational position of a plurality of rotational positions of handle 100.

In one or more embodiments, actuation structure 120 may be compressed by an application of a compressive force to any one or more of the plurality of actuation arms 125. Illustratively, each actuation arm 125 may be configured to actuate independently. In one or more embodiments, each actuation arm 125 may be connected to one or more of the plurality of actuation arms 125 wherein an actuation of a particular actuation arm 125 may be configured to actuate every actuation arm 125 of the plurality of actuation arms 125. Illustratively, one or more actuation arms 125 may be configured to actuate in pairs or groups. For example, an actuation of a first actuation arm 125 may be configured to actuate a second actuation arm 125.

In one or more embodiments, a compression of actuation structure 120, e.g., due to an application of a compressive force to a particular actuation arm 125, may be configured to actuate the particular actuation arm 125. Illustratively, an actuation of the particular actuation arm 125 may be configured to actuate every actuation arm 125 of the plurality of actuation arms 125. In one or more embodiments, an application of a compressive force to a particular actuation arm 125 may be configured to extend at least one extension mechanism 126 of the particular actuation arm 125. Illustratively, a particular actuation arm 125 may be configured to extend a first length from handle base 110. In one or more embodiments, an extension of an extension mechanism 126 of the particular actuation arm 125, e.g., due to an application of a compressive force to the particular actuation arm 125, may be configured to extend the particular actuation arm 125 a second length from handle base 110. Illustratively, the second length from handle base 110 may be greater than the first length from handle base 110.

In one or more embodiments, actuation ring 130 may be fixed to actuation structure distal end 121. Illustratively, a compression of actuation structure 120 may be configured to gradually extend actuation ring 130 from handle base 110. For example, actuation ring 130 may be configured to extend a first distance from actuation structure proximal end 122, e.g., when actuation structure 120 is fully decompressed. In one or more embodiments, actuation ring 130 may be configured to extend a second distance from actuation structure proximal end 122, e.g., due to a compression of actuation structure 120. Illustratively, the second distance from actuation structure proximal end 122 may be greater than the first distance from actuation structure proximal end 122.

FIG. 1B illustrates a cross-sectional view of handle 100. In one or more embodiments, handle 100 may comprise an inner bore 160, an inner bore proximal taper 161, an inner bore distal chamber 162, an optic fiber guide 163, a wire proximal end housing 164, and a wire guide 165. Handle 100 may be manufactured from any suitable material, e.g., polymers, metals, metal alloys, etc., or from any combination of suitable materials.

Figure 2:
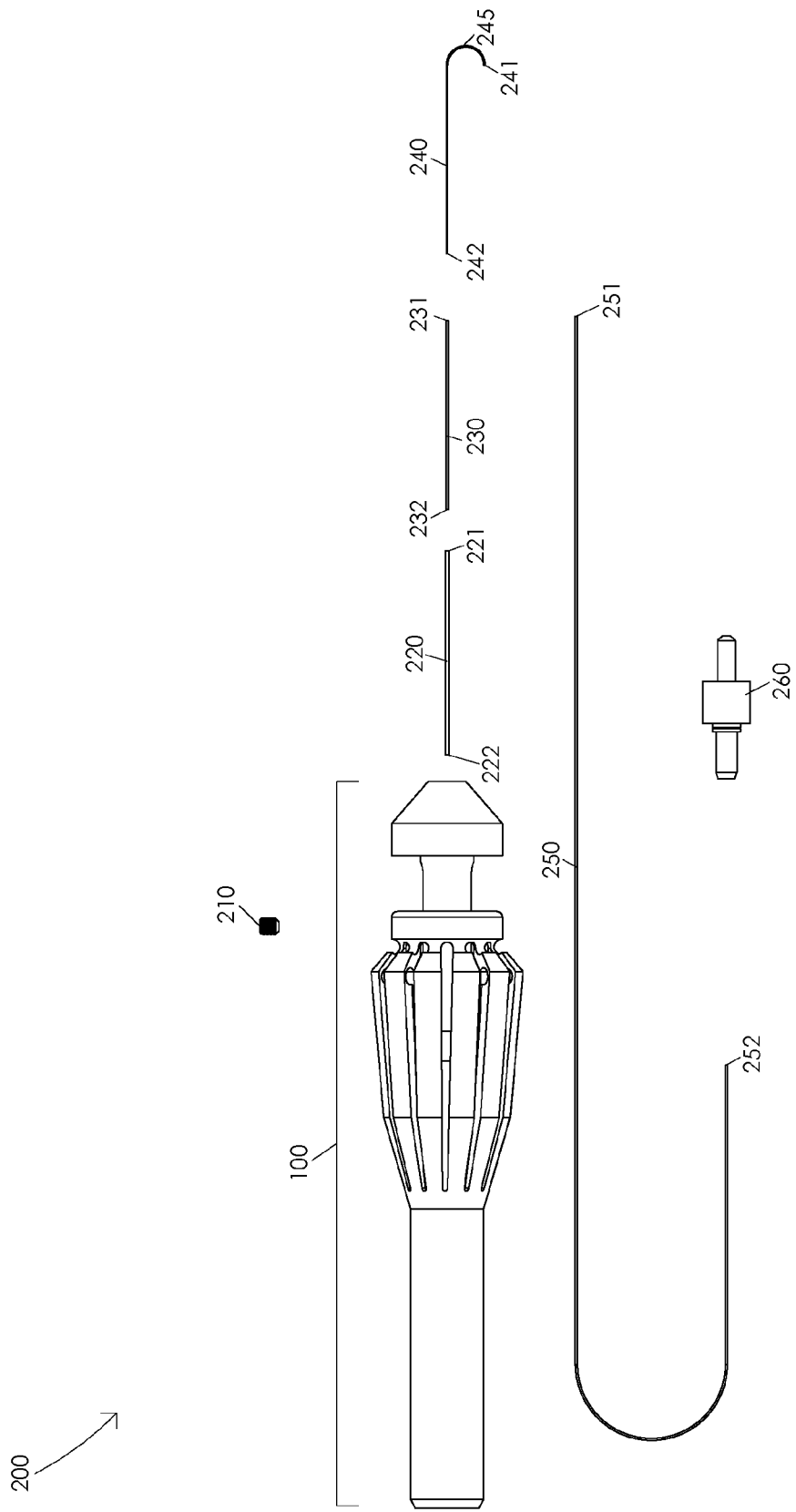
FIG. 2 is a schematic diagram illustrating an exploded view of a steerable laser probe assembly.

FIG. 2 is a schematic diagram illustrating an exploded view of a steerable laser probe assembly 200. In one or more embodiments, steerable laser probe assembly 200 may comprise a handle 100; an actuation mechanism 210; a housing tube 220 having a housing tube distal end 221 and a housing tube proximal end 222; a flexible tube 230 having a flexible tube distal end 231 and a flexible tube proximal end 232; a wire 240 having a wire distal end 241, a wire proximal end 242, and a pre-formed curve 245; an optic fiber 250 having an optic fiber distal end 251 and an optic fiber proximal end 252; and a light source interface 260. Illustratively, light source interface 260 may be configured to interface with optic fiber 250, e.g., at optic fiber proximal end 252. In one or more embodiments, light source interface 260 may comprise a standard light source connector, e.g., an SMA connector.

Illustratively, housing tube 220 may be fixed to housing tube platform 150, e.g., housing tube proximal end 222 may be fixed to handle distal end 101. In one or more embodiments, housing tube 220 may be fixed to housing tube platform 150, e.g., by an adhesive or by any other suitable fixation means. Illustratively, a portion of housing tube 220 may be disposed within wire guide 165, e.g., housing tube proximal end 222 may be disposed within wire guide 165. In one or more embodiments, a portion of housing tube 220 may be fixed within wire guide 165, e.g., by an adhesive or other any suitable fixation means. Housing tube 220 may be manufactured from any suitable material, e.g., polymers, metals, metal alloys, etc., or from any combination of suitable materials.

In one or more embodiments, a portion of flexible tube 230 may be disposed within housing tube 220, e.g., flexible tube proximal end 232 may be disposed within housing tube 220. Illustratively, a portion of flexible tube 230 may extend from housing tube 220, e.g., flexible tube distal end 231 may extend from housing tube distal end 221. In one or more embodiments, a portion of flexible tube 230 may be fixed within housing tube 220, e.g., by an adhesive or any other suitable fixation means. Illustratively, a portion of flexible tube 230 may be disposed within a portion of housing tube 220. In one or more embodiments, a portion of flexible tube 230 may be disposed within wire guide 165, e.g., flexible tube proximal end 232 may be disposed within wire guide 165. Illustratively, a portion of flexible tube 230 may be fixed within wire guide 165, e.g., by an adhesive or any other suitable fixation means. In one or more embodiments, a portion of flexible tube 230 may be fixed to housing tube platform 150, e.g., by an adhesive or any other suitable fixation means. Flexible tube 230 may be manufactured from any suitable material, e.g., polymers, metals, metal alloys, etc., or from any combination of suitable materials.

Illustratively, optic fiber 250 may be disposed within inner bore 160, inner bore distal chamber 162, optic fiber guide 163, wire guide 165, housing tube 220, and flexible tube 230. In one or more embodiments, optic fiber 250 may be disposed within flexible tube 230 wherein optic fiber distal end 251 may be adjacent to flexible tube distal end 231. Illustratively, a portion of optic fiber 250 may be fixed to an inner portion of flexible tube 230, e.g., by an adhesive or any other suitable fixation means. In one or more embodiments, a portion of optic fiber 250 may be fixed to an inner portion of housing tube 220, e.g., by an adhesive or any other suitable fixation means. Illustratively, optic fiber 250 may be configured to transmit light, e.g., light from a light source.

In one or more embodiments, a portion of wire 240 may comprise a shape memory material, e.g., Nitinol. Illustratively, pre-formed curve 245 may comprise a shape memory material, e.g., Nitinol. In one or more embodiments, wire 240 may be disposed within wire proximal end housing 164, wire guide 165, and housing tube 220. Illustratively, a portion of wire 240 may be disposed within flexible tube 230. In one or more embodiments, actuation mechanism 210 may be housed within actuation mechanism housing 135. Illustratively, actuation mechanism 210 may be configured to fix a portion of wire 240, e.g., wire proximal end 242, in a position relative to actuation ring 130. In one or more embodiments, actuation mechanism 210 may comprise a set screw configured to fix wire 240 in a position relative to actuation ring 130, e.g., by a press fit or any other suitable fixation means. Illustratively, a portion of wire 240, e.g., wire proximal end 242, may be fixed to actuation mechanism 210, e.g., by an adhesive or any other suitable fixation means. Wire 240 may be manufactured from any suitable material, e.g., polymers, metals, metal alloys, etc., or from any combination of suitable materials.

In one or more embodiments, a compression of actuation structure 120 may be configured to extend actuation ring 130 relative to handle base 110. Illustratively, a compression of actuation structure 120 may be configured to actuate actuation ring 130 away from handle proximal end 102 and towards housing tube platform 150. In one or more embodiments, a compression of actuation structure 120 may be configured to extend actuation mechanism 210 relative to handle base 110. Illustratively, a compression of actuation structure 120 may be configured to actuate actuation mechanism 210, e.g., within actuation mechanism guide 145, away from handle proximal end 102 and towards housing tube platform 150.

In one or more embodiments, an extension of actuation mechanism 210 relative to handle base 110, e.g., due to a compression of actuation structure 120, may be configured to extend wire 240 relative to housing tube 220. Illustratively, if wire 240 is disposed within housing tube 220 wherein pre-formed curve 245 is contained within housing tube 220, then pre-formed curve 245 may be generally straightened, e.g., by housing tube 220. In one or more embodiments, an extension of wire 240 relative to housing tube 220 may be configured to extend pre-formed curve 245 into a portion of flexible tube 230, e.g., a portion of flexible tube 230 extending from housing tube distal end 221. Illustratively, an extension of pre-formed curve 245 into a portion of flexible tube 230, e.g., a portion of flexible tube 230 extending from housing tube distal end 221, may be configured to curve flexible tube 230. In one or more embodiments, a curving of flexible tube 230 may be configured to curve optic fiber 250.

In one or more embodiments, a decompression of actuation structure 120 may be configured to retract actuation ring 130 relative to handle base 110. Illustratively, a decompression of actuation structure 120 may be configured to actuate actuation ring 130 towards handle proximal end 102 and away from housing tube platform 150. In one or more embodiments, a decompression of actuation structure 120 may be configured to retract actuation mechanism 210 relative to handle base 110. Illustratively, a decompression of actuation structure 120 may be configured to actuate actuation mechanism 210, e.g., within actuation mechanism guide 145, towards handle proximal end 102 and away from housing tube platform 150.

In one or more embodiments, a retraction of actuation mechanism 210 relative to handle base 110, e.g., due to a decompression of actuation structure 120, may be configured to retract wire 240 relative to housing tube 220. Illustratively, if wire 240 is discs posed within flexible tube 230 wherein a portion of pre-formed curve 245 is contained within flexible tube 230, then a portion of pre-formed curve 245 may be generally curved, e.g., causing flexible tube 230 to be curved. In one or more embodiments, a retraction of wire 240 relative to housing tube 220 may be configured to retract pre-formed curve 245 into a portion of housing tube, e.g., causing pre-formed curve 245 to be retracted out of a potion of flexible tube 230 extending from housing tube distal end 221. Illustratively, a retraction of pre-formed curve 245 out of a portion of flexible tube 230, e.g., a portion of flexible tube 230 extending from housing tube distal end 221, may be configured to straighten flexible tube 230. In one or more embodiments, a straightening of flexible tube 230 may be configured to straighten optic fiber 250.

Figure 3A:
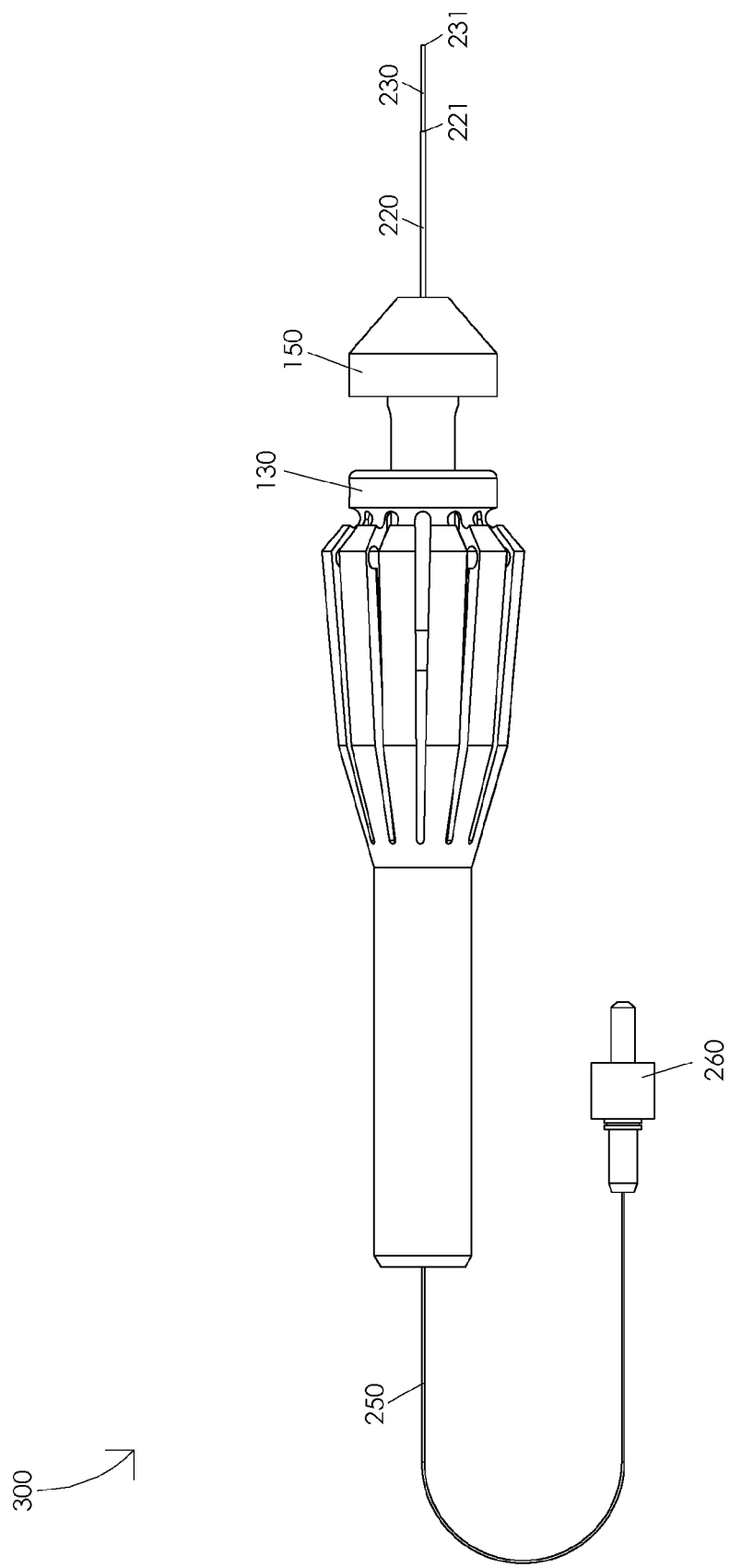
FIGS. 3A, 3B, 3C, 3D, and 3E illustrate a gradual curving of an optic fiber.

FIGS. 3A, 3B, 3C, 3D, and 3E illustrate a gradual curving of an optic fiber 250. FIG. 3A illustrates a straight optic fiber 300. In one or more embodiments, optic fiber 250 may comprise a straight optic fiber 300, e.g., when actuation ring 130 is fully retracted relative to handle base 110. Illustratively, optic fiber 250 may comprise a straight optic fiber 300, e.g., when actuation structure 120 is fully decompressed. In one or more embodiments, optic fiber 250 may comprise a straight optic fiber 300, e.g., when wire 240 is fully retracted relative to housing tube 220. For example, optic fiber 250 may comprise a straight optic fiber 300 when pre-formed curve 245 is fully contained within housing tube 220. Illustratively, a line tangent to optic fiber distal end 251 may be parallel to a line tangent to housing tube proximal end 202, e.g., when optic fiber 250 comprises a straight optic fiber 300.

Figure 3B:
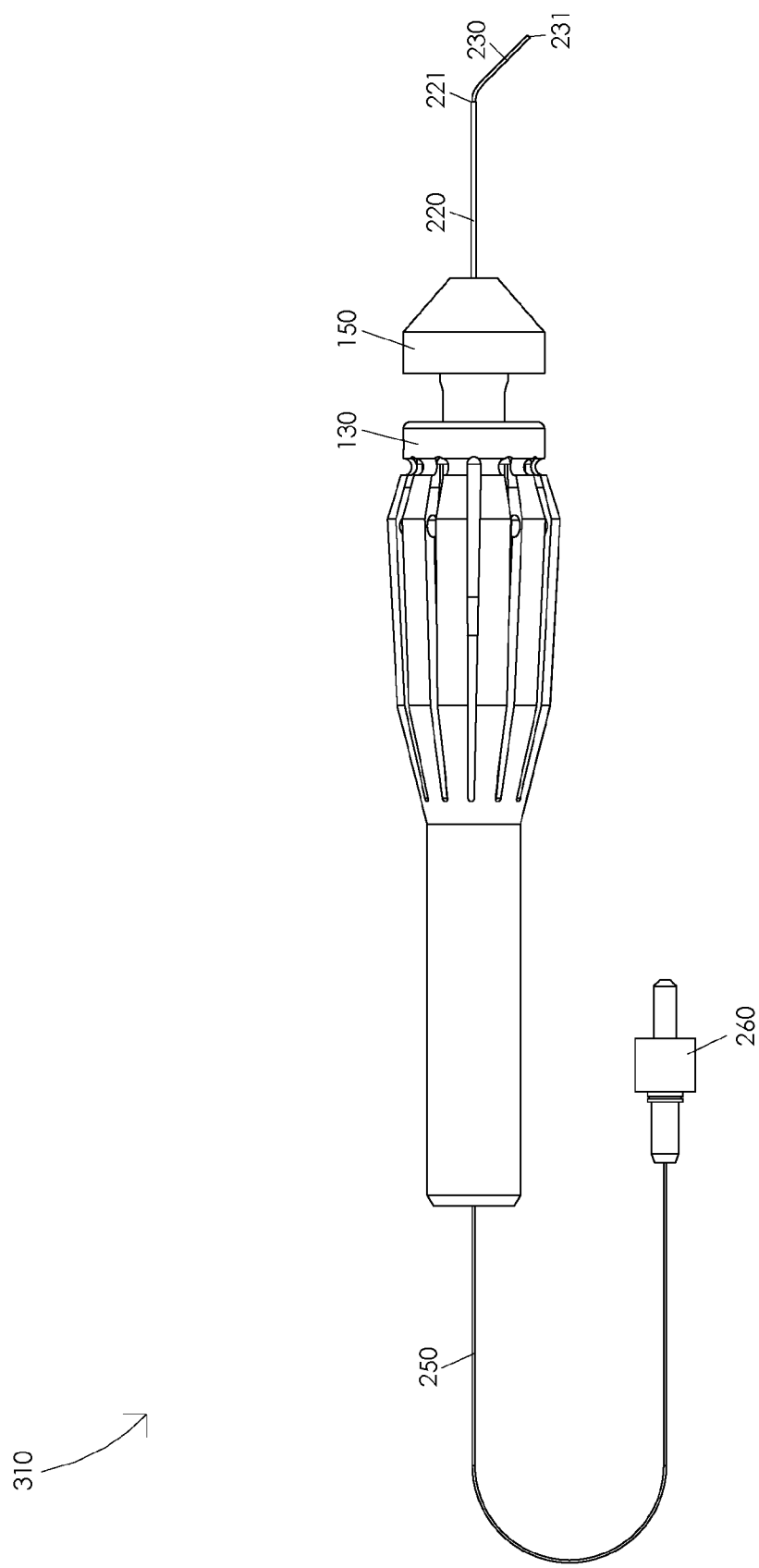

FIG. 3B illustrates an optic fiber in a first curved position 310. In one or more embodiments, a compression of actuation structure 120 may be configured to gradually curve optic fiber 250 from a straight optic fiber 300 to an optic fiber in a first curved position 310. Illustratively, a compression of actuation structure 120 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a compression of actuation structure 120, may be configured to cause wire 240 to gradually curve flexible tube 230. In one or more embodiments, a gradual curving of flexible tube 230 may be configured to gradually curve optic fiber 250, e.g., from a straight optic fiber 300 to an optic fiber in a first curved position 310. Illustratively, a line tangent to optic fiber distal end 251 may intersect a line tangent to housing tube proximal end 202 at a first angle, e.g., when optic fiber 250 comprises an optic fiber in a first curved position 310. In one or more embodiments, the first angle may comprise any angle greater than zero degrees. For example, the first angle may comprise a 45 degree angle.

Figure 3C:
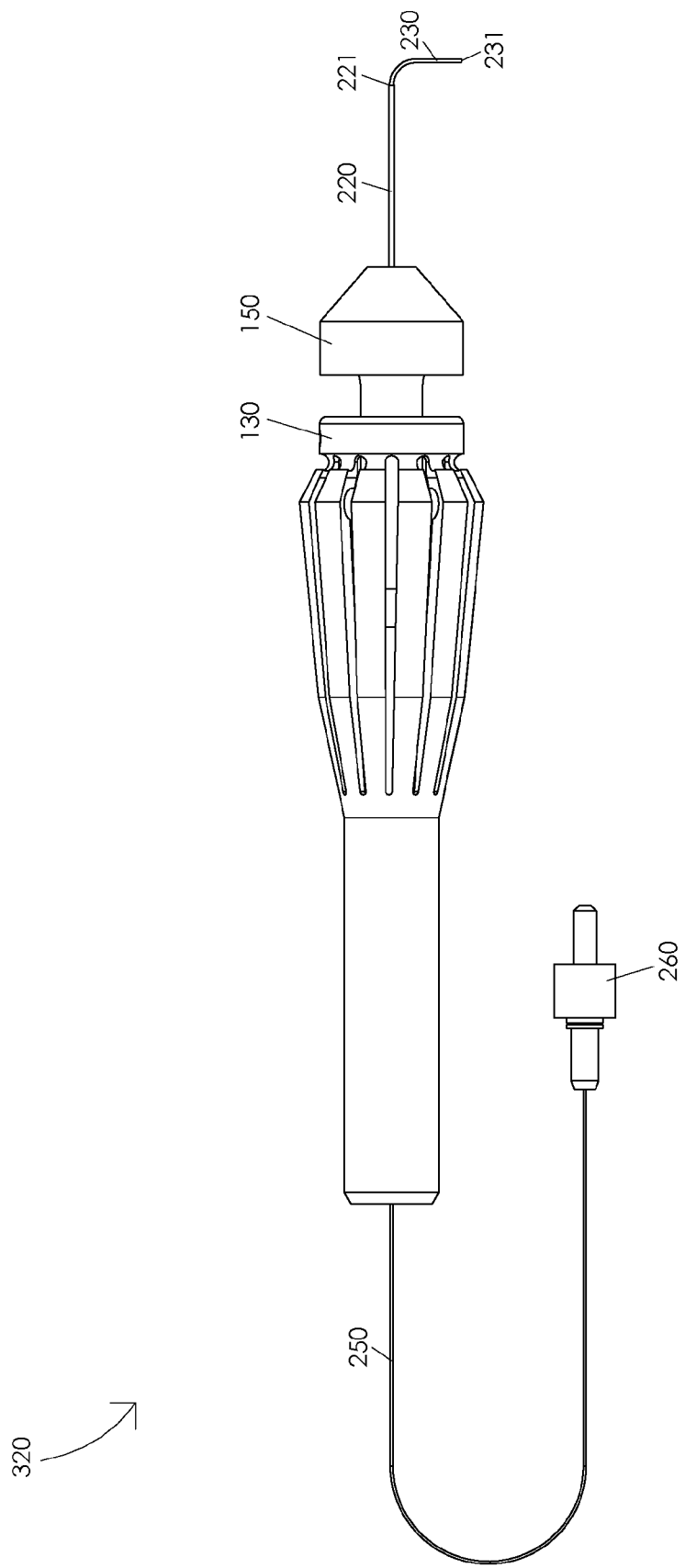

FIG. 3C illustrates an optic fiber in a second curved position 320. In one or more embodiments, a compression of actuation structure 120 may be configured to gradually curve optic fiber 250 from an optic fiber in a first curved position 310 to an optic fiber in a second curved position 320. Illustratively, a compression of actuation structure 120 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a compression of actuation structure 120, may be configured to cause wire 240 to gradually curve flexible tube 230. In one or more embodiments, a gradual curving of flexible tube 230 may be configured to gradually curve optic fiber 250, e.g., from an optic fiber in a first curved position 310 to an optic fiber in a second curved position 320. Illustratively, a line tangent to optic fiber distal end 251 may intersect a line tangent to housing tube proximal end 202 at a second angle, e.g., when optic fiber 250 comprises an optic fiber in a second curved position 320. In one or more embodiments, the second angle may comprise any angle greater than the first angle. For example, the second angle may comprise a 90 degree angle.

Figure 3D:
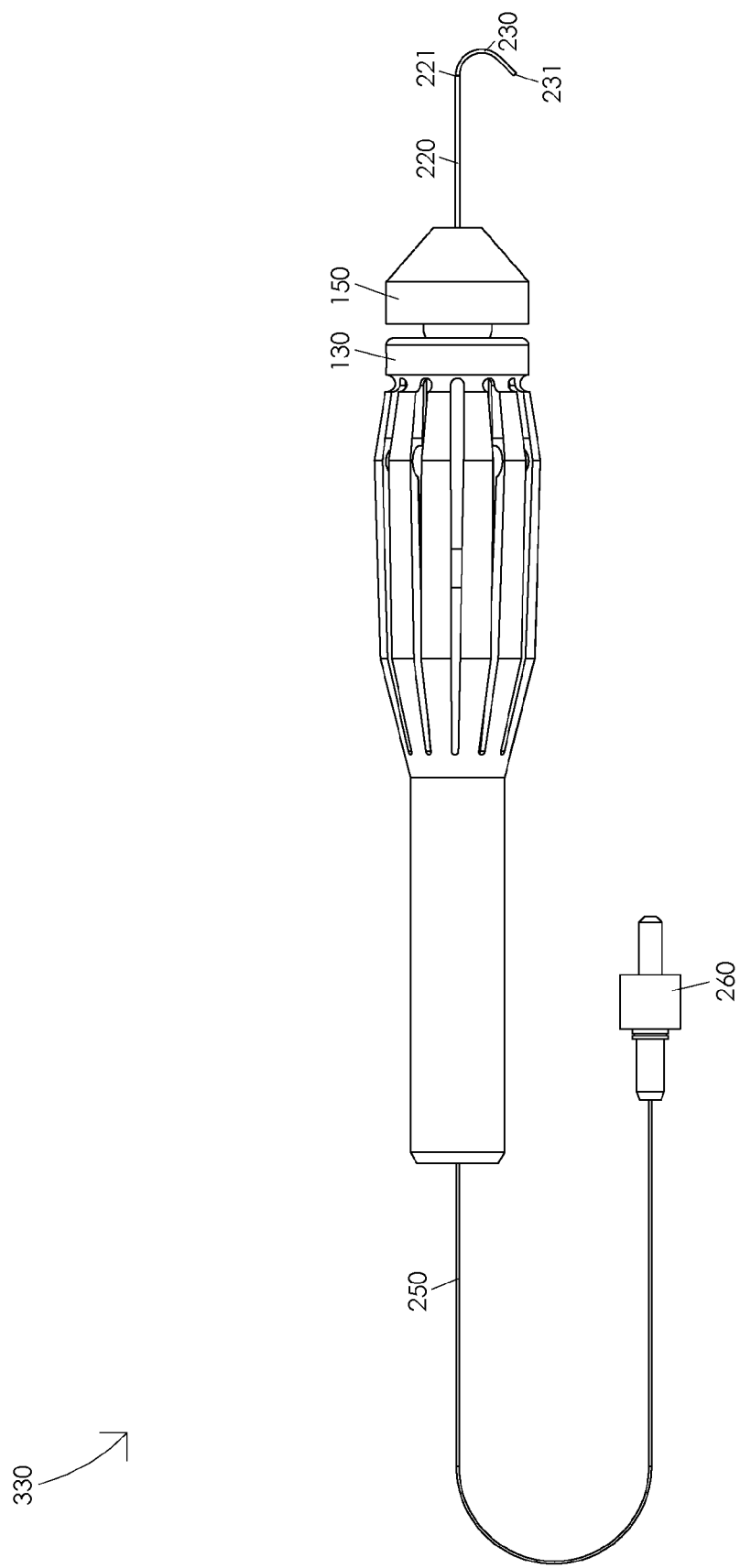

FIG. 3D illustrates an optic fiber in a third curved position 330. In one or more embodiments, a compression of actuation structure 120 may be configured to gradually curve optic fiber 250 from an optic fiber in a second curved position 320 to an optic fiber in a third curved position 330. Illustratively, a compression of actuation structure 120 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a compression of actuation structure 120, may be configured to cause wire 240 to gradually curve flexible tube 230. In one or more embodiments, a gradual curving of flexible tube 230 may be configured to gradually curve optic fiber 250, e.g., from an optic fiber in a second curved position 320 to an optic fiber in a third curved position 330. Illustratively, a line tangent to optic fiber distal end 251 may intersect a line tangent to housing tube proximal end 202 at a third angle, e.g., when optic fiber 250 comprises an optic fiber in a third curved position 330. In one or more embodiments, the third angle may comprise any angle greater than the second angle. For example, the third angle may comprise a 135 degree angle.

Figure 3E:
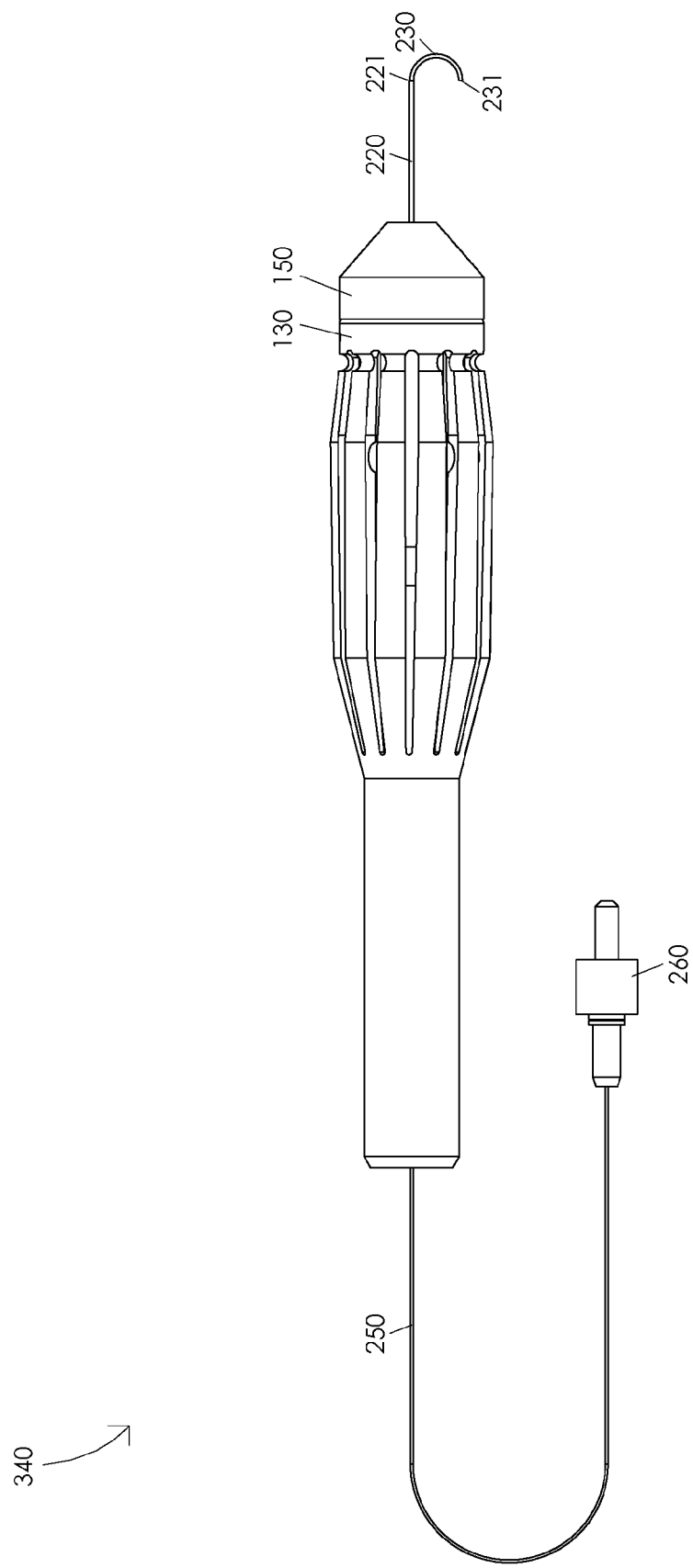

FIG. 3E illustrates an optic fiber in a fourth curved position 340. In one or more embodiments, a compression of actuation structure 120 may be configured to gradually curve optic fiber 250 from an optic fiber in a third curved position 330 to an optic fiber in a fourth curved position 340. Illustratively, a compression of actuation structure 120 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a compression of actuation structure 120, may be configured to cause wire 240 to gradually curve flexible tube 230. In one or more embodiments, a gradual curving of flexible tube 230 may be configured to gradually curve optic fiber 250, e.g., from an optic fiber in a third curved position 330 to an optic fiber in a fourth curved position 340. Illustratively, a line tangent to optic fiber distal end 251 may be parallel to a line tangent to housing tube proximal end 202, e.g., when optic fiber 250 comprises an optic fiber in a fourth curved position 340.

In one or more embodiments, one or more properties of a steerable laser probe may be adjusted to attain one or more desired steerable laser probe features. Illustratively, one or more steerable laser probe components may be manufactured as a single component. In one or more embodiments, housing tube 220 and flexible tube 230 may be manufactured as a single unit. Illustratively, a length that housing tube 220 extends from housing tube platform 150 or a length that flexible tube 230 extends from housing tube distal end 221 may be adjusted to vary an amount of compression of actuation structure 120 configured to curve flexible tube 230 to a particular curved position. In one or more embodiments, a stiffness of flexible tube 230 may be adjusted to vary an amount of compression of actuation structure 120 configured to curve flexible tube 230 to a particular curved position. Illustratively, a stiffness of wire 240 may be adjusted to vary an amount of compression of actuation structure 120 configured to curve flexible tube 230 to a particular curved position. In one or more embodiments, a geometry of actuation structure 120 may be adjusted to vary an amount of compression of actuation structure 120 configured to curve flexible tube 230 to a particular curved position. Illustratively, a geometry of pre-formed curve 245 may be adjusted to vary an amount of compression of actuation structure 120 configured to curve flexible tube 230 to a particular curved position. For example, a length of wire 240 may be adjusted to vary an amount of compression of actuation structure 120 configured to curve flexible tube 230 to a particular curved position. In one or more embodiments, a portion of optic fiber 250 may be enclosed in an optic fiber sleeve configured to, e.g., protect optic fiber 250, vary a stiffness of optic fiber 250, vary an optical property of optic fiber 250, etc.

Figure 4A:
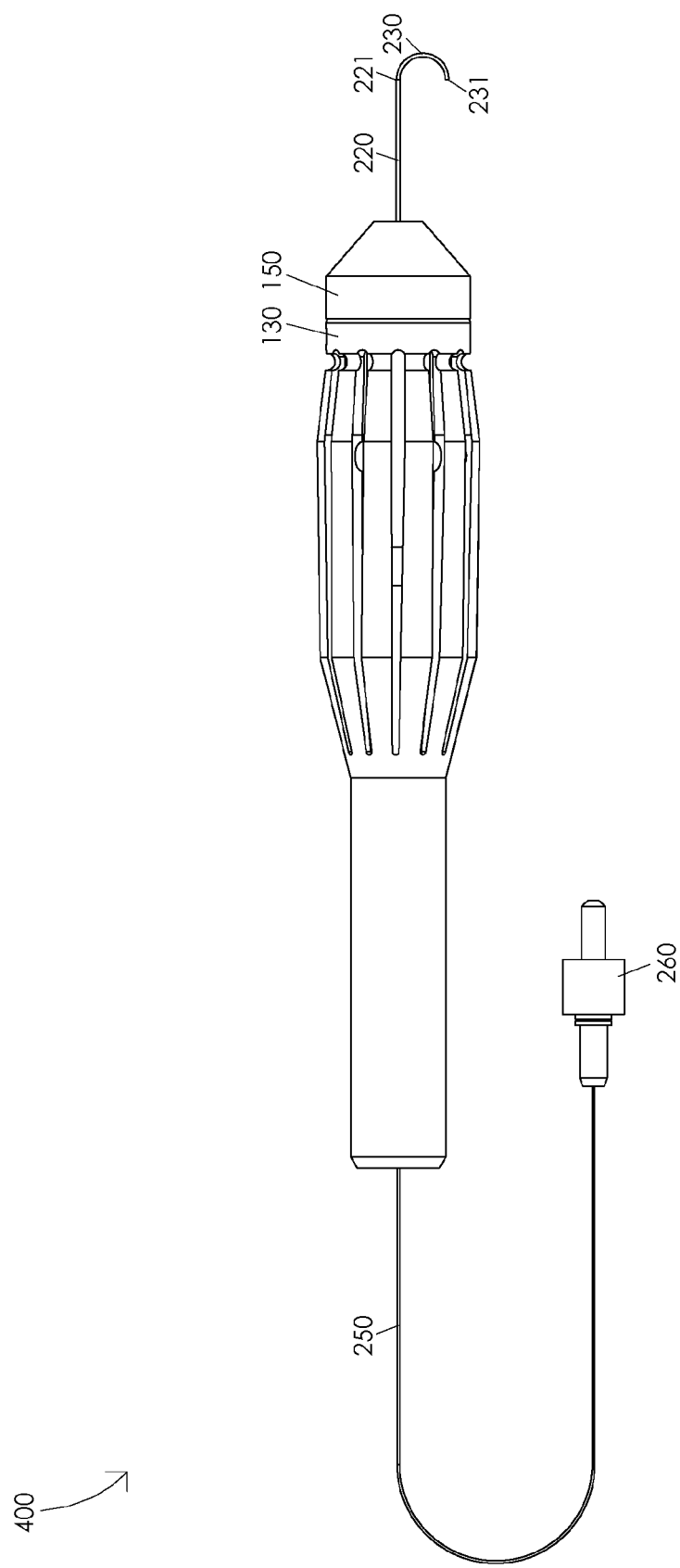
FIGS. 4A, 4B, 4C, 4D, and 4E illustrate a gradual straightening of an optic fiber.

FIGS. 4A, 4B, 4C, 4D, and 4E illustrate a gradual straightening of an optic fiber 250. FIG. 4A illustrates a fully curved optic fiber 400. In one or more embodiments, optic fiber 250 may comprise a fully curved optic fiber 400, e.g., when actuation ring 130 is fully extended relative to handle base 110. Illustratively, optic fiber 250 may comprise a fully curved optic fiber 400, e.g., when actuation structure 120 is fully compressed. In one or more embodiments, optic fiber 250 may comprise a fully curved optic fiber 400, e.g., when wire 240 is fully extended relative to housing tube 220. For example, optic fiber 250 may comprise a fully curved optic fiber 400 when pre-formed curve 245 is fully contained within flexible tube 230. Illustratively, a line tangent to optic fiber distal end 251 may be parallel to a line tangent to housing tube proximal end 202, e.g., when optic fiber 250 comprises a fully curved optic fiber 400.

Figure 4B:
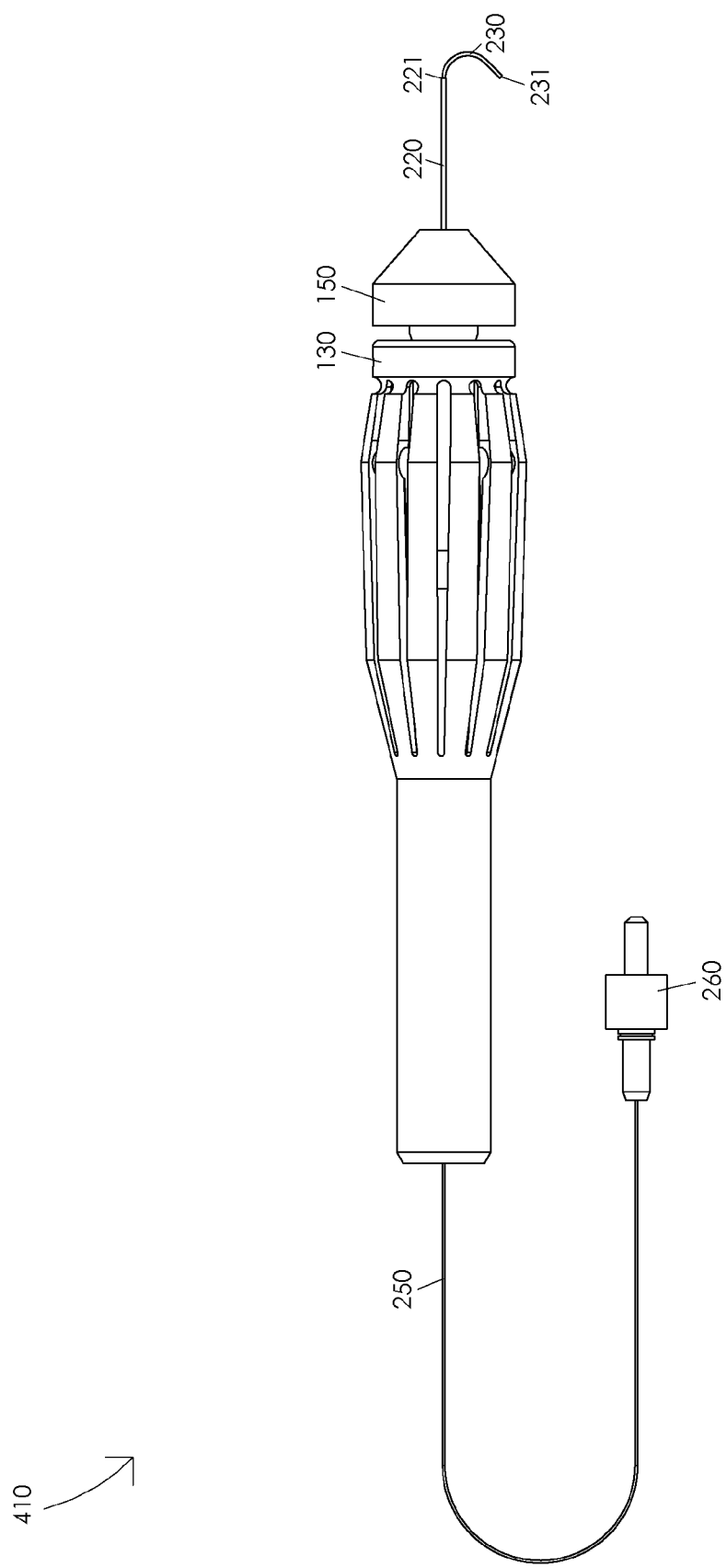

FIG. 4B illustrates an optic fiber in a first partially straightened position 410. In one or more embodiments, a decompression of actuation structure 120 may be configured to gradually straighten optic fiber 250 from a fully curved optic fiber 400 to an optic fiber in a first partially straightened position 410. Illustratively, a decompression of actuation structure 120 may be configured to gradually retract wire 240 relative to housing tube 220. In one or more embodiments, a gradual retraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual retraction of wire 240 out of flexible tube 230, e.g., due to a decompression of actuation structure 120, may be configured to gradually straighten flexible tube 230. In one or more embodiments, a gradual straightening of flexible tube 230 may be configured to gradually straighten optic fiber 250, e.g., from a fully curved optic fiber 400 to an optic fiber in a first partially straightened position 410. Illustratively, a line tangent to optic fiber distal end 251 may intersect a line tangent to housing tube proximal end 202 at a first partially straightened angle, e.g., when optic fiber 250 comprises an optic fiber in a first partially straightened position 410. Illustratively, the first partially straightened angle may comprise any angle less than 180 degrees. For example, the first partially straightened angle may comprise a 135 degree angle.

Figure 4C:
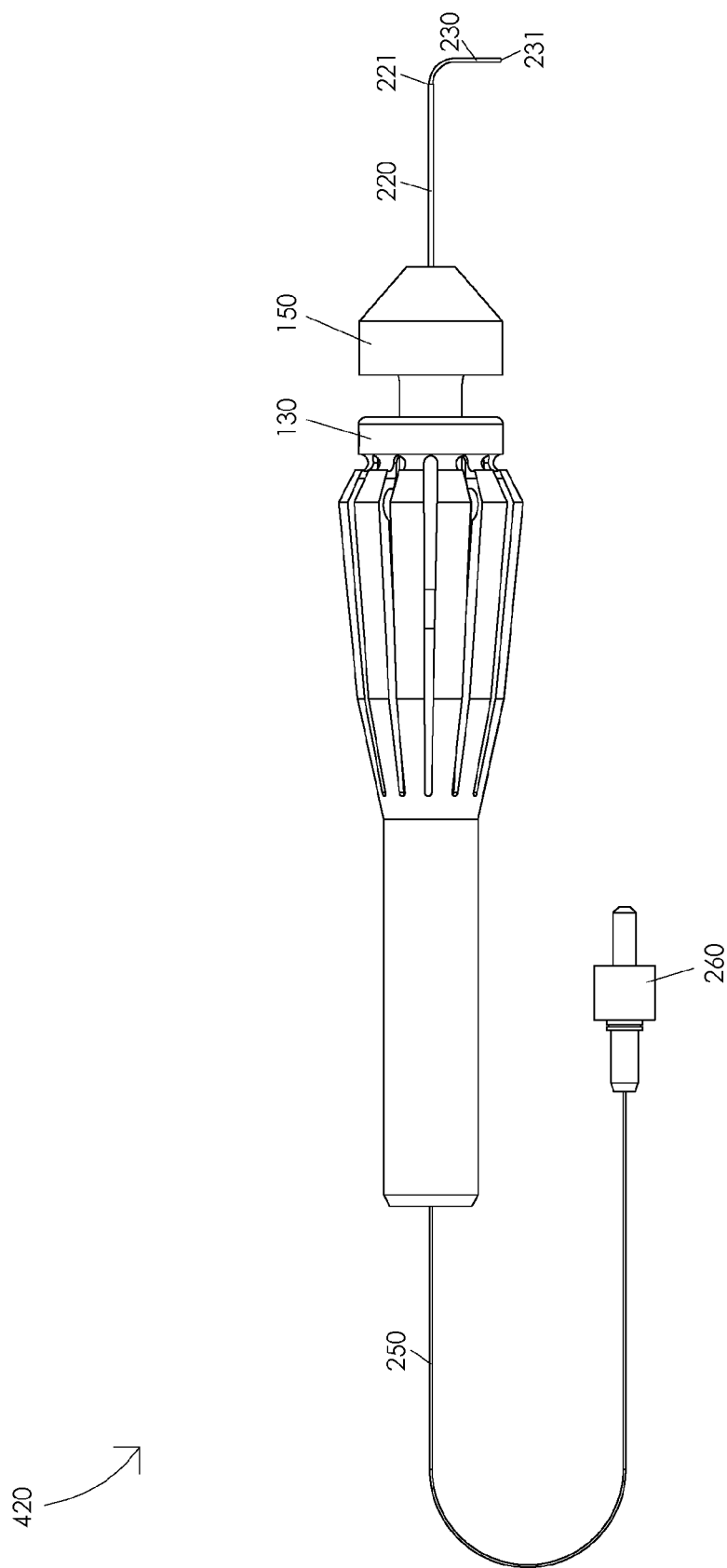

FIG. 4C illustrates an optic fiber in a second partially straightened position 420. In one or more embodiments, a decompression of actuation structure 120 may be configured to gradually straighten optic fiber 250 from an optic fiber in a first partially straightened position 410 to an optic fiber in a second partially straightened position 420. Illustratively, a decompression of actuation structure 120 may be configured to gradually retract wire 240 relative to housing tube 220. In one or more embodiments, a gradual retraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual refraction of wire 240 out of flexible tube 230, e.g., due to a decompression of actuation structure 120, may be configured to gradually straighten flexible tube 230. In one or more embodiments, a gradual straightening of flexible tube 230 may be configured to gradually straighten optic fiber 250, e.g., from an optic fiber in a first partially straightened position 410 to an optic fiber in a second partially straightened position 420. Illustratively, a line tangent to optic fiber distal end 251 may intersect a line tangent to housing tube proximal end 202 at a second partially straightened angle, e.g., when optic fiber 250 comprises an optic fiber in a second partially straightened position 420. Illustratively, the second partially straightened angle may comprise any angle less than the first partially straightened angle. For example, the second partially straightened angle may comprise a 90 degree angle.

Figure 4D:
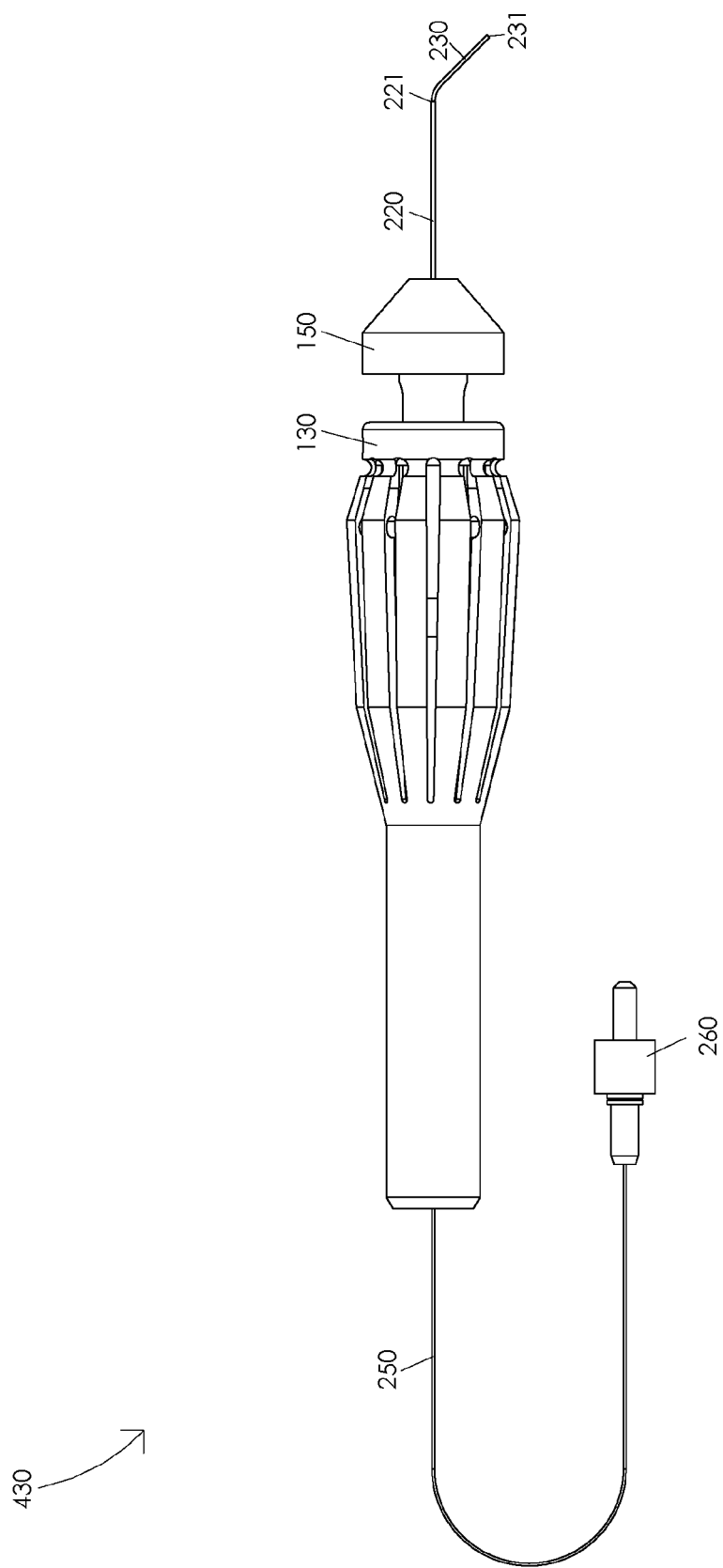

FIG. 4D illustrates an optic fiber in a third partially straightened position 430. In one or more embodiments, a decompression of actuation structure 120 may be configured to gradually straighten optic fiber 250 from an optic fiber in a second partially straightened position 420 to an optic fiber in a third partially straightened position 430. Illustratively, a decompression of actuation structure 120 may be configured to gradually retract wire 240 relative to housing tube 220. In one or more embodiments, a gradual refraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual retraction of wire 240 out of flexible tube 230, e.g., due to a decompression of actuation structure 120, may be configured to gradually straighten flexible tube 230. In one or more embodiments, a gradual straightening of flexible tube 230 may be configured to gradually straighten optic fiber 250, e.g., from an optic fiber in a second partially straightened position 420 to an optic fiber in a third partially straightened position 430. Illustratively, a line tangent to optic fiber distal end 251 may intersect a line tangent to housing tube proximal end 202 at a third partially straightened angle, e.g., when optic fiber 250 comprises an optic fiber in a third partially straightened position 430. Illustratively, the third partially straightened angle may comprise any angle less than the second partially straightened angle. For example, the third partially straightened angle may comprise a 45 degree angle.

Figure 4E:
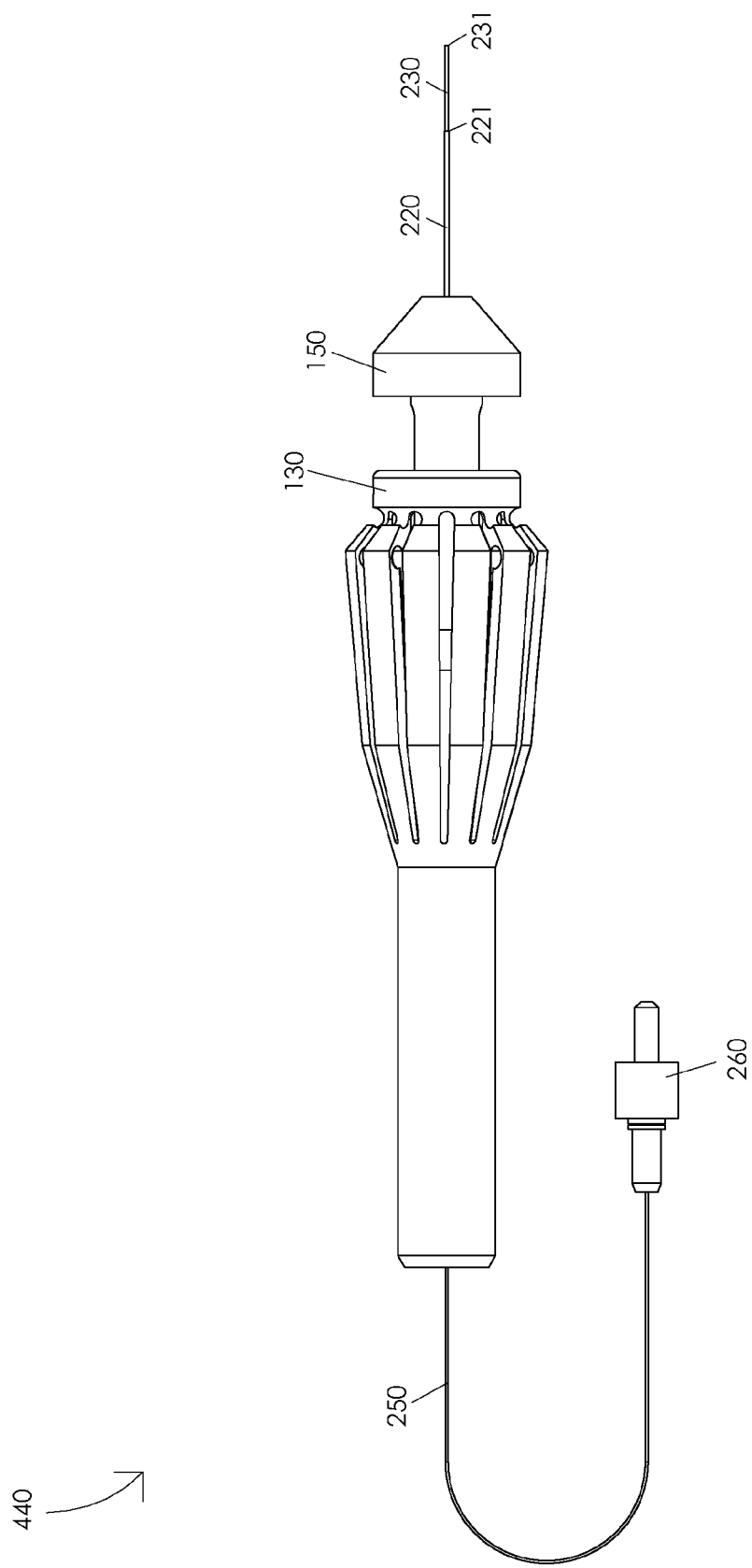

FIG. 4E illustrates an optic fiber in a fully straightened position 440. In one or more embodiments, a decompression of actuation structure 120 may be configured to gradually straighten optic fiber 250 from an optic fiber in a third partially straightened position 430 to an optic fiber in a fully straightened position 440. Illustratively, a decompression of actuation structure 120 may be configured to gradually retract wire 240 relative to housing tube 220. In one or more embodiments, a gradual retraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual refraction of wire 240 out of flexible tube 230, e.g., due to a decompression of actuation structure 120, may be configured to gradually straighten flexible tube 230. In one or more embodiments, a gradual straightening of flexible tube 230 may be configured to gradually straighten optic fiber 250, e.g., from an optic fiber in a third partially straightened position 430 to an optic fiber in a fully straightened position 440. Illustratively, a line tangent to optic fiber distal end 251 may be parallel to a line tangent to housing tube proximal end 202, e.g., when optic fiber 250 comprises an optic fiber in a fully straightened position 440.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient flexible tube 230 in an orientation configured to cause a curvature of flexible tube 230 within the particular transverse plane of the inner eye and varying an amount of compression of actuation structure 120. Illustratively, a surgeon may aim optic fiber distal end 251 at any target within a particular sagittal plane of the inner eye by, e.g., rotating handle 100 to orient flexible tube 230 in an orientation configured to cause a curvature of flexible tube 230 within the particular sagittal plane of the inner eye and varying an amount of compression of actuation structure 120. In one or more embodiments, a surgeon may aim optic fiber distal end 251 at any target within a particular frontal plane of the inner eye by, e.g., varying an amount of compression of actuation structure 120 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying an amount of compression of actuation structure 120. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 5A and 5B are schematic diagrams illustrating a handle 500. FIG. 5A illustrates a top view of handle 500. In one or more embodiments, handle 500 may comprise a handle distal end 501, a handle proximal end 502, a handle base 505, an actuation structure 510, an actuation platform 520, and a housing tube platform 525. Illustratively, actuation platform 520 may comprise an actuation platform distal end 521 and an actuation platform proximal end 522. In one or more embodiments, actuation structure 510 may comprise a plurality of actuation arms 513. Illustratively, each actuation arm 513 may comprise at least one extension mechanism 514. In one or more embodiments, each actuation arm 513 may comprise an inverted actuation joint 515.

Illustratively, actuation structure 510 may be compressed, e.g., by an application of a compressive force to actuation structure 510. In one or more embodiments, actuation structure 510 may be compressed by an application of one or more compressive forces located at one or more locations around an outer perimeter of actuation structure 510. Illustratively, the one or more locations may comprise any of a plurality of locations around the outer perimeter of actuation structure 510. For example, a surgeon may corns press actuation structure 510, e.g., by squeezing actuation structure 510. Illustratively, the surgeon may compress actuation structure 510 by squeezing actuation structure 510 at any particular location of a plurality of locations around an outer perimeter of actuation structure 510. For example, a surgeon may rotate handle 500 and compress actuation structure 510 from any rotational position of a plurality of rotational positions of handle 500.

In one or more embodiments, actuation structure 510 may be compressed by an application of a compressive force to any one or more of the plurality of actuation arms 513. Illustratively, each actuation arm 513 may be configured to actuate independently. In one or more embodiments, each actuation arm 513 may be connected to one or more of the plurality of actuation arms 513 wherein an actuation of a particular actuation arm 513 may be configured to actuate every actuation arm 513 of the plurality of actuation arms 513. In one or more embodiments, a compression of actuation structure 510, e.g., due to an application of a compressive force to a particular actuation arm 513, may be configured to actuate the particular actuation arm 513. Illustratively, an actuation of the particular actuation arm 513 may be configured to actuate every actuation arm 513 of the plurality of actuation arms 513. In one or more embodiments, an application of a compressive force to a particular actuation arm 513 may be configured to extend at least one extension mechanism 514 of the particular actuation arm 513.

Illustratively, an application of a compressive force to a particular actuation arm 513 may be configured to retract actuation platform 520 relative to handle base 505. In one or more embodiments, as a particular actuation arm 513 is compressed, e.g., due to an application of a compressive force to the particular actuation arm 513, an inverted actuation joint 515 of the particular actuation arm 513 may be configured to gradually retract actuation platform 520 relative to handle base 505. For example, when a compressive force is applied to a particular actuation arm 513, e.g., and the particular actuation arm 513 is extended by at least one extension mechanism 514 of the particular actuation arm 513, an inverted actuation joint 515 of the particular actuation arm 513 may be configured to retract actuation platform 520 relative to handle base 505.

FIG. 5B illustrates a cross-sectional view of handle 500. In one or more embodiments, handle 500 may comprise an inner bore 560, an inner bore proximal taper 561, an actuation mechanism housing 535, an inner bore distal chamber 562, and a wire guide 590. Handle 500 may be manufactured from any suitable material, e.g., polymers, metals, metal alloys, etc., or from any combination of suitable materials.

Figure 6:
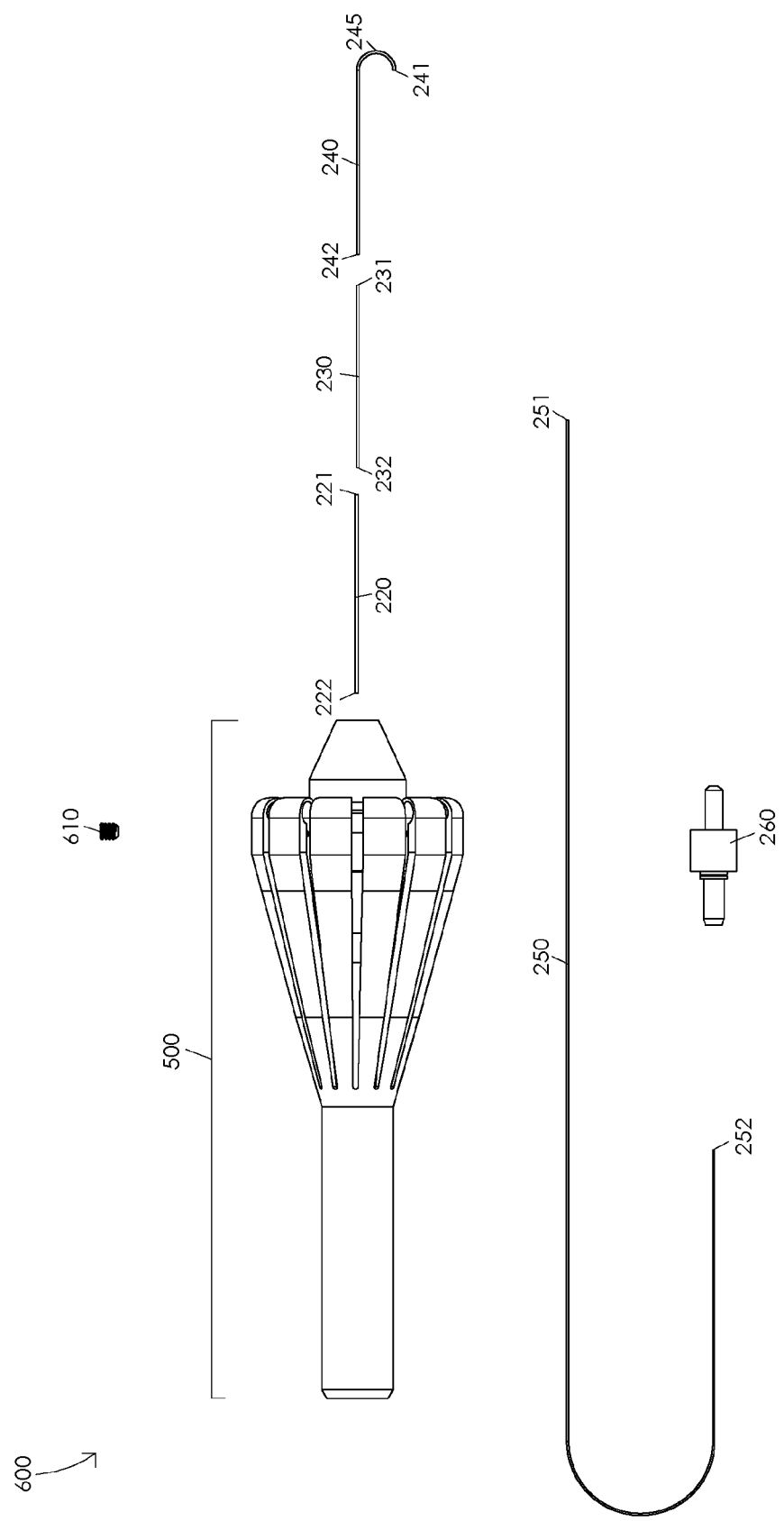
FIG. 6 is a schematic diagram illustrating an exploded view of a steerable laser probe assembly.

FIG. 6 is a schematic diagram illustrating an exploded view of a steerable laser probe assembly 600. In one or more embodiments, steerable laser probe assembly 600 may comprise a handle 500; an actuation mechanism 610; a housing tube 220 having a housing tube distal end 221 and a housing tube proximal end 222; a flexible tube 230 having a flexible tube distal end 231 and a flexible tube proximal end 232; a wire 240 having a wire distal end 241, a wire proximal end 242, and a pre-formed curve 245; an optic fiber 250 having an optic fiber distal end 251 and an optic fiber proximal end 252; and a light source interface 260. Illustratively, light source interface 260 may be configured to interface with optic fiber 250, e.g., at optic fiber proximal end 252. In one or more embodiments, light source interface 260 may comprise a standard light source connector, e.g., an SMA connector.

Illustratively, housing tube 220 may be fixed to housing tube platform 525, e.g., housing tube proximal end 222 may be fixed to handle distal end 501. In one or more embodiments, housing tube 220 may be fixed to housing tube platform 525, e.g., by an adhesive or by any other suitable fixation means. Illustratively, a portion of housing tube 220 may be disposed within wire guide 590, e.g., housing tube proximal end 222 may be disposed within wire guide 590. In one or more embodiments, a portion of housing tube 220 may be fixed within wire guide 590, e.g., by an adhesive or other any suitable fixation means. Housing tube 220 may be manufactured from any suitable material, e.g., polymers, metals, metal alloys, etc., or from any combination of suitable materials.

In one or more embodiments, a portion of flexible tube 230 may be disposed within housing tube 220, e.g., flexible tube proximal end 232 may be disposed within housing tube 220. Illustratively, a portion of flexible tube 230 may extend from housing tube 220, e.g., flexible tube distal end 231 may extend from housing tube distal end 221. In one or more embodiments, a portion of flexible tube 230 may be fixed within housing tube 220, e.g., by an adhesive or any other suitable fixation means. Illustratively, a portion of flexible tube 230 may be disposed within a portion of housing tube 220. In one or more embodiments, a portion of flexible tube 230 may be disposed within wire guide 590, e.g., flexible tube proximal end 232 may be disposed within wire guide 590. Illustratively, a portion of flexible tube 230 may be fixed within wire guide 590, e.g., by an adhesive or any other suitable fixation means. In one or more embodiments, a portion of flexible tube 230 may be fixed to housing tube platform 525, e.g., by an adhesive or any other suitable fixation means. Flexible tube 230 may be manufactured from any suitable material, e.g., polymers, metals, metal alloys, etc., or from any combination of suitable materials.

Illustratively, optic fiber 250 may be disposed within inner bore 560, inner bore distal chamber 562, wire guide 590, housing tube 220, and flexible tube 230. In one or more embodiments, optic fiber 250 may be disposed within flexible tube 230 wherein optic fiber distal end 251 may be adjacent to flexible tube distal end 231. Illustratively, a portion of optic fiber 250 may be fixed to an inner portion of flexible tube 230, e.g., by an adhesive or any other suitable fixation means. In one or more embodiments, a portion of optic fiber 250 may be fixed to an inner portion of housing tube 220, e.g., by an adhesive or any other suitable fixation means. Illustratively, optic fiber 250 may be configured to transmit light, e.g., light from a light source.

In one or more embodiments, a portion of wire 240 may comprise a shape memory material, e.g., Nitinol. Illustratively, pre-formed curve 245 may comprise a shape memory material, e.g., Nitinol. In one or more embodiments, wire 240 may be disposed within actuation mechanism housing 535, wire guide 590, and housing tube 220. Illustratively, a portion of wire 240 may be disposed within flexible tube 230. In one or more embodiments, actuation mechanism 610 may be housed within actuation mechanism housing 535. Illustratively, actuation mechanism 610 may be configured to fix a portion of wire 240, e.g., wire proximal end 242, in a position relative to actuation platform 520. In one or more embodiments, actuation mechanism 610 may comprise a set screw configured to fix wire 240 in a position relative to actuation platform 520, e.g., by a press fit or any other suitable fixation means. Illustratively, a portion of wire 240, e.g., wire proximal end 242, may be fixed to actuation mechanism 610, e.g., by an adhesive or any other suitable fixation means. Wire 240 may be manufactured from any suitable material, e.g., polymers, metals, metal alloys, etc., or from any combination of suitable materials.

In one or more embodiments, a compression of action structure 510 may be configured to retract actuation platform 520, e.g., towards handle proximal end 502 and away from handle distal end 501. Illustratively, as action structure 510 is compressed, e.g., due to an application of a force to one or more actuation arms 513, one or more inverted actuation joints 515 may be configured to apply a force to actuation platform 520. In one or more embodiments, an application of a force to actuation platform 520 may be configured to actuate actuation platform 520 towards handle proximal end 502 and away from handle distal end 501. Illustratively, a compression of actuation structure 510 may be configured to actuate actuation mechanism 610 and actuation platform 520, e.g., towards handle proximal end 502 and away from handle distal end 501.

In one or more embodiments, a compression of actuation structure 510 may be configured to retract wire 240 relative to housing tube 220. Illustratively, a compression of actuation structure 510 may be configured to retract a portion of pre-formed curve 245 into housing tube 220. In one or more embodiments, housing tube 220 may be configured to generally straighten a portion of pre-formed curve 245, e.g., a portion of pre-formed curve 245 disposed within housing tube 220. Illustratively, a compression of actuation structure 510 may be configured to retract a portion of pre-formed curve 245 into housing tube 220, e.g., out of a portion of flexible tube 230 extending from housing tube distal end 221, causing flexible tube 230 to gradually straighten. In one or more embodiments, a gradual straightening of flexible tube 230 may be configured to gradually straighten optic fiber 250.

In one or more embodiments, a decompression of actuation structure 510 may be configured to extend actuation platform 520, e.g., towards handle distal end 501 and away from handle proximal end 502. Illustratively, as action structure 510 is decompressed, e.g., due to a reduction of a force applied to one or more actuation arms 513, one or more inverted actuation joints 515 may be configured to reduce a force applied to actuation platform 520. In one or more embodiments, a reduction of a force applied to actuation platform 520 may be configured to actuate actuation platform 520 towards handle distal end 501 and away from handle proximal end 502. Illustratively, a decompression of actuation structure 510 may be configured to actuate actuation mechanism 610 and actuation platform 520, e.g., towards handle distal end 501 and away from handle proximal end 502.

In one or more embodiments, a decompression of actuation structure 510 may be configured to extend wire 240 relative to housing tube 220. Illustratively, a decompression of actuation structure 510 may be configured to extend a portion of pre-formed curve 245 out from housing tube 220, e.g., out from housing tube distal end 221. In one or more embodiments, housing tube 220 may be configured to generally straighten a portion of pre-formed curve 245, e.g., a portion of pre-formed curve 245 disposed within housing tube 220. Illustratively, a decompression of actuation structure 510 may be configured to extend a portion of pre-formed curve 245 out from housing tube 220, e.g., into a portion of flexible tube 230 extending from housing tube distal end 221, causing flexible tube 230 to gradually curve. In one or more embodiments, a gradual curving of flexible tube 230 may be configured to gradually curve optic fiber 250.

Figure 7B:
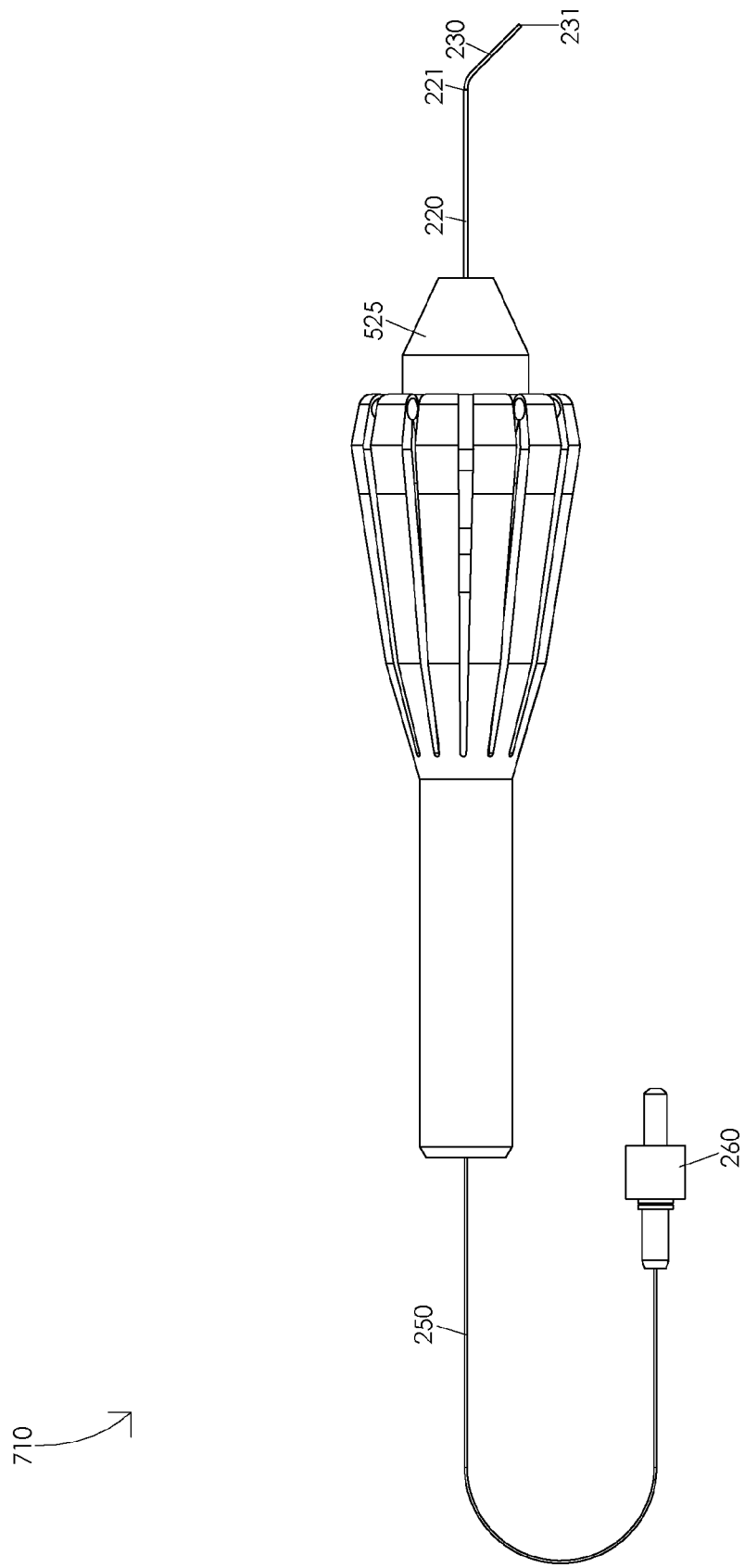

FIGS. 7A, 7B, 7C, 7D, and 7E illustrate a gradual curving of an optic fiber 250. FIG. 7A illustrates a straight optic fiber 700. In one or more embodiments, optic fiber 250 may comprise a straight optic fiber 700, e.g., when actuation platform 520 is fully refracted relative to handle base 505. Illustratively, optic fiber 250 may comprise a straight optic fiber 700, e.g., when actuation structure 510 is fully compressed. In one or more embodiments, optic fiber 250 may comprise a straight optic fiber 700, e.g., when wire 240 is fully retracted relative to housing tube 220. For example, optic fiber 250 may comprise a straight optic fiber 700 when pre-formed curve 245 is fully contained within housing tube 220. Illustratively, a line tangent to optic fiber distal end 251 may be parallel to a line tangent to housing tube proximal end 202, e.g., when optic fiber 250 comprises a straight optic fiber 700.

FIG. 7B illustrates an optic fiber in a first curved position 710. In one or more embodiments, a decompression of actuation structure 510 may be configured to gradually curve optic fiber 250 from a straight optic fiber 700 to an optic fiber in a first curved position 710. Illustratively, a decompression of actuation structure 510 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a decompression of actuation structure 510, may be configured to cause wire 240 to gradually curve flexible tube 230. In one or more embodiments, a gradual curving of flexible tube 230 may be configured to gradually curve optic fiber 250, e.g., from a straight optic fiber 700 to an optic fiber in a first curved position 710. Illustratively, a line tangent to optic fiber distal end 251 may intersect a line tangent to housing tube proximal end 202 at a first angle, e.g., when optic fiber 250 comprises an optic fiber in a first curved position 710. In one or more embodiments, the first angle may comprise any angle greater than zero degrees. For example, the first angle may comprise a 45 degree angle.

Figure 7C:
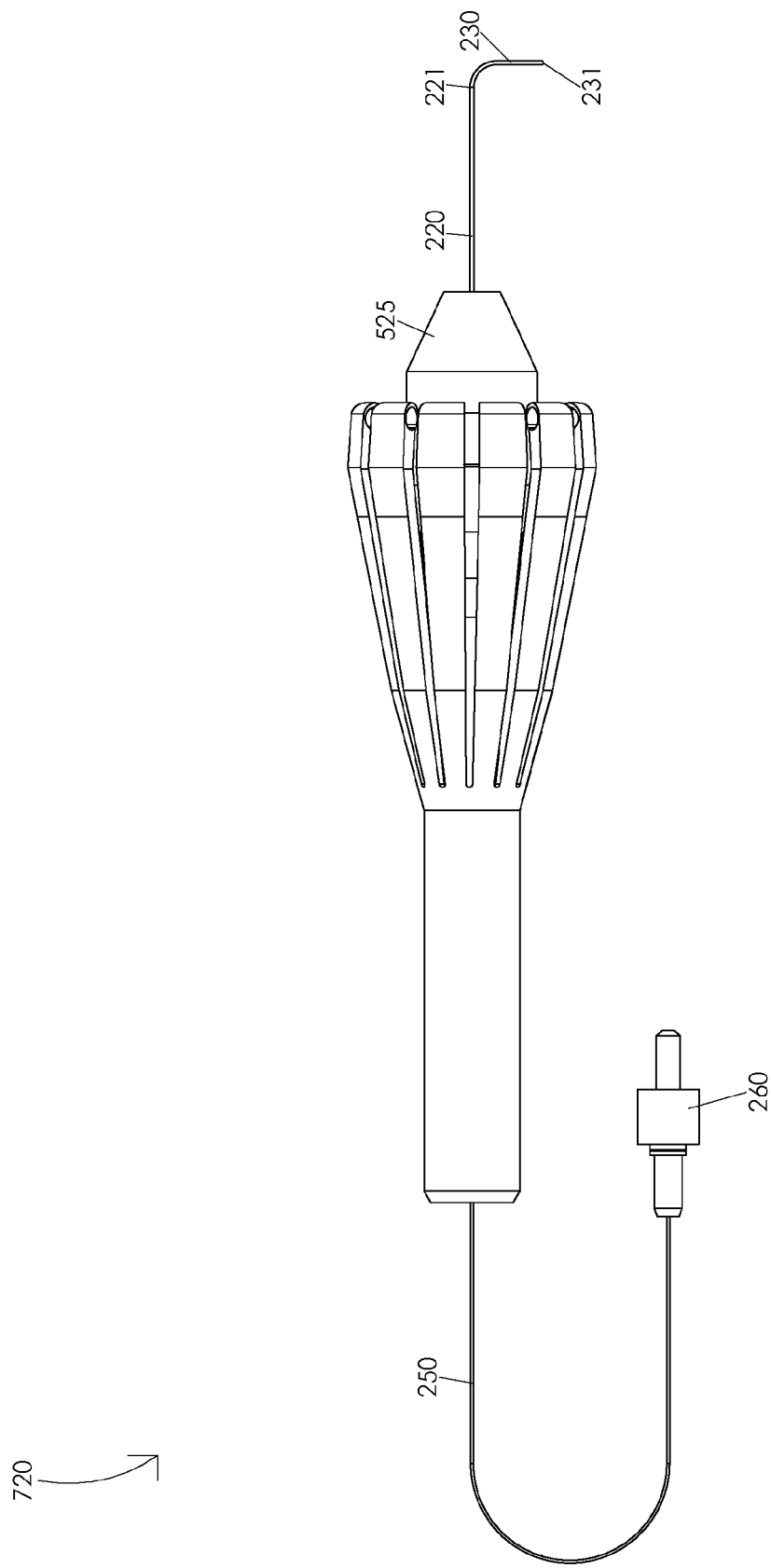

FIG. 7C illustrates an optic fiber in a second curved position 720. In one or more embodiments, a decompression of actuation structure 510 may be configured to gradually curve optic fiber 250 from an optic fiber in a first curved position 710 to an optic fiber in a second curved position 720. Illustratively, a decompression of actuation structure 510 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a decompression of actuation structure 510, may be configured to cause wire 240 to gradually curve flexible tube 230. In one or more embodiments, a gradual curving of flexible tube 230 may be configured to gradually curve optic fiber 250, e.g., from an optic fiber in a first curved position 710 to an optic fiber in a second curved position 720. Illustratively, a line tangent to optic fiber distal end 251 may intersect a line tangent to housing tube proximal end 202 at a second angle, e.g., when optic fiber 250 comprises an optic fiber in a second curved position 720. In one or more embodiments, the second angle may comprise any angle greater than the first angle. For example, the second angle may comprise a 90 degree angle.

Figure 7D:
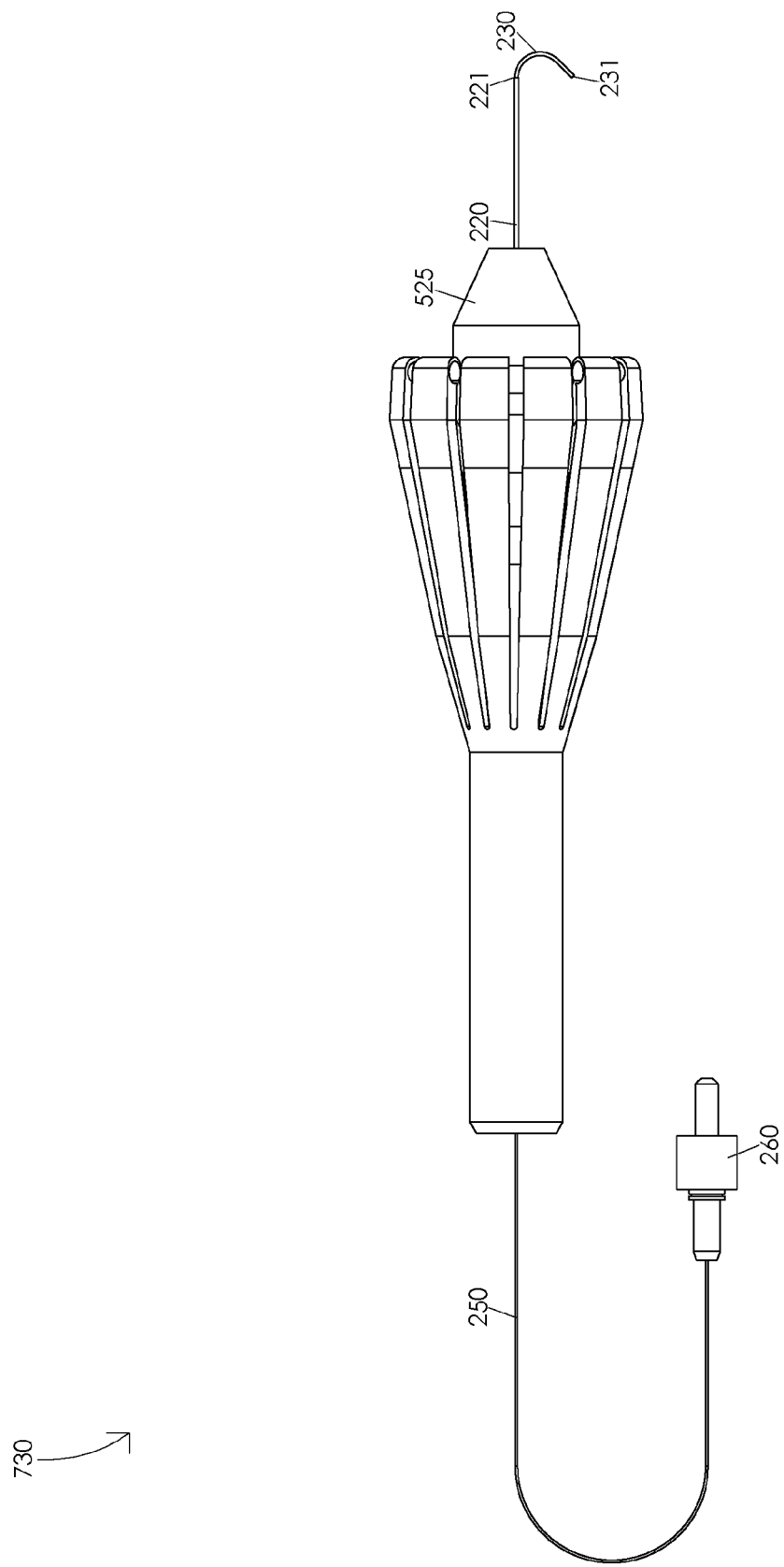

FIG. 7D illustrates an optic fiber in a third curved position 730. In one or more embodiments, a decompression of actuation structure 510 may be configured to gradually curve optic fiber 250 from an optic fiber in a second curved position 720 to an optic fiber in a third curved position 730. Illustratively, a decompression of actuation structure 510 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a decompression of actuation structure 510, may be configured to cause wire 240 to gradually curve flexible tube 230. In one or more embodiments, a gradual curving of flexible tube 230 may be configured to gradually curve optic fiber 250, e.g., from an optic fiber in a second curved position 720 to an optic fiber in a third curved position 730. Illustratively, a line tangent to optic fiber distal end 251 may intersect a line tangent to housing tube proximal end 202 at a third angle, e.g., when optic fiber 250 comprises an optic fiber in a third curved position 730. In one or more embodiments, the third angle may comprise any angle greater than the second angle. For example, the third angle may comprise a 135 degree angle.

Figure 7E:
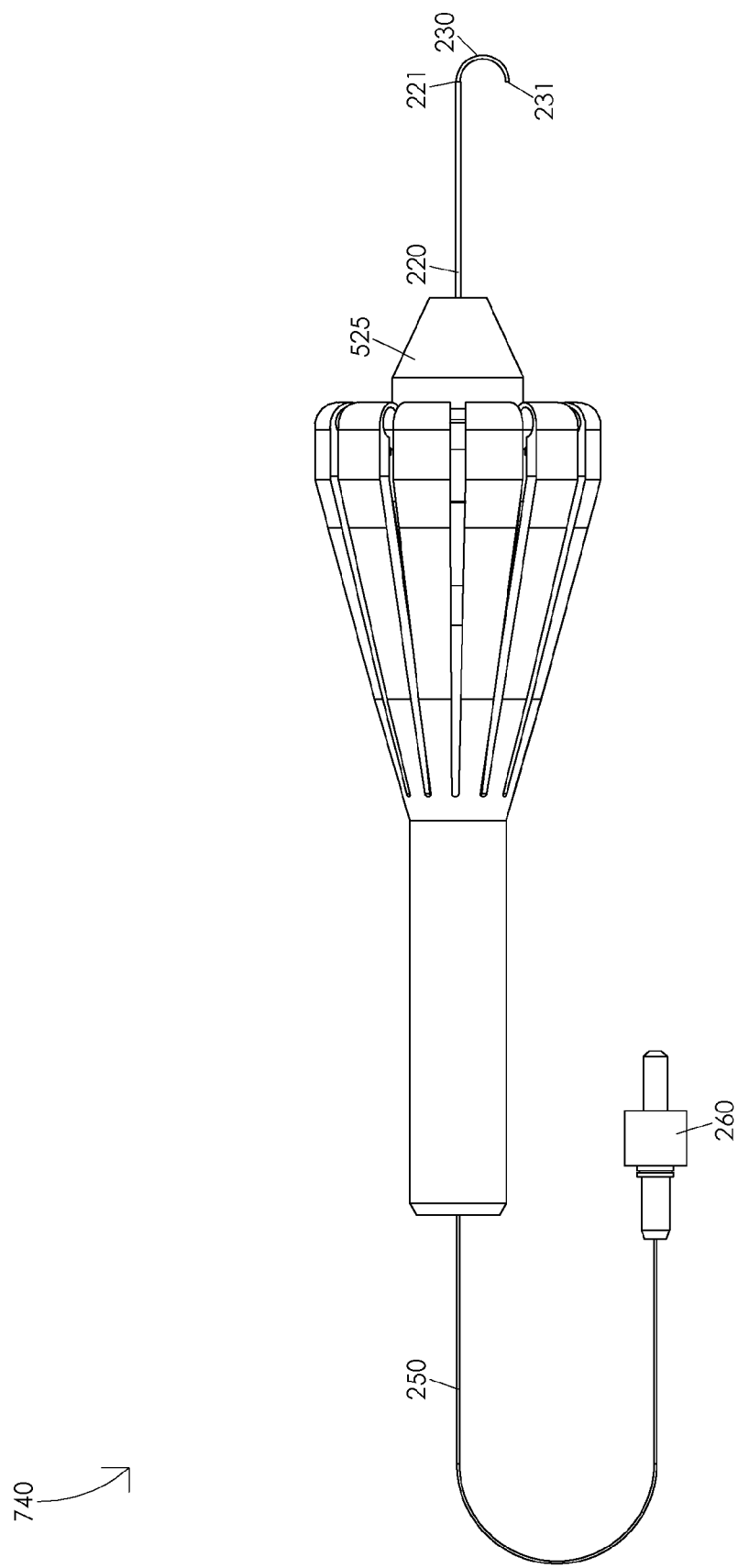

FIG. 7E illustrates an optic fiber in a fourth curved position 740. In one or more embodiments, a decompression of actuation structure 510 may be configured to gradually curve optic fiber 250 from an optic fiber in a third curved position 730 to an optic fiber in a fourth curved position 740. Illustratively, a decompression of actuation structure 510 may be configured to gradually extend wire 240 relative to housing tube 220. In one or more embodiments, a gradual extension of wire 240 relative to housing tube 220 may be configured to gradually extend a portion of pre-formed curve 245 into a portion of flexible tube 230, e.g., a portion of flexible tube 230 projecting out of housing tube distal end 221. Illustratively, a gradual extension of wire 240 into flexible tube 230, e.g., due to a decompression of actuation structure 510, may be configured to cause wire 240 to gradually curve flexible tube 230. In one or more embodiments, a gradual curving of flexible tube 230 may be configured to gradually curve optic fiber 250, e.g., from an optic fiber in a third curved position 730 to an optic fiber in a fourth curved position 740. Illustratively, a line tangent to optic fiber distal end 251 may be parallel to a line tangent to housing tube proximal end 202, e.g., when optic fiber 250 comprises an optic fiber in a fourth curved position 740.

In one or more embodiments, one or more properties of a steerable laser probe may be adjusted to attain one or more desired steerable laser probe features. Illustratively, one or more steerable laser probe components may be manufactured as a single component. In one or more embodiments, housing tube 220 and flexible tube 230 may be manufactured as a single unit. Illustratively, a length that housing tube 220 extends from housing tube platform 525 or a length that flexible tube 230 extends from housing tube distal end 221 may be adjusted to vary an amount of decompression of actuation structure 510 configured to curve flexible tube 230 to a particular curved position. In one or more embodiments, a stiffness of flexible tube 230 may be adjusted to vary an amount of decompression of actuation structure 510 configured to curve flexible tube 230 to a particular curved position. Illustratively, a stiffness of wire 240 may be adjusted to vary an amount of decompression of actuation structure 510 configured to curve flexible tube 230 to a particular curved position. In one or more embodiments, a geometry of actuation structure 510 may be adjusted to vary an amount of decompression of actuation structure 510 configured to curve flexible tube 230 to a particular curved position. Illustratively, a geometry of pre-formed curve 245 may be adjusted to vary an amount of decompression of actuation structure 510 configured to curve flexible tube 230 to a particular curved position. For example, a length of wire 240 may be adjusted to vary an amount of decompression of actuation structure 510 configured to curve flexible tube 230 to a particular curved position. In one or more embodiments, a portion of optic fiber 250 may be enclosed in an optic fiber sleeve configured to, e.g., protect optic fiber 250, vary a stiffness of optic fiber 250, vary an optical property of optic fiber 250, etc.

Figure 8A:
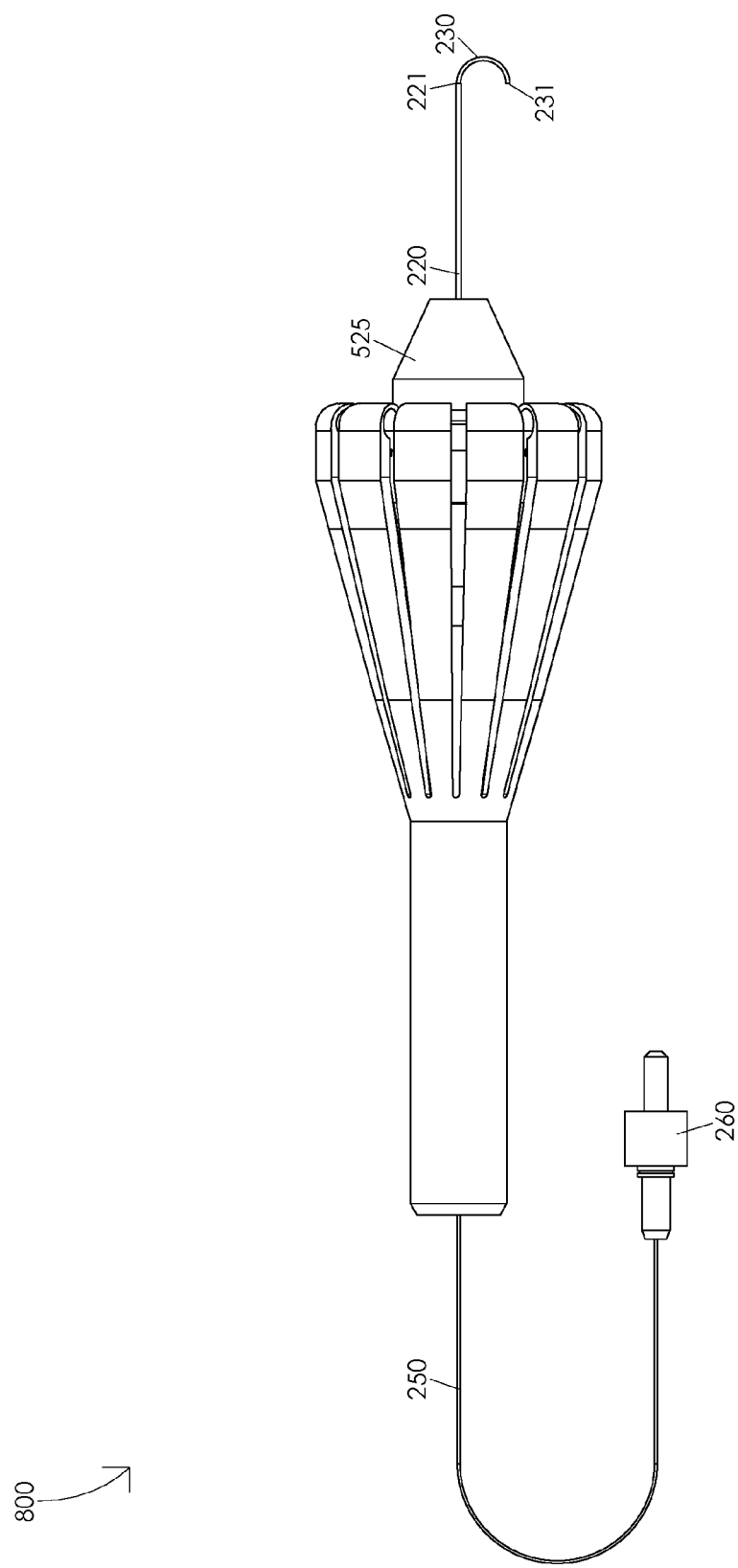
FIGS. 8A, 8B, 8C, 8D, and 8E illustrate a gradual straightening of an optic fiber.

FIGS. 8A, 8B, 8C, 8D, and 8E illustrate a gradual straightening of an optic fiber 250. FIG. 8A illustrates a fully curved optic fiber 800. In one or more embodiments, optic fiber 250 may comprise a fully curved optic fiber 800, e.g., when actuation platform 520 is fully extended relative to handle base 505. Illustratively, optic fiber 250 may comprise a fully curved optic fiber 800, e.g., when actuation structure 510 is fully decompressed. In one or more embodiments, optic fiber 250 may comprise a fully curved optic fiber 800, e.g., when wire 240 is fully extended relative to housing tube 220. For example, optic fiber 250 may comprise a fully curved optic fiber 800 when pre-formed curve 245 is fully contained within flexible tube 230. Illustratively, a line tangent to optic fiber distal end 251 may be parallel to a line tangent to housing tube proximal end 202, e.g., when optic fiber 250 comprises a fully curved optic fiber 800.

Figure 8B:
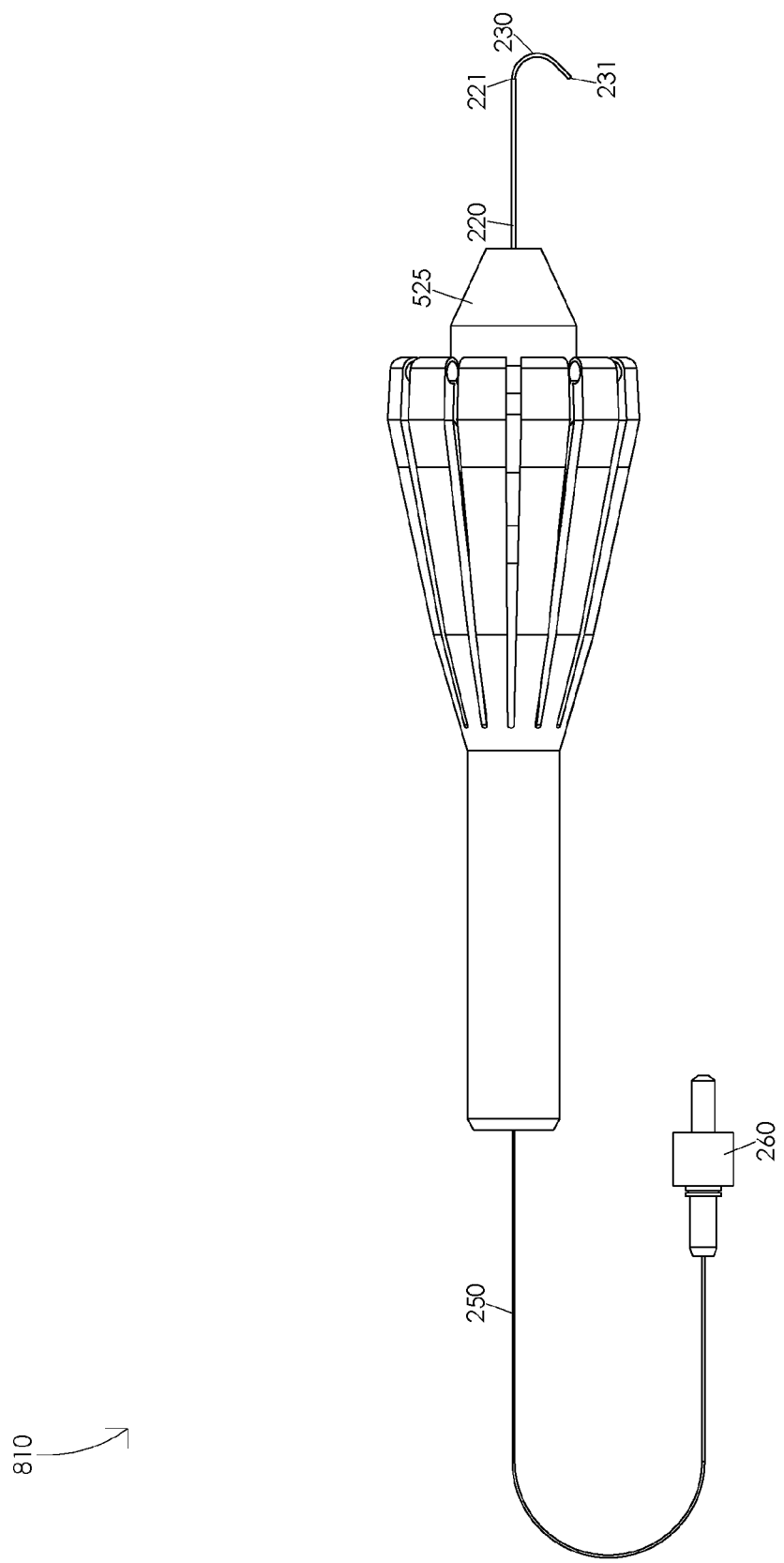

FIG. 8B illustrates an optic fiber in a first partially straightened position 810. In one or more embodiments, a compression of actuation structure 510 may be configured to gradually straighten optic fiber 250 from a fully curved optic fiber 800 to an optic fiber in a first partially straightened position 810. Illustratively, a compression of actuation structure 510 may be configured to gradually retract wire 240 relative to housing tube 220. In one or more embodiments, a gradual retraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual retraction of wire 240 out of flexible tube 230, e.g., due to a compression of actuation structure 510, may be configured to gradually straighten flexible tube 230. In one or more embodiments, a gradual straightening of flexible tube 230 may be configured to gradually straighten optic fiber 250, e.g., from a fully curved optic fiber 800 to an optic fiber in a first partially straightened position 810. Illustratively, a line tangent to optic fiber distal end 251 may intersect a line tangent to housing tube proximal end 202 at a first partially straightened angle, e.g., when optic fiber 250 comprises an optic fiber in a first partially straightened position 810. Illustratively, the first partially straightened angle may comprise any angle less than 180 degrees. For example, the first partially straightened angle may comprise a 135 degree angle.

Figure 8C:
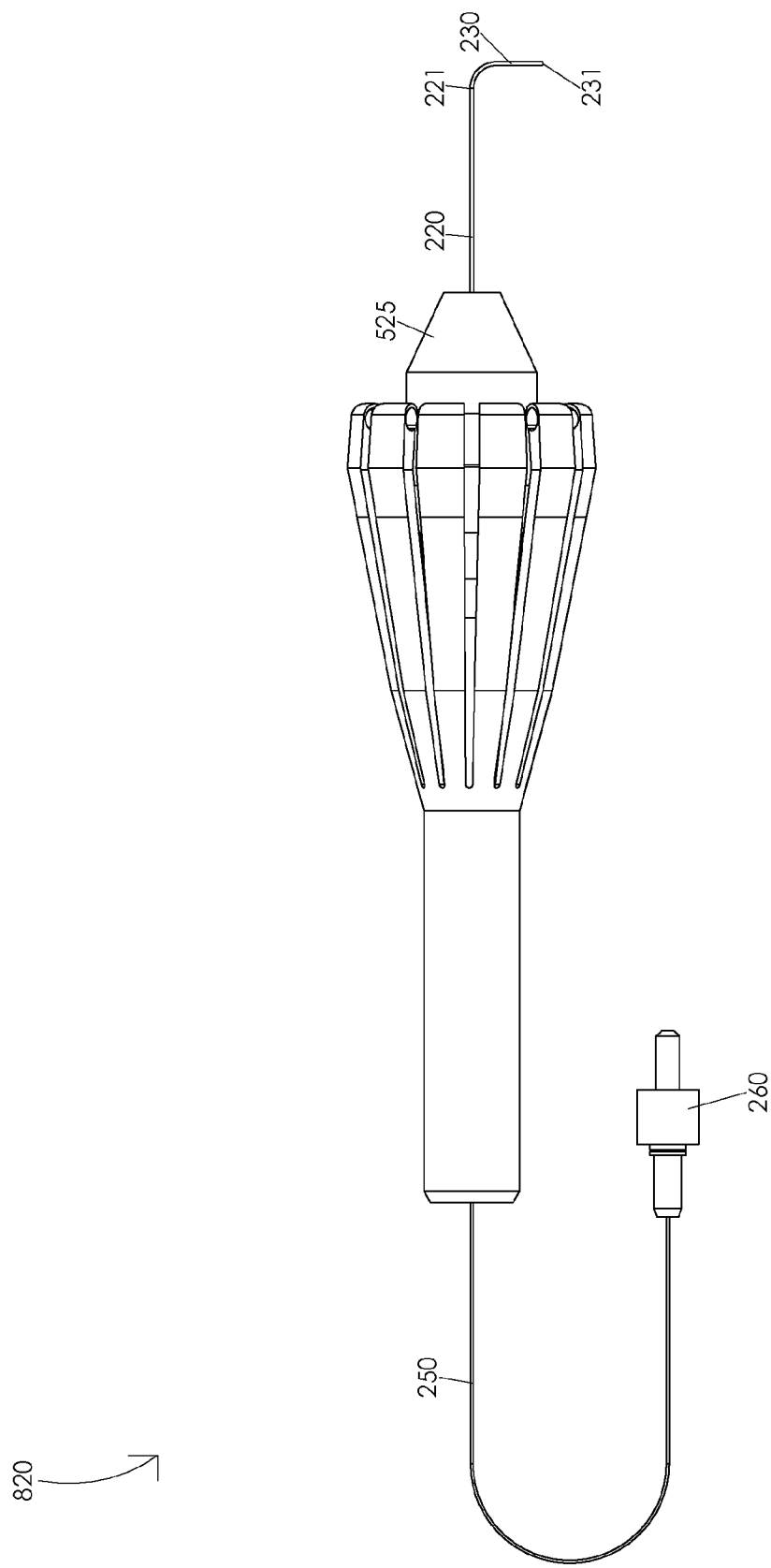

FIG. 8C illustrates an optic fiber in a second partially straightened position 820. In one or more embodiments, a compression of actuation structure 510 may be configured to gradually straighten optic fiber 250 from an optic fiber in a first partially straightened position 810 to an optic fiber in a second partially straightened position 820. Illustratively, a compression of actuation structure 510 may be configured to gradually retract wire 240 relative to housing tube 220. In one or more embodiments, a gradual retraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual retraction of wire 240 out of flexible tube 230, e.g., due to a compression of actuation structure 510, may be configured to gradually straighten flexible tube 230. In one or more embodiments, a gradual straightening of flexible tube 230 may be configured to gradually straighten optic fiber 250, e.g., from an optic fiber in a first partially straightened position 810 to an optic fiber in a second partially straightened position 820. Illustratively, a line tangent to optic fiber distal end 251 may intersect a line tangent to housing tube proximal end 202 at a second partially straightened angle, e.g., when optic fiber 250 comprises an optic fiber in a second partially straightened position 820. Illustratively, the second partially straightened angle may comprise any angle less than the first partially straightened angle. For example, the second partially straightened angle may comprise a 90 degree angle.

Figure 8D:
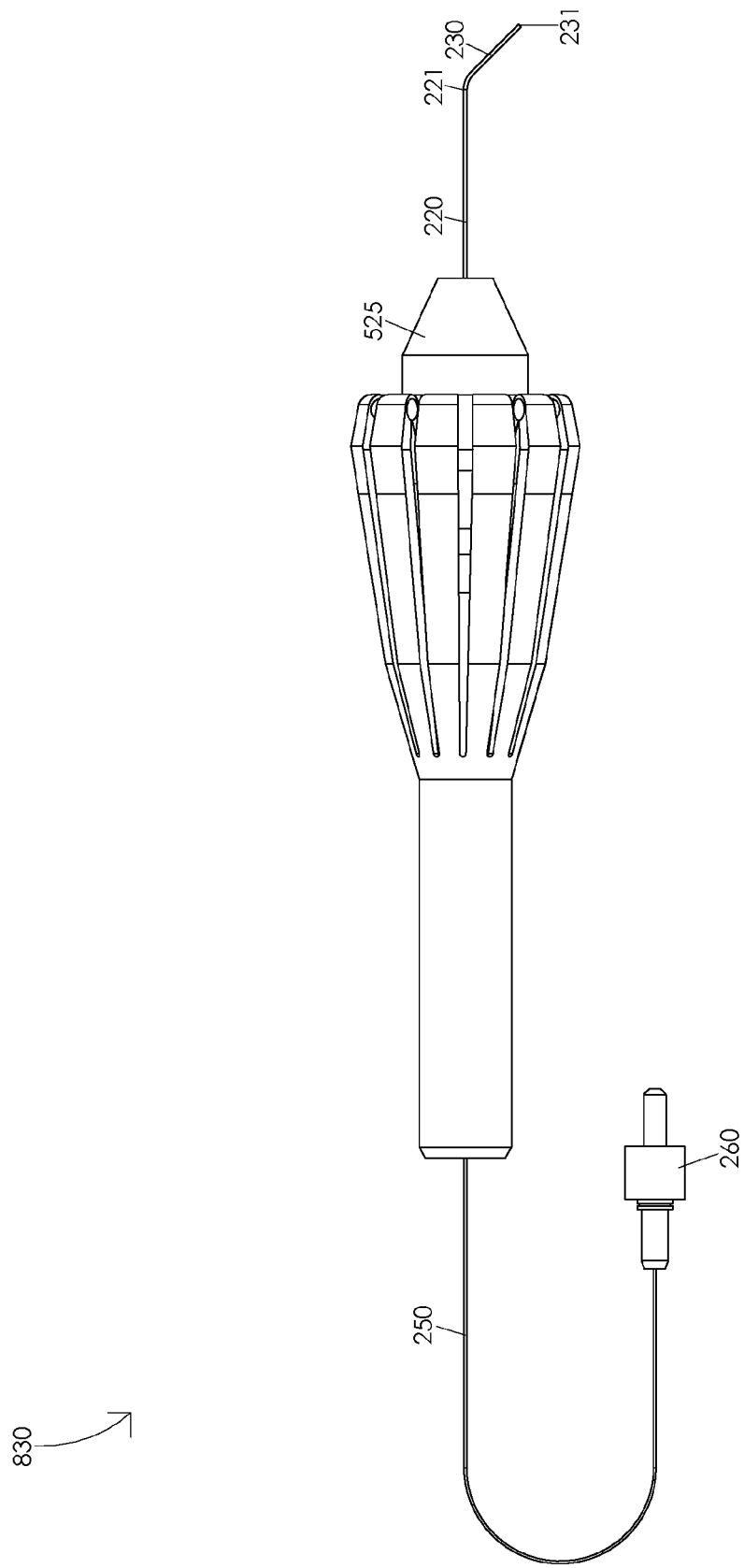

FIG. 8D illustrates an optic fiber in a third partially straightened position 830. In one or more embodiments, a compression of actuation structure 510 may be configured to gradually straighten optic fiber 250 from an optic fiber in a second partially straightened position 820 to an optic fiber in a third partially straightened position 830. Illustratively, a compression of actuation structure 510 may be configured to gradually retract wire 240 relative to housing tube 220. In one or more embodiments, a gradual retraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual refraction of wire 240 out of flexible tube 230, e.g., due to a compression of actuation structure 510, may be configured to gradually straighten flexible tube 230. In one or more embodiments, a gradual straightening of flexible tube 230 may be configured to gradually straighten optic fiber 250, e.g., from an optic fiber in a second partially straightened position 820 to an optic fiber in a third partially straightened position 830. Illustratively, a line tangent to optic fiber distal end 251 may intersect a line tangent to housing tube proximal end 202 at a third partially straightened angle, e.g., when optic fiber 250 comprises an optic fiber in a third partially straightened position 830. Illustratively, the third partially straightened angle may comprise any angle less than the second partially straightened angle. For example, the third partially straightened angle may comprise a 45 degree angle.

Figure 8E:
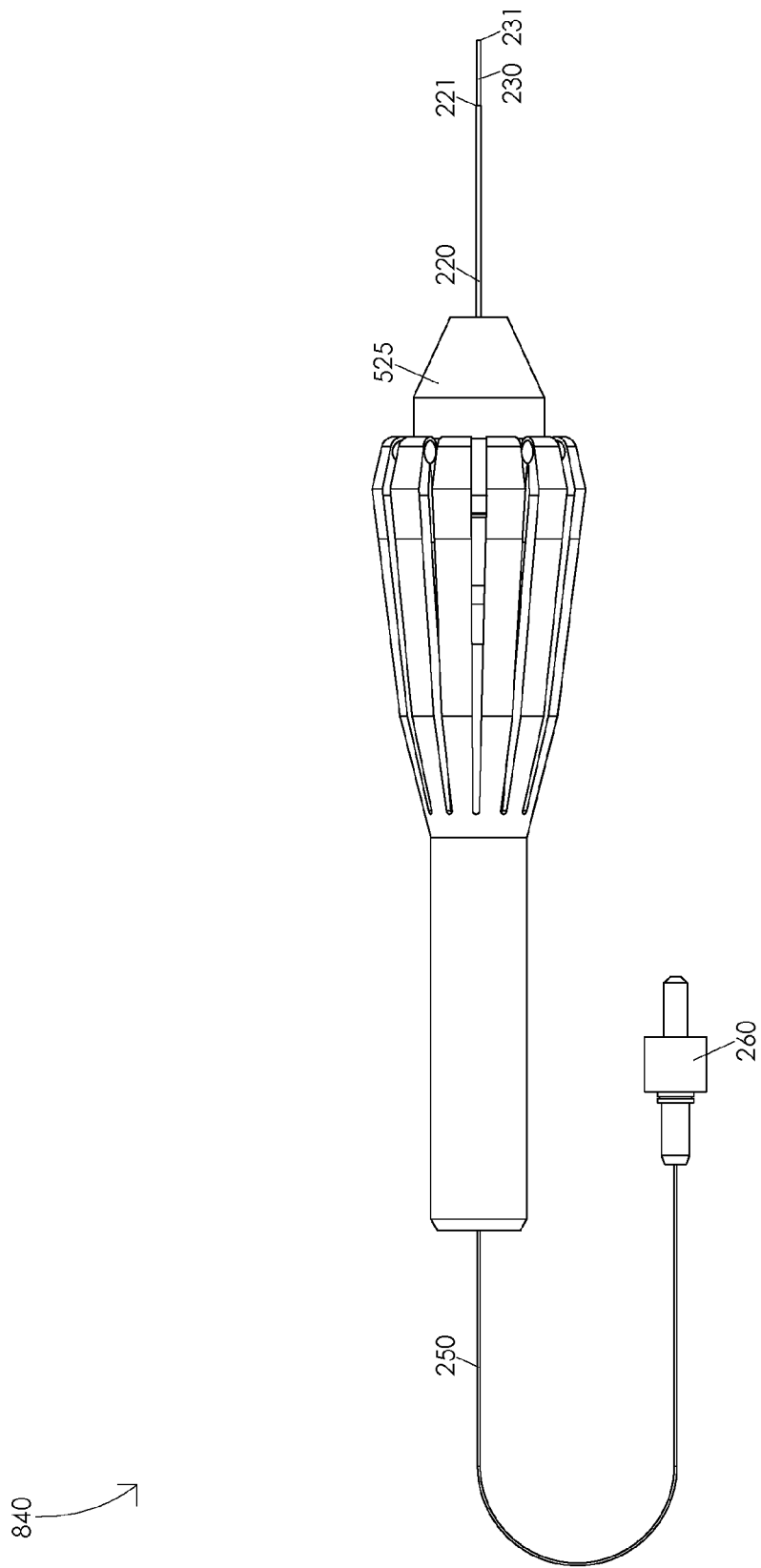

FIG. 8E illustrates an optic fiber in a fully straightened position 840. In one or more embodiments, a compression of actuation structure 510 may be configured to gradually straighten optic fiber 250 from an optic fiber in a third partially straightened position 830 to an optic fiber in a fully straightened position 840. Illustratively, a compression of actuation structure 510 may be configured to gradually retract wire 240 relative to housing tube 220. In one or more embodiments, a gradual retraction of wire 240 relative to housing tube 220 may be configured to gradually retract a portion of pre-formed curve 245 out of a portion of flexible tube 230, e.g., a portion of flexible tube 230 projecting out of housing tube distal end 221. Illustratively, a gradual refraction of wire 240 out of flexible tube 230, e.g., due to a compression of actuation structure 510, may be configured to gradually straighten flexible tube 230. In one or more embodiments, a gradual straightening of flexible tube 230 may be configured to gradually straighten optic fiber 250, e.g., from an optic fiber in a third partially straightened position 830 to an optic fiber in a fully straightened position 840. Illustratively, a line tangent to optic fiber distal end 251 may be parallel to a line tangent to housing tube proximal end 202, e.g., when optic fiber 250 comprises an optic fiber in a fully straightened position 840.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 500 to orient flexible tube 230 in an orientation configured to cause a curvature of flexible tube 230 within the particular transverse plane of the inner eye and varying an amount of decompression of actuation structure 510. Illustratively, a surgeon may aim optic fiber distal end 251 at any target within a particular sagittal plane of the inner eye by, e.g., rotating handle 500 to orient flexible tube 230 in an orientation configured to cause a curvature of flexible tube 230 within the particular sagittal plane of the inner eye and varying an amount of decompression of actuation structure 510. In one or more embodiments, a surgeon may aim optic fiber distal end 251 at any target within a particular frontal plane of the inner eye by, e.g., varying an amount of decompression of actuation structure 510 to orient a line tangent to optic fiber distal end 251 wherein the line tangent to optic fiber distal end 251 is within the particular frontal plane of the inner eye and rotating handle 500. Illustratively, a surgeon may aim optic fiber distal end 251 at any target located outside of the particular transverse plane, the particular sagittal plane, and the particular frontal plane of the inner eye, e.g., by varying a rotational orientation of handle 500 and varying an amount of decompression of actuation structure 510. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 9A and 9B are schematic diagrams illustrating a handle 900. FIG. 9A illustrates a top view of handle 900. Illustratively, handle 900 may comprise a handle distal end 901, a handle proximal end 902, a handle base 910, an actuation structure 920 having an actuation structure distal end 921 and an actuation structure proximal end 922, and an actuation ring 930. In one or more embodiments, actuation structure 920 may comprise a plurality of actuation arms 925. Illustratively, each actuation arm 925 may comprise at least one extension mechanism 926. In one or more embodiments, actuation structure 920 may comprise a shape memory material configured to project actuation structure distal end 921 a first distance from actuation structure proximal end 922, e.g., when actuation structure 920 is fully decompressed. Illustratively, actuation structure 920 may comprise a shape memory material configured to project actuation structure distal end 921 a second distance from actuation structure proximal end 922, e.g., when actuation structure 920 is fully compressed. In one or more embodiments, the second distance from actuation structure proximal end 922 may be greater than the first distance from actuation structure proximal end 922. Actuation structure 920 may be manufactured from any suitable material, e.g., polymers, metals, metal alloys, etc., or from any combination of suitable materials.

Illustratively, actuation structure 920 may be compressed by an application of a compressive force to actuation structure 920. In one or more embodiments, actuation structure 920 may be compressed by an application of one or more compressive forces located at one or more locations around an outer perimeter of actuation structure 920. Illustratively, the one or more locations may comprise any of a plurality of locations around the outer perimeter of actuation structure 920. For example, a surgeon may compress actuation structure 920, e.g., by squeezing actuation structure 920. Illustratively, the surgeon may compress actuation structure 920 by squeezing actuation structure 920 at any particular location of a plurality of locations around an outer perimeter of actuation structure 920. For example, a surgeon may rotate handle 900 and compress actuation structure 920 from any rotational position of a plurality of rotational positions of handle 900.

In one or more embodiments, actuation structure 920 may be compressed by an application of a compressive force to any one or more of the plurality of actuation arms 925. Illustratively, each actuation arm 925 may be configured to actuate independently. In one or more embodiments, each actuation arm 925 may be connected to one or more of the plurality of actuation arms 925 wherein an actuation of a particular actuation arm 925 may be configured to actuate every actuation arm 925 of the plurality of actuation arms 925. Illustratively, one or more actuation arms 925 may be configured to actuate in pairs or groups. For example, an actuation of a first actuation arm 925 may be configured to actuate a second actuation arm 925.

In one or more embodiments, a compression of actuation structure 920, e.g., due to an application of a compressive force to a particular actuation arm 925, may be configured to actuate the particular actuation arm 925. Illustratively, an actuation of the particular actuation arm 925 may be configured to actuate every actuation arm 925 of the plurality of actuation arms 925. In one or more embodiments, an application of a compressive force to a particular actuation arm 925 may be configured to extend at least one extension mechanism 926 of the particular actuation arm 925. Illustratively, a particular actuation arm 925 may be configured to extend a first length from handle base 910. In one or more embodiments, an extension of an extension mechanism 926 of the particular actuation arm 925, e.g., due to an application of a compressive force to the particular actuation arm 925, may be configured to extend the particular actuation arm 925 a second length from handle base 910. Illustratively, the second length from handle base 910 may be greater than the first length from handle base 910.

In one or more embodiments, actuation ring 930 may be fixed to actuation structure distal end 921. Illustratively, a compression of actuation structure 920 may be configured to gradually extend actuation ring 930 from handle base 910. For example, actuation ring 930 may be configured to extend a first distance from actuation structure proximal end 922, e.g., when actuation structure 920 is fully decompressed. In one or more embodiments, actuation ring 930 may be configured to extend a second distance from actuation structure proximal end 922, e.g., due to a compression of actuation structure 920. Illustratively, the second distance from actuation structure proximal end 922 may be greater than the first distance from actuation structure proximal end 922.

FIG. 9B illustrates a cross-sectional view of handle 900. In one or more embodiments, handle 900 may comprise a wire fixation mechanism housing 940, an inner bore 960, an inner bore proximal taper 961, an inner bore distal chamber 962, an optic fiber guide 963, and a wire proximal end housing 964. Handle 900 may be manufactured from any suitable material, e.g., polymers, metals, metal alloys, etc., or from any combination of suitable materials.

Figure 10:
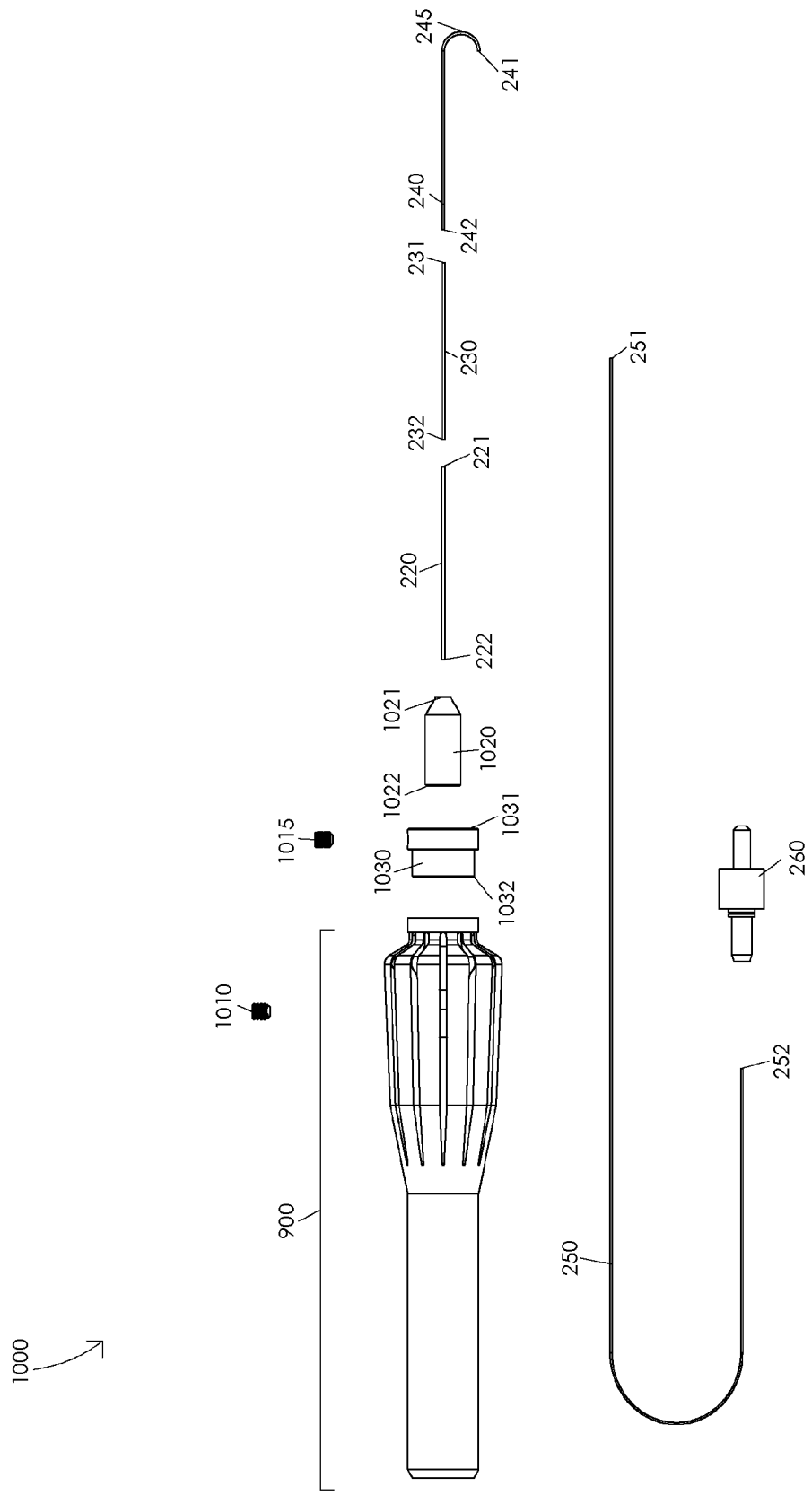
FIG. 10 is a schematic diagram illustrating an exploded view of a steerable laser probe assembly.

FIG. 10 is a schematic diagram illustrating an exploded view of a steerable laser probe assembly 1000. In one or more embodiments, steerable laser probe assembly 1000 may comprise a handle 900; a wire fixation mechanism 1010; a nosecone fixation mechanism 1015; an inner nosecone 1020 having an inner nosecone distal end 1021 and an inner nosecone proximal end 1022; an outer nosecone 1030 having an outer nosecone distal end 1031 and an outer nosecone proximal end 1032; a housing tube 220 having a housing tube distal end 221 and a housing tube proximal end 222; a flexible tube 230 having a flexible tube distal end 231 and a flexible tube proximal end 232; a wire 240 having a wire distal end 241, a wire proximal end 242, and a pre-formed curve 245; an optic fiber 250 having an optic fiber distal end 251 and an optic fiber proximal end 252; and a light source interface 260. Illustratively, light source interface 260 may be configured to interface with optic fiber 250, e.g., at optic fiber proximal end 252. In one or more embodiments, light source interface 260 may comprise a standard light source connector, e.g., an SMA connector.

Illustratively, inner nosecone 1020 may be fixed to outer nosecone 1030, e.g., inner nosecone proximal end 1022 may be fixed to outer nosecone distal end 1031. In one or more embodiments, a portion of inner nosecone 1020 may be disposed within a portion of outer nosecone 1030, e.g., inner nosecone proximal end 1022 may be disposed within outer nosecone 1030. Illustratively, a portion of inner nosecone 1020 may be disposed within a portion of outer nosecone 1030 wherein inner nosecone 1020 is fixed to outer nosecone 1030. In one or more embodiments, inner nosecone 1020 may be fixed to outer nosecone 1030, e.g., by an adhesive or any other suitable fixation means. Illustratively, nosecone fixation mechanism 1015 may be configured to fix inner nosecone 1020 to outer nosecone 1030. For example, nosecone fixation mechanism 1015 may comprise a set screw configured to firmly attach inner nosecone 1020 to outer nosecone 1030. In one or more embodiments, inner nosecone 1020 and outer nosecone 1030 may be manufactured as a single unit. Inner nosecone 1020 and outer nosecone 1030 may be manufactured from any suitable material, e.g., polymers, metals, metal alloys, etc., or from any combination of suitable materials.

Illustratively, outer nosecone 1030 may be fixed to actuation structure 920, e.g., outer nosecone proximal end 1032 may be fixed to handle distal end 901. In one or more embodiments, a portion of outer nosecone 1030 may be disposed within actuation ring 930, e.g., outer nosecone proximal end 1032 may be disposed within actuation ring 930. Illustratively, a portion of outer nosecone 1030 may be disposed within actuation ring 930 wherein outer nosecone 1030 is fixed to actuation ring 930. In one or more embodiments, outer nosecone 1030 may be fixed to actuation structure 920, e.g., by an adhesive or any other suitable fixation means.

Illustratively, housing tube 220 may be fixed to inner nosecone 1020, e.g., housing tube proximal end 222 may be fixed to inner nosecone distal end 1021. In one or more embodiments, housing tube 220 may be fixed to inner nosecone 1020, e.g., by an adhesive or by any other suitable fixation means. Illustratively, a portion of housing tube 220 may be disposed within a portion of inner nosecone 1020, e.g., housing tube proximal end 222 may be disposed within inner nosecone 1020. In one or more embodiments, a portion of housing tube 220 may be fixed within inner nosecone 1020, e.g., by an adhesive or other any suitable fixation means. Housing tube 220 may be manufactured from any suitable material, e.g., polymers, metals, metal alloys, etc., or from any combination of suitable materials.

In one or more embodiments, a portion of flexible tube 230 may be disposed within housing tube 220, e.g., flexible tube proximal end 232 may be disposed within housing tube 220. Illustratively, a portion of flexible tube 230 may extend from housing tube 220, e.g., flexible tube distal end 231 may extend from housing tube distal end 221. In one or more embodiments, a portion of flexible tube 230 may be fixed within housing tube 220, e.g., by an adhesive or any other suitable fixation means. Illustratively, a portion of flexible tube 230 may be disposed within a portion of housing tube 220. In one or more embodiments, a portion of flexible tube 230 may be disposed within inner nosecone 1020, e.g., flexible tube proximal end 232 may be disposed within inner nosecone 1020. Illustratively, a portion of flexible tube 230 may be fixed within inner nosecone 1020, e.g., by an adhesive or any other suitable fixation means. Flexible tube 230 may be manufactured from any suitable material, e.g., polymers, metals, metal alloys, etc., or from any combination of suitable materials.

Illustratively, optic fiber 250 may be disposed within inner bore 960, optic fiber guide 963, inner bore distal chamber 962, housing tube 220, and flexible tube 230. In one or more embodiments, optic fiber 250 may be disposed within flexible tube 230 wherein optic fiber distal end 251 may be adjacent to flexible tube distal end 231. Illustratively, a portion of optic fiber 250 may be fixed to an inner portion of flexible tube 230, e.g., by an adhesive or any other suitable fixation means. In one or more embodiments, a portion of optic fiber 250 may be fixed to an inner portion of housing tube 220, e.g., by an adhesive or any other suitable fixation means. Illustratively, optic fiber 250 may be configured to transmit light, e.g., light from a light source.

In one or more embodiments, a portion of wire 240 may comprise a shape memory material, e.g., Nitinol. Illustratively, pre-formed curve 245 may comprise a shape memory material, e.g., Nitinol. In one or more embodiments, wire 240 may be disposed within wire proximal end housing 964, inner bore distal chamber 962, and housing tube 220. Illustratively, a portion of wire 240 may be disposed within flexible tube 230. In one or more embodiments, wire fixation mechanism 1010 may be disposed within wire fixation mechanism housing 940. For example, a portion of wire fixation mechanism 1010 may be disposed within wire proximal end housing 964. Illustratively, wire fixation mechanism 1010 may be configured to fix a portion of wire 240, e.g., wire proximal end 242, in a position relative to handle 900. In one or more embodiments, wire fixation mechanism 1010 may comprise a set screw configured to fix wire 240 in a position relative to handle 900, e.g., by a press fit or any other suitable fixation means. Illustratively, a portion of wire 240, e.g., wire proximal end 242, may be fixed to wire fixation mechanism 1010, e.g., by an adhesive or any other suitable fixation means. Wire 240 may be manufactured from any suitable material, e.g., polymers, metals, metal alloys, etc., or from any combination of suitable materials.

In one or more embodiments, a compression of actuation structure 920 may be configured to extend actuation ring 930 relative to handle base 910. Illustratively, an extension of actuation ring 930 relative to handle base 910 may be configured to extend outer nosecone 1030, inner nosecone 1020, housing tube 220, and flexible tube 230 relative to handle base 910. In one or more embodiments, a compression of actuation structure 920 may be configured to actuate housing tube 220 relative to wire 240. Illustratively, a compression of actuation structure 920 may be configured to extend housing tube 220 relative to wire 240. In one or more embodiments, an extension of housing tube 220 relative to wire 240 may be configured to extend housing tube 220 over a portion of pre-formed curve 245. Illustratively, an extension of housing tube 220 over a portion of pre-formed curve 245 may be configured to generally straighten a portion of pre-formed curve 245.

In one or more embodiments, a portion of pre-formed curve 245 may be disposed within a portion of flexible tube 230, e.g., a portion of flexible tube 230 projecting from housing tube distal end 221, and flexible tube 230 may be curved by the portion of pre-formed curve 245 disposed within flexible tube 230. Illustratively, an extension of housing tube 220 relative to wire 240, e.g., due to a compression of actuation structure 920, may be configured to generally straighten a portion of pre-formed curve 245. In one or more embodiments, a general straightening of a portion of pre-formed curve 245 may be configured to straighten flexible tube 230. Illustratively, a straightening of flexible tube 230 may be configured to straighten optic fiber 250.

In one or more embodiments, a decompression of actuation structure 920 may be configured to retract actuation ring 930 relative to handle base 910. Illustratively, a retraction of actuation ring 930 relative to handle base 910 may be configured to retract outer nosecone 1030, inner nosecone 1020, housing tube 220, and flexible tube 230 relative to handle base 910. In one or more embodiments, a decompression of actuation structure 920 may be configured to actuate housing tube 220 relative to wire 240. Illustratively, a decompression of actuation structure 920 may be configured to retract housing tube 220 relative to wire 240. In one or more embodiments, a retraction of housing tube 220 relative to wire 240 may be configured to retract housing tube 220 relative to a portion of pre-formed curve 245. For example, a retraction of housing tube 220 may be configured to expose a portion of pre-formed curve 245, e.g., a generally straightened portion of pre-formed curve 245, at housing tube distal end 221. Illustratively, a refraction of housing tube 220 relative to a generally straightened portion of pre-formed curve 245 may be configured to gradually expose the generally straightened portion of pre-formed curve 245 at housing tube distal end 221 causing the generally straightened portion of pre-formed curve 245 to gradually curve.

In one or more embodiments, a portion of pre-formed curve 245 may disposed within housing tube 220 and the portion of pre-formed curve 245 may be generally straightened by housing tube 220. Illustratively, a retraction of housing tube 220 relative to wire 240, e.g., due to a decompression of actuation structure 920, may be configured to gradually curve the portion of pre-formed curve 245, e.g., as the portion of pre-formed curved 245 is exposed by housing tube 220. In one or more embodiments, a gradual curving of a portion of pre-formed curve 245 may be configured to gradually curve flexible tube 230. Illustratively, a gradual curving of flexible tube 230 may be configured to gradually curve optic fiber 250.

Figure 11A:
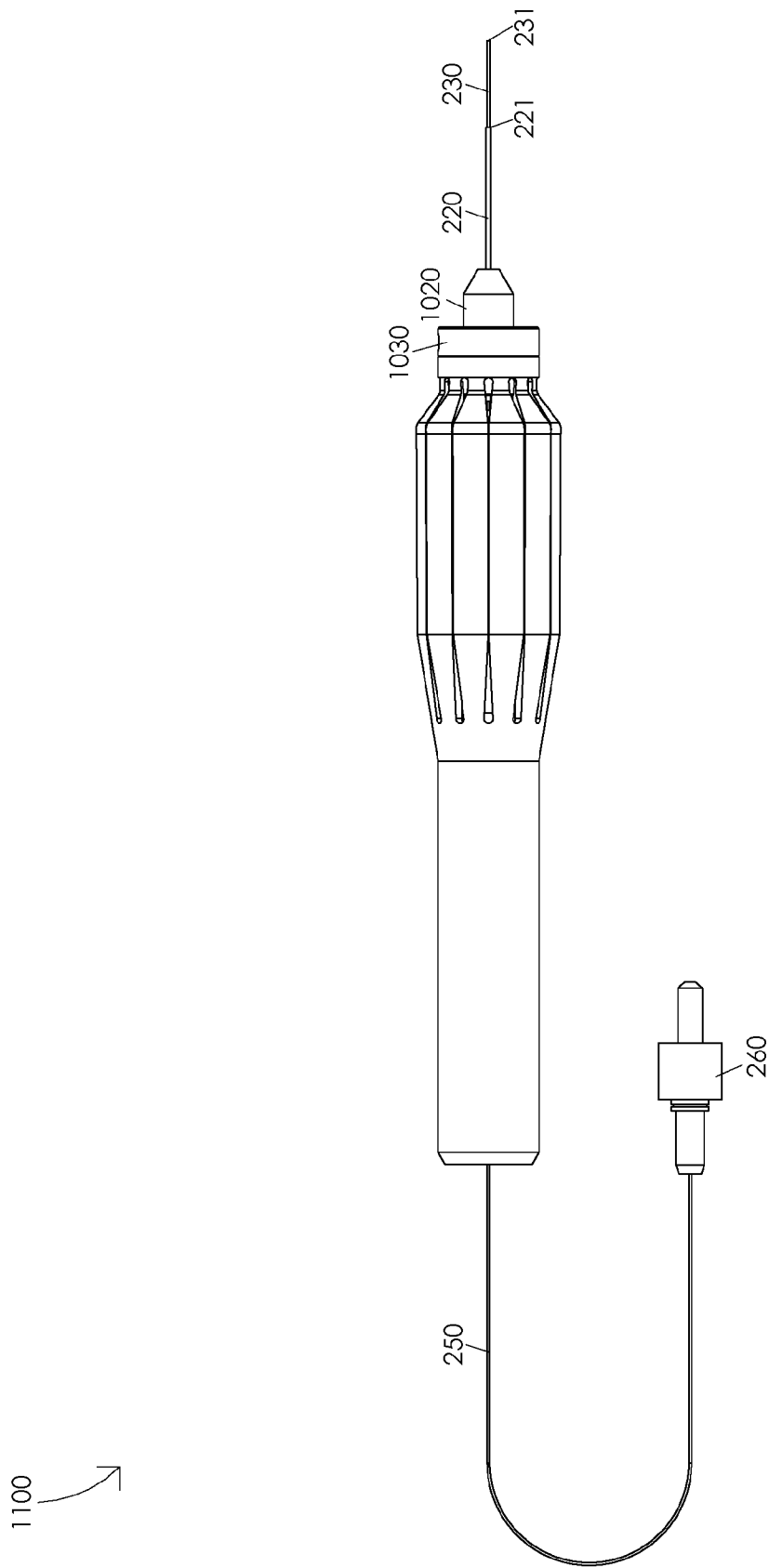
FIGS. 11A, 11B, 11C, 11D, and 11E illustrate a gradual curving of an optic fiber.

FIGS. 11A, 11B, 11C, 11D, and 11E illustrate a gradual curving of an optic fiber 250. FIG. 11A illustrates a straight optic fiber 1100. In one or more embodiments, optic fiber 250 may comprise a straight optic fiber 1100, e.g., when actuation ring 930 is fully extended relative to handle base 910. Illustratively, optic fiber 250 may comprise a straight optic fiber 1100, e.g., when actuation structure 920 is fully compressed. In one or more embodiments, optic fiber 250 may comprise a straight optic fiber 1100, e.g., when housing tube 220 is fully extended relative to wire 240. For example, optic fiber 250 may comprise a straight optic fiber 1100 when pre-formed curve 245 is fully contained within housing tube 220. Illustratively, a line tangent to optic fiber distal end 251 may be parallel to a line tangent to housing tube proximal end 202, e.g., when optic fiber 250 comprises a straight optic fiber 1100.

Figure 11B:
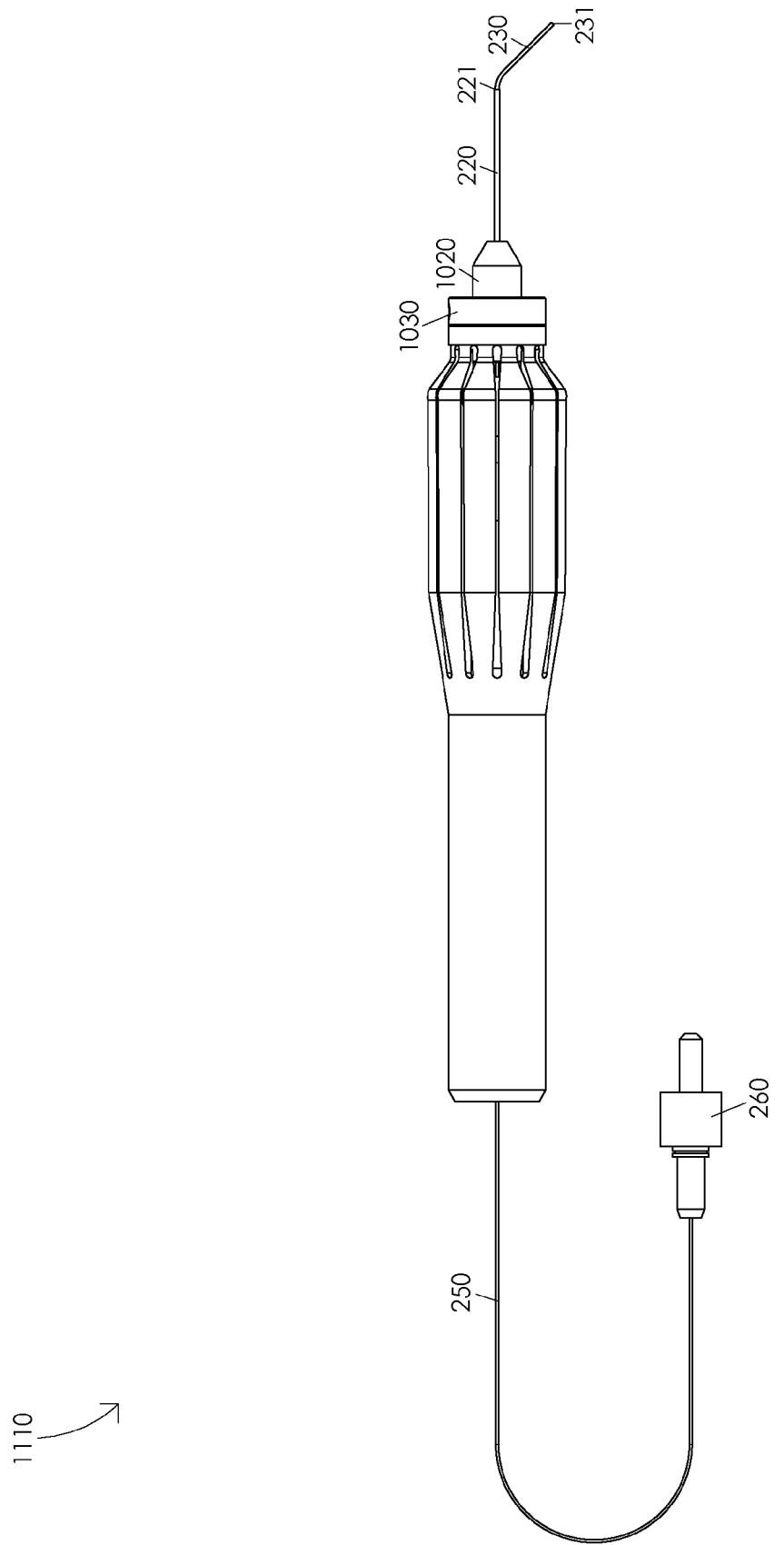

FIG. 11B illustrates an optic fiber in a first curved position 1110. In one or more embodiments, a decompression of actuation structure 920 may be configured to gradually curve optic fiber 250 from a straight optic fiber 1100 to an optic fiber in a first curved position 1110. Illustratively, a decompression of actuation structure 920 may be configured to gradually retract housing tube 220 relative to wire 240. In one or more embodiments, a gradual retraction of housing tube 220 relative to wire 240 may be configured to gradually expose a portion of pre-formed curve 245 at housing tube distal end 221 causing the portion of pre-formed curve 245 to gradually curve. Illustratively, a gradual curving of a portion of pre-formed curve 245, e.g., due to a decompression of actuation structure 920, may be configured to gradually curve flexible tube 230. In one or more embodiments, a gradual curving of flexible tube 230 may be configured to gradually curve optic fiber 250, e.g., from a straight optic fiber 1100 to an optic fiber in a first curved position 1110. Illustratively, a line tangent to optic fiber distal end 251 may intersect a line tangent to housing tube proximal end 202 at a first angle, e.g., when optic fiber 250 comprises an optic fiber in a first curved position 1110. In one or more embodiments, the first angle may comprise any angle greater than zero degrees. For example, the first angle may comprise a 45 degree angle.

Figure 11C:
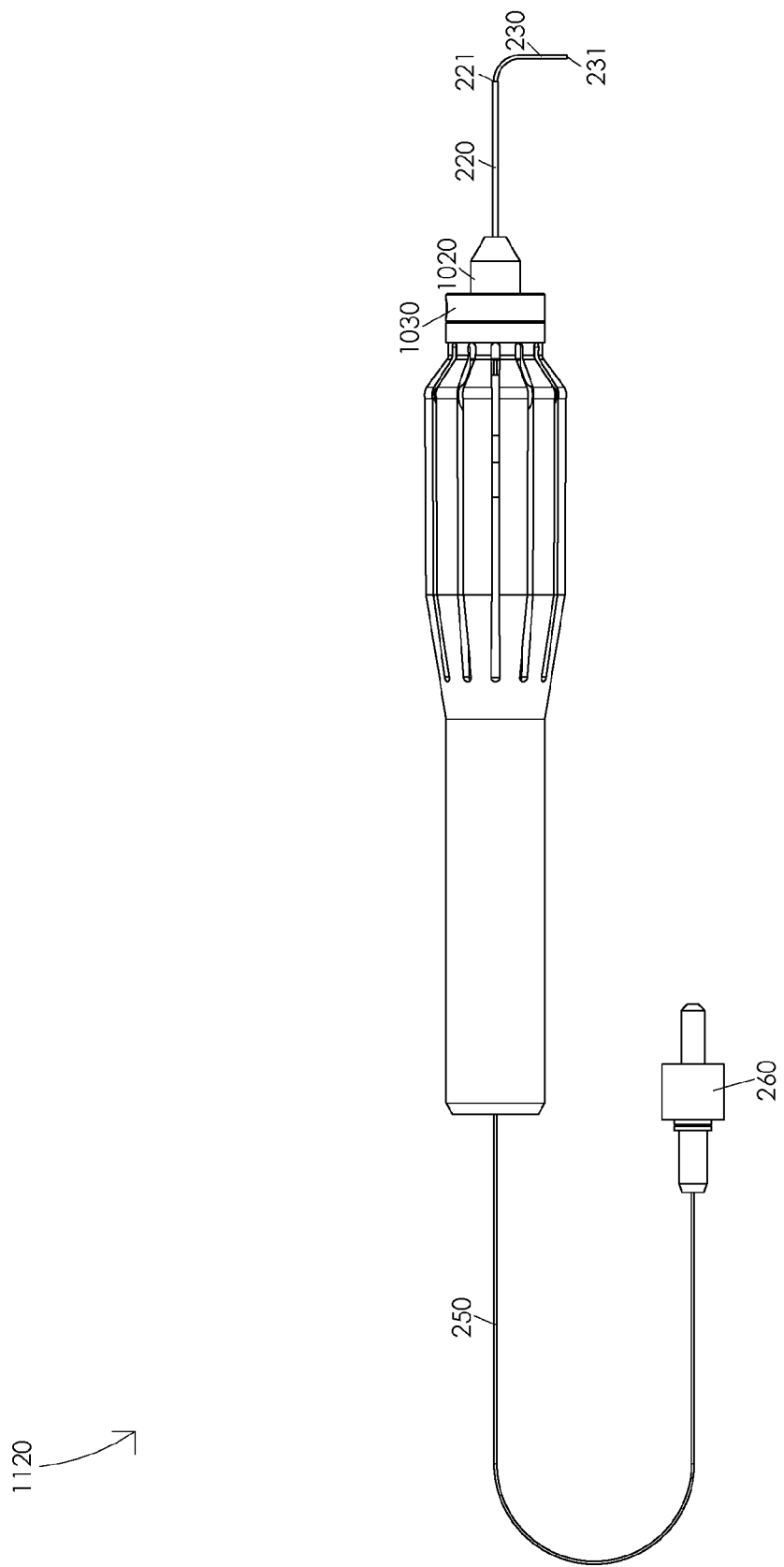

FIG. 11C illustrates an optic fiber in a second curved position 1120. In one or more embodiments, a decompression of actuation structure 920 may be configured to gradually curve optic fiber 250 from an optic fiber in a first curved position 1110 to an optic fiber in a second curved position 1120. Illustratively, a decompression of actuation structure 920 may be configured to gradually retract housing tube 220 relative to wire 240. In one or more embodiments, a gradual retraction of housing tube 220 relative to wire 240 may be configured to gradually expose a portion of pre-formed curve 245 at housing tube distal end 221 causing the portion of pre-formed curve 245 to gradually curve. Illustratively, a gradual curving of a portion of pre-formed curve 245, e.g., due to a decompression of actuation structure 920, may be configured to gradually curve flexible tube 230. In one or more embodiments, a gradual curving of flexible tube 230 may be configured to gradually curve optic fiber 250, e.g., from an optic fiber in a first curved position 1110 to an optic fiber in a second curved position 1120. Illustratively, a line tangent to optic fiber distal end 251 may intersect a line tangent to housing tube proximal end 202 at a second angle, e.g., when optic fiber 250 comprises an optic fiber in a second curved position 1120. In one or more embodiments, the second angle may comprise any angle greater than the first angle. For example, the second angle may comprise a 90 degree angle.

Figure 11D:
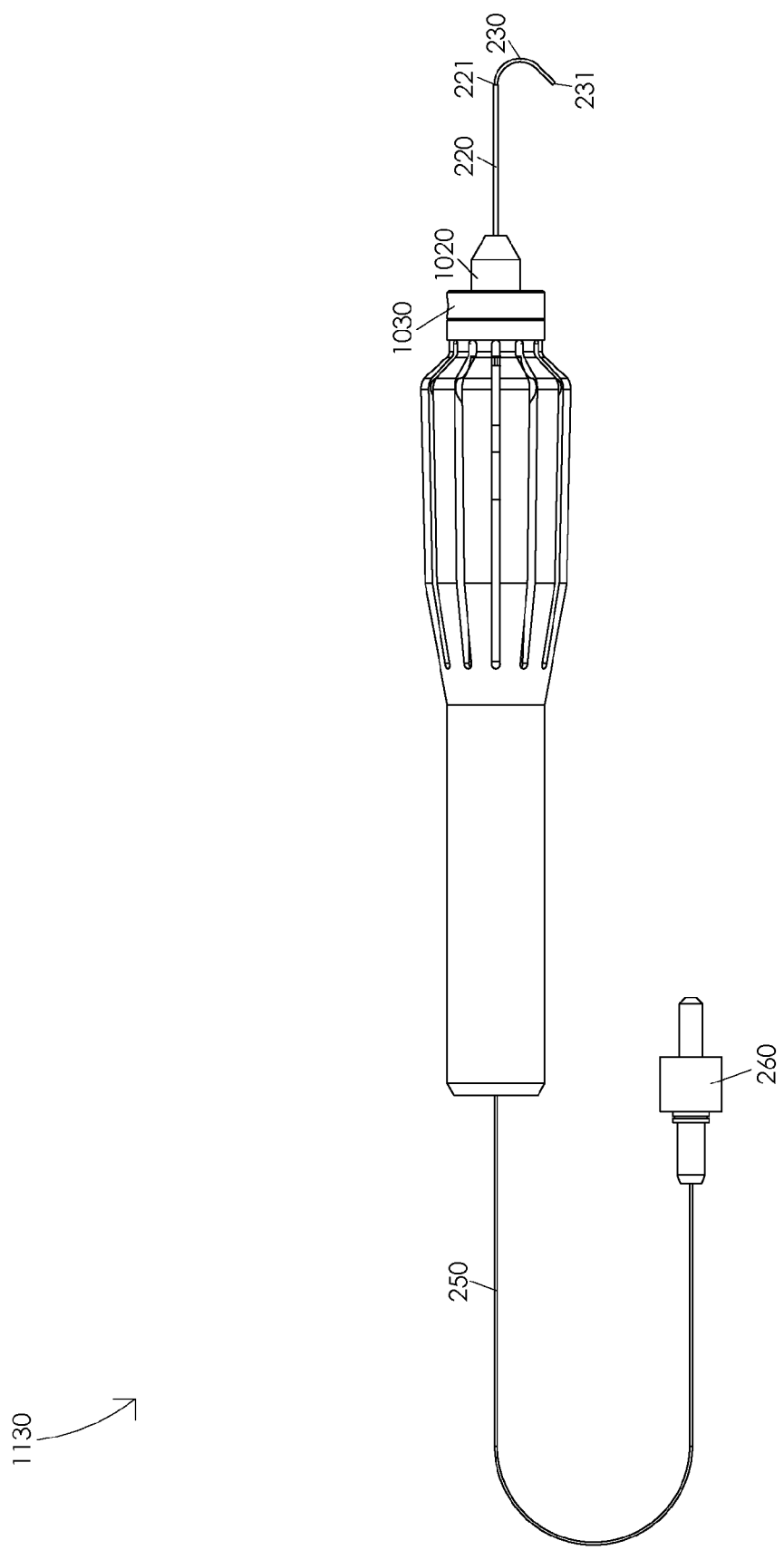

FIG. 11D illustrates an optic fiber in a third curved position 1130. In one or more embodiments, a decompression of actuation structure 920 may be configured to gradually curve optic fiber 250 from an optic fiber in a second curved position 1120 to an optic fiber in a third curved position 1130. Illustratively, a decompression of actuation structure 920 may be configured to gradually retract housing tube 220 relative to wire 240. In one or more embodiments, a gradual retraction of housing tube 220 relative to wire 240 may be configured to gradually expose a portion of pre-formed curve 245 at housing tube distal end 221 causing the portion of pre-formed curve 245 to gradually curve. Illustratively, a gradual curving of a portion of pre-formed curve 245, e.g., due to a decompression of actuation structure 920, may be configured to gradually curve flexible tube 230. In one or more embodiments, a gradual curving of flexible tube 230 may be configured to gradually curve optic fiber 250, e.g., from an optic fiber in a second curved position 1120 to an optic fiber in a third curved position 1130. Illustratively, a line tangent to optic fiber distal end 251 may intersect a line tangent to housing tube proximal end 202 at a third angle, e.g., when optic fiber 250 comprises an optic fiber in a third curved position 1130. In one or more embodiments, the third angle may comprise any angle greater than the second angle. For example, the third angle may comprise a 135 degree angle.

Figure 11E:
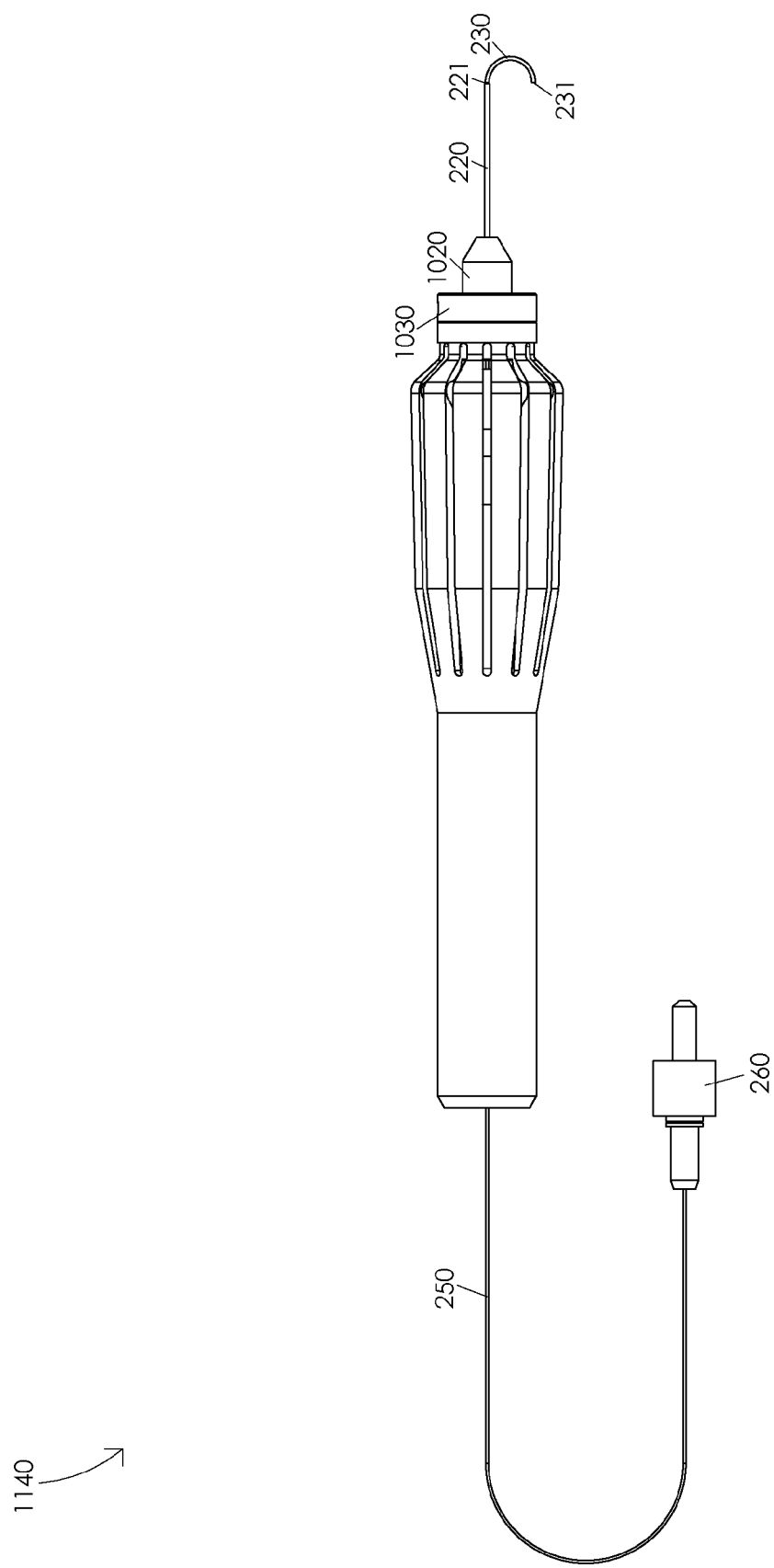

FIG. 11E illustrates an optic fiber in a fourth curved position 1140. In one or more embodiments, a decompression of actuation structure 920 may be configured to gradually curve optic fiber 250 from an optic fiber in a third curved position 1130 to an optic fiber in a fourth curved position 1140. Illustratively, a decompression of actuation structure 920 may be configured to gradually retract housing tube 220 relative to wire 240. In one or more embodiments, a gradual retraction of housing tube 220 relative to wire 240 may be configured to gradually expose a portion of pre-formed curve 245 at housing tube distal end 221 causing the portion of pre-formed curve 245 to gradually curve. Illustratively, a gradual curving of a portion of pre-formed curve 245, e.g., due to a decompression of actuation structure 920, may be configured to gradually curve flexible tube 230. In one or more embodiments, a gradual curving of flexible tube 230 may be configured to gradually curve optic fiber 250, e.g., from an optic fiber in a third curved position 1130 to an optic fiber in a fourth curved position 1140. Illustratively, a line tangent to optic fiber distal end 251 may be parallel to a line tangent to housing tube proxies mal end 202, e.g., when optic fiber 250 comprises an optic fiber in a fourth curved position 1140.

In one or more embodiments, one or more properties of a steerable laser probe may be adjusted to attain one or more desired steerable laser probe features. Illustratively, one or more steerable laser probe components may be manufactured as a single component. In one or more embodiments, housing tube 220 and flexible tube 230 may be manufactured as a single unit. Illustratively, a length that housing tube 220 extends from inner nosecone 1020 or a length that flexible tube 230 extends from housing tube distal end 221 may be adjusted to vary an amount of decompression of actuation structure 920 configured to curve flexible tube 230 to a particular curved position. In one or more embodiments, a stiffness of flexible tube 230 may be adjusted to vary an amount of decompression of actuation structure 920 configured to curve flexible tube 230 to a particular curved position. Illustratively, a stiffness of wire 240 may be adjusted to vary an amount of decompression of actuation structure 920 configured to curve flexible tube 230 to a particular curved position. In one or more embodiments, a geometry of actuation structure 920 may be adjusted to vary an amount of decompression of actuation structure 920 configured to curve flexible tube 230 to a particular curved position. Illustratively, a geometry of pre-formed curve 245 may be adjusted to vary an amount of decompression of actuation structure 920 configured to curve flexible tube 230 to a particular curved position. For example, a length of wire 240 may be adjusted to vary an amount of decompression of actuation structure 920 configured to curve flexible tube 230 to a particular curved position. In one or more embodiments, a portion of optic fiber 250 may be enclosed in an optic fiber sleeve configured to, e.g., protect optic fiber 250, vary a stiffness of optic fiber 250, vary an optical property of optic fiber 250, etc.

Figure 12A:
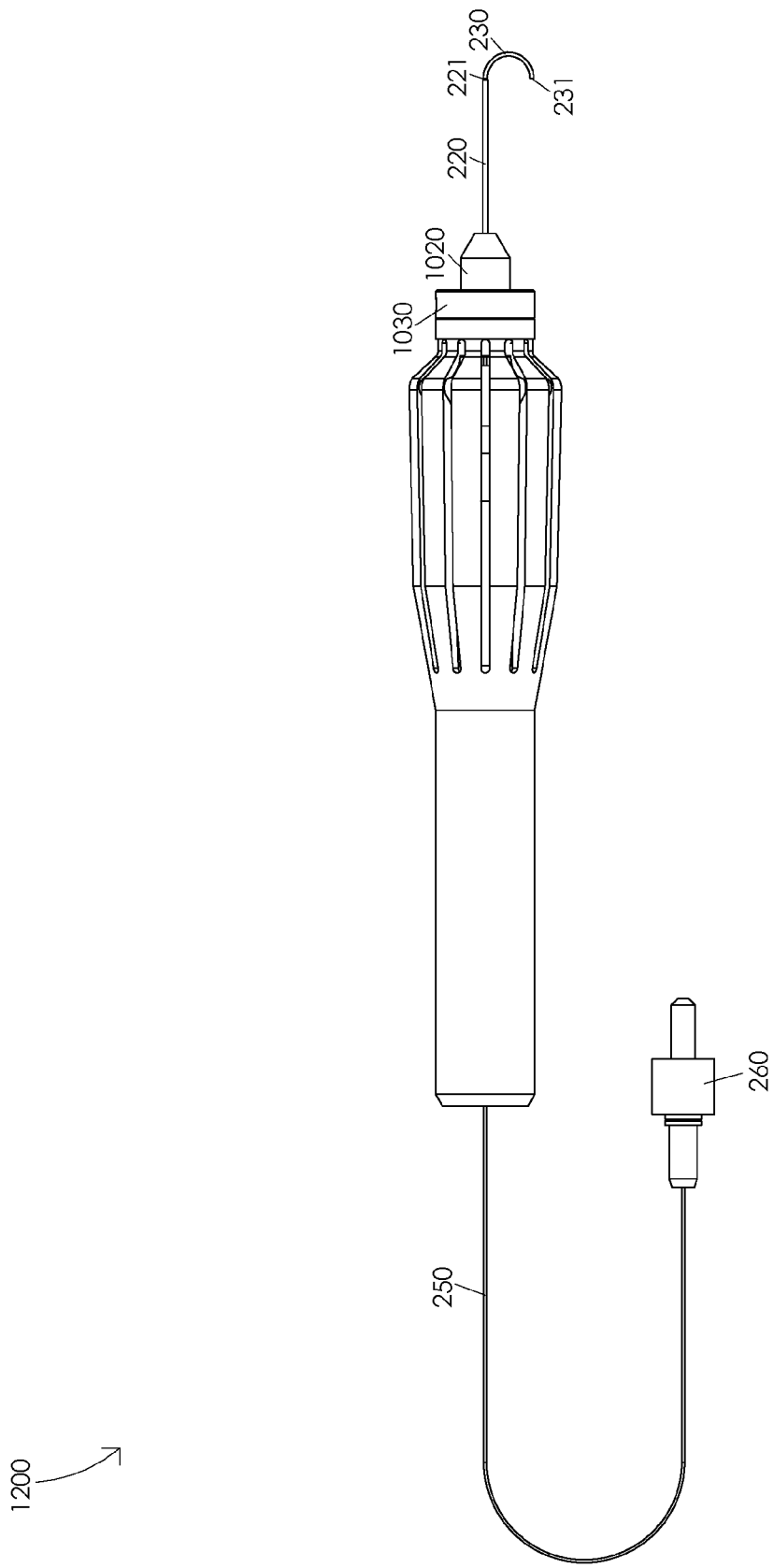
FIGS. 12A, 12B, 12C, 12D, and 12E illustrate a gradual straightening of an optic fiber.

FIGS. 12A, 12B, 12C, 12D, and 12E illustrate a gradual straightening of an optic fiber 250. FIG. 12A illustrates a fully curved optic fiber 1200. In one or more embodiments, optic fiber 250 may comprise a fully curved optic fiber 1200, e.g., when actuation ring 930 is fully refracted relative to handle base 910. Illustratively, optic fiber 250 may comprise a fully curved optic fiber 1200, e.g., when actuation structure 920 is fully decompressed. In one or more embodiments, optic fiber 250 may comprise a fully curved optic fiber 1200, e.g., when housing tube 220 is fully retracted relative to wire 240. For example, optic fiber 250 may comprise a fully curved optic fiber 1200 when pre-formed curve 245 is fully contained within flexible tube 230. Illustratively, a line tangent to optic fiber distal end 251 may be parallel to a line tangent to housing tube proximal end 202, e.g., when optic fiber 250 comprises a fully curved optic fiber 1200.

Figure 12B:
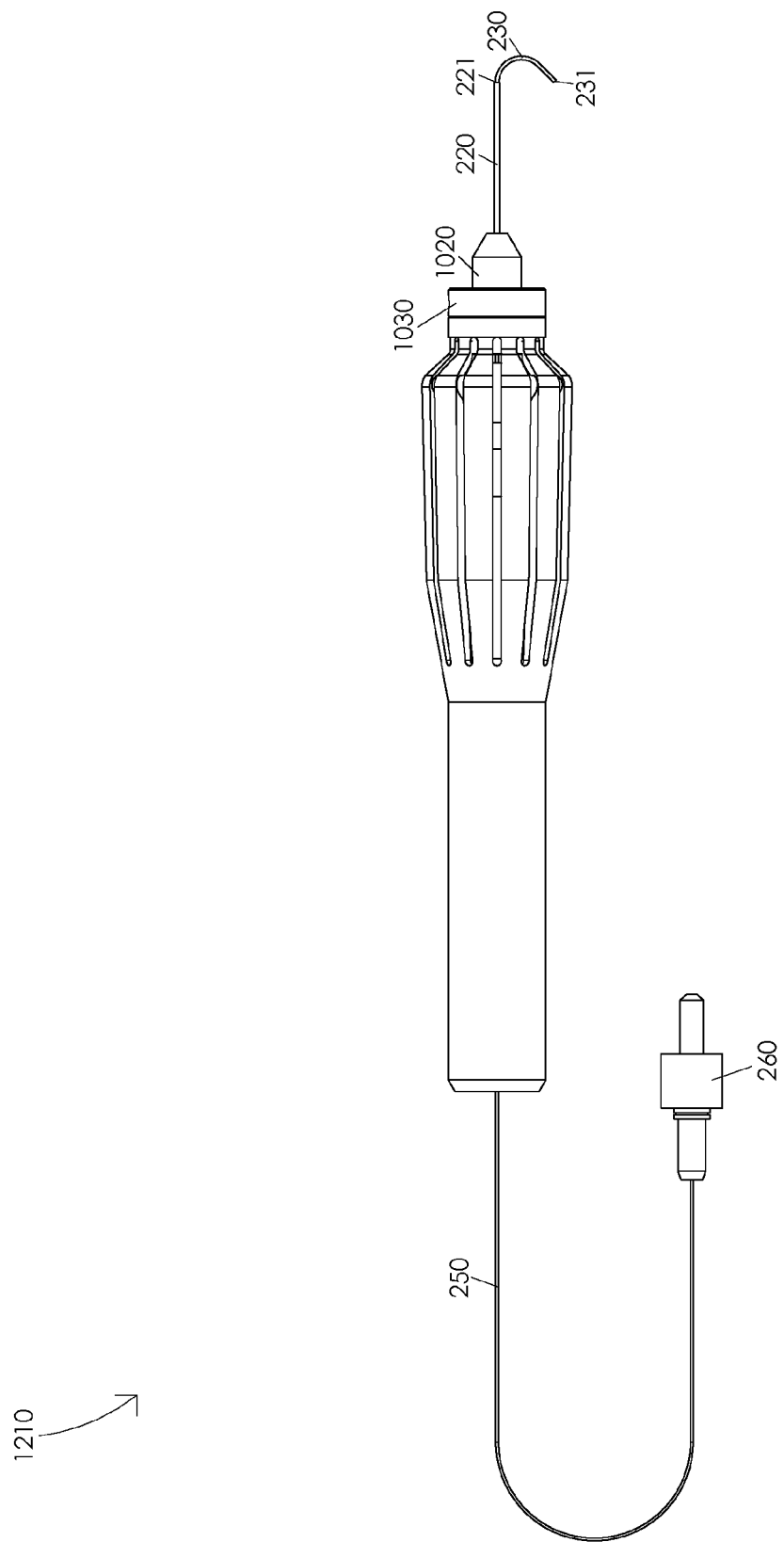

FIG. 12B illustrates an optic fiber in a first partially straightened position 1210. In one or more embodiments, a compression of actuation structure 920 may be configured to gradually straighten optic fiber 250 from a fully curved optic fiber 1200 to an optic fiber in a first partially straightened position 1210. Illustratively, a compression of actuation structure 920 may be configured to gradually extend housing tube 220 relative to wire 240. In one or more embodiments, a gradual extension of housing tube 220 relative to wire 240 may be configured to gradually extend housing tube distal end 221 over a portion of pre-formed curve 245 causing the portion of pre-formed curve 245 to gradually straighten. Illustratively, a gradual straightening of a portion of pre-formed curve 245, e.g., due to a compression of actuation structure 920, may be configured to gradually straighten flexible tube 230. In one or more embodiments, a gradual straightening of flexible tube 230 may be configured to gradually straighten optic fiber 250, e.g., from a fully curved optic fiber 1200 to an optic fiber in a first partially straightened position 1210. Illustratively, a line tangent to optic fiber distal end 251 may intersect a line tangent to housing tube proximal end 202 at a first partially straightened angle, e.g., when optic fiber 250 comprises an optic fiber in a first partially straightened position 1210. Illustratively, the first partially straightened angle may comprise any angle less than 180 degrees. For example, the first partially straightened angle may comprise a 135 degree angle.

Figure 12C:
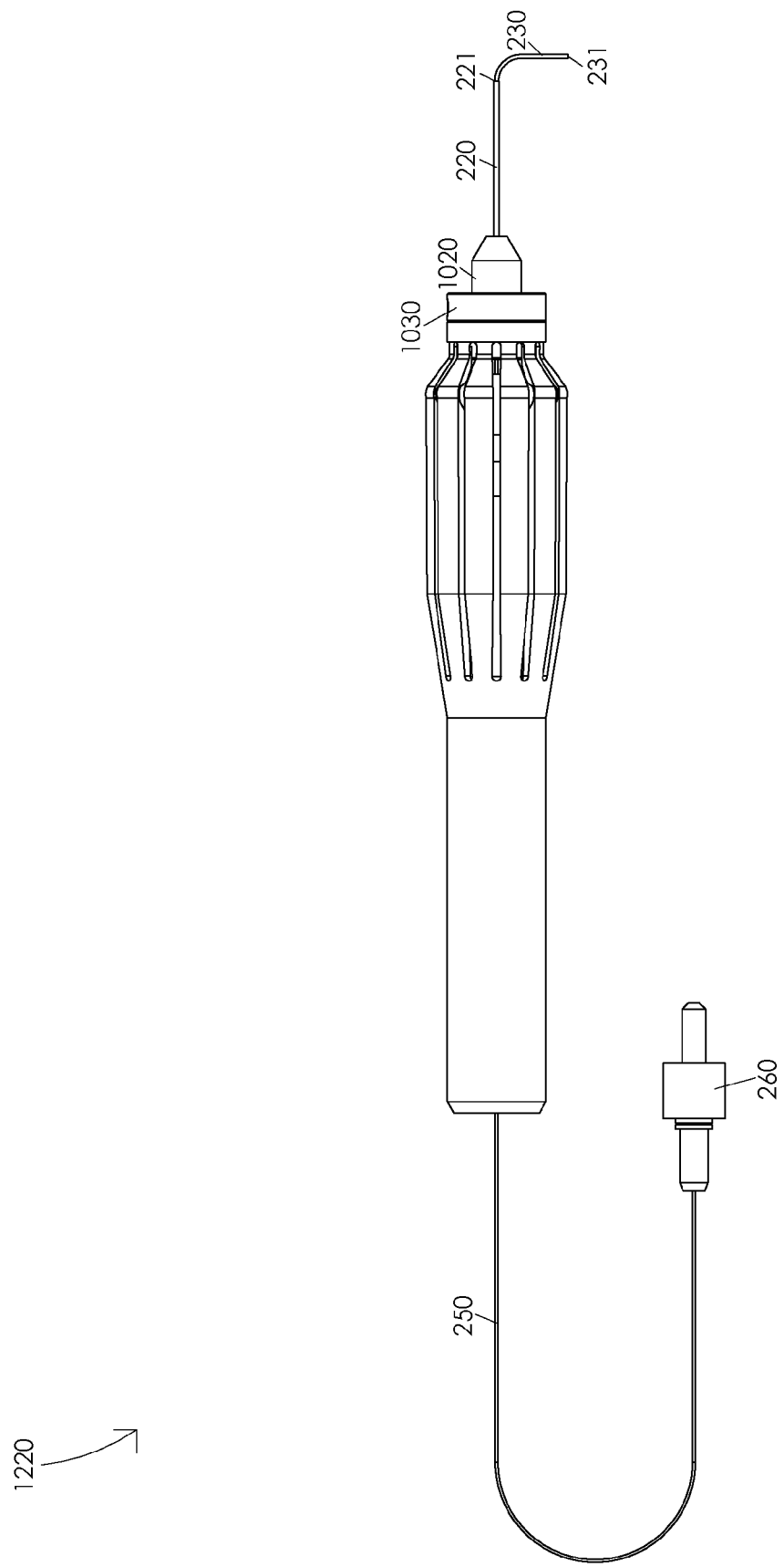

FIG. 12C illustrates an optic fiber in a second partially straightened position 1220. In one or more embodiments, a compression of actuation structure 920 may be configured to gradually straighten optic fiber 250 from an optic fiber in a first partially straightened position 1210 to an optic fiber in a second partially straightened position 1220. Illustratively, a compression of actuation structure 920 may be configured to gradually extend housing tube 220 relative to wire 240. In one or more embodiments, a gradual extension of housing tube 220 relative to wire 240 may be configured to gradually extend housing tube distal end 221 over a portion of pre-formed curve 245 causing the portion of pre-formed curve 245 to gradually straighten. Illustratively, a gradual straightening of a portion of pre-formed curve 245, e.g., due to a compression of actuation structure 920, may be configured to gradually straighten flexible tube 230. In one or more embodiments, a gradual straightening of flexible tube 230 may be configured to gradually straighten optic fiber 250, e.g., from an optic fiber in a first partially straightened position 1210 to an optic fiber in a second partially straightened position 1220. Illustratively, a line tangent to optic fiber distal end 251 may intersect a line tangent to housing tube proximal end 202 at a second partially straightened angle, e.g., when optic fiber 250 comprises an optic fiber in a second partially straightened position 1220. Illustratively, the second partially straightened angle may comprise any angle less than the first partially straightened angle. For example, the second partially straightened angle may comprise a 90 degree angle.

Figure 12D:
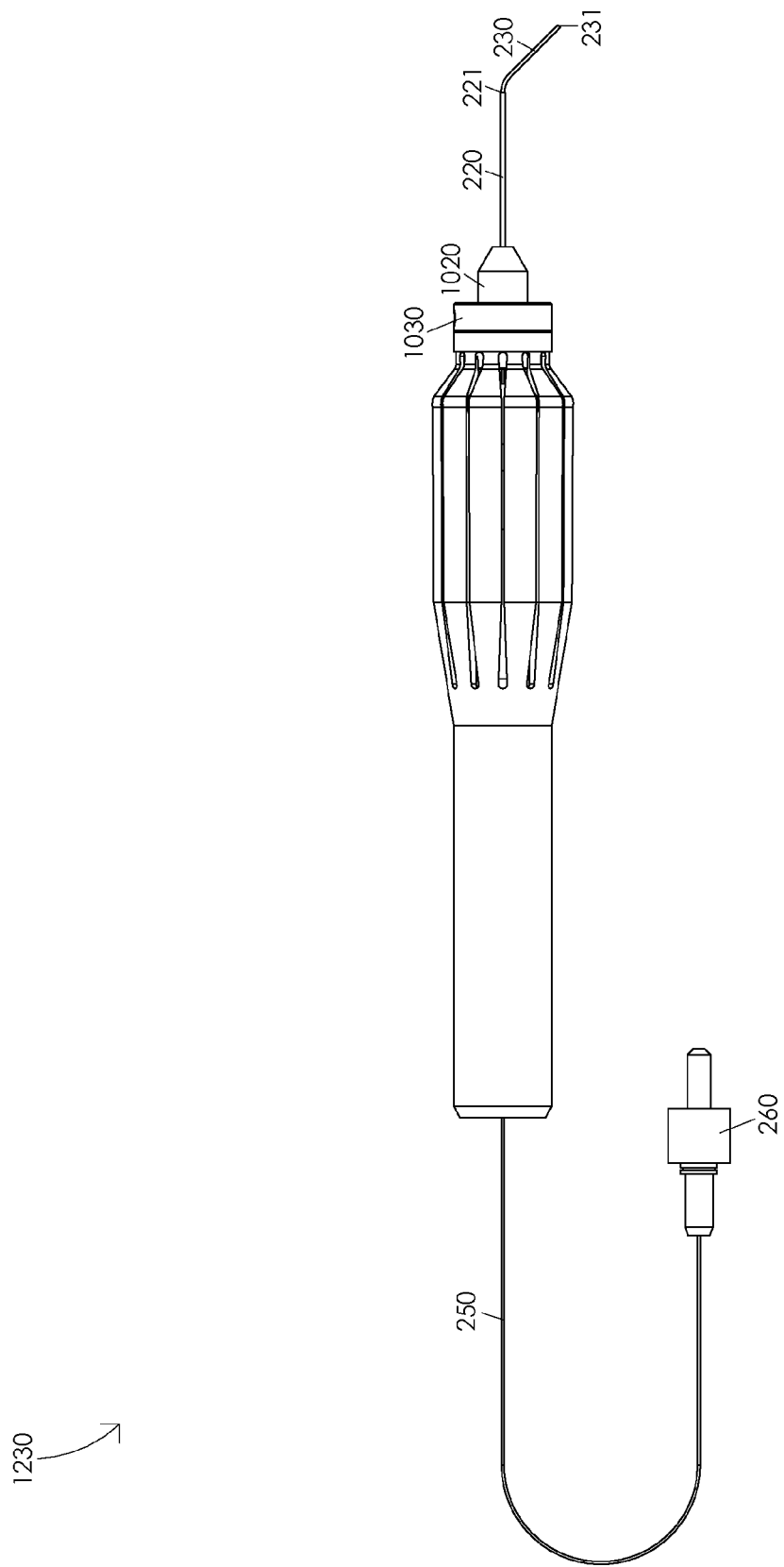

FIG. 12D illustrates an optic fiber in a third partially straightened position 1230. In one or more embodiments, a compression of actuation structure 920 may be configured to gradually straighten optic fiber 250 from an optic fiber in a second partially straightened position 1220 to an optic fiber in a third partially straightened position 1230. Illustratively, a compression of actuation structure 920 may be configured to gradually extend housing tube 220 relative to wire 240. In one or more embodiments, a gradual extension of housing tube 220 relative to wire 240 may be configured to gradually extend housing tube distal end 221 over a portion of pre-formed curve 245 causing the portion of pre-formed curve 245 to gradually straighten. Illustratively, a gradual straightening of a portion of pre-formed curve 245, e.g., due to a compression of actuation structure 920, may be configured to gradually straighten flexible tube 230. In one or more embodiments, a gradual straightening of flexible tube 230 may be configured to gradually straighten optic fiber 250, e.g., from an optic fiber in a second partially straightened position 1220 to an optic fiber in a third partially straightened position 1230. Illustratively, a line tangent to optic fiber distal end 251 may intersect a line tangent to housing tube proximal end 202 at a third partially straightened angle, e.g., when optic fiber 250 comprises an optic fiber in a third partially straightened position 1230. Illustratively, the third partially straightened angle may comprise any angle less than the second partially straightened angle. For example, the third partially straightened angle may comprise a 45 degree angle.

Figure 12E:
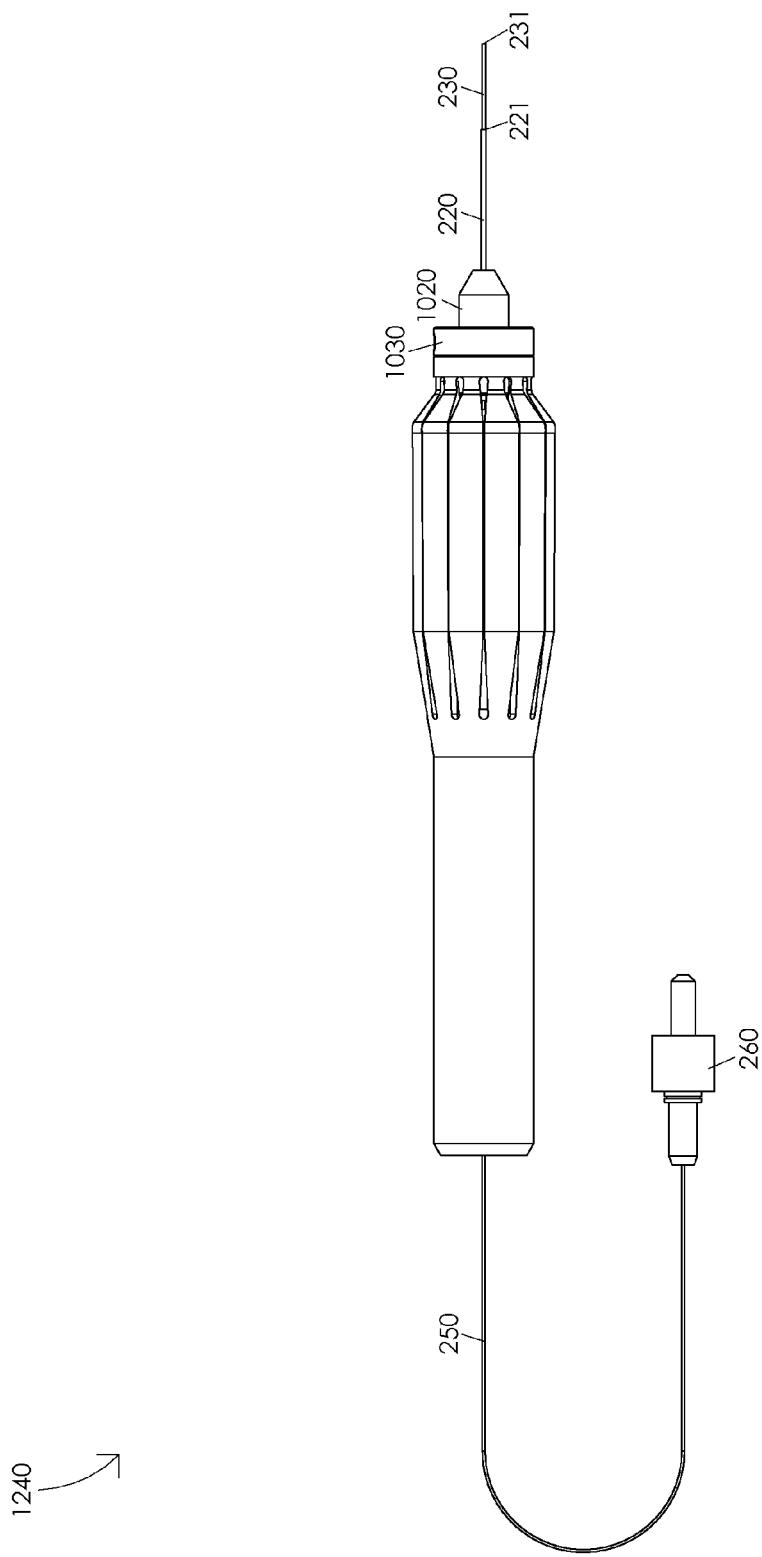

FIG. 12E illustrates an optic fiber in a fully straightened position 1240. In one or more embodiments, a compression of actuation structure 920 may be configured to gradually straighten optic fiber 250 from an optic fiber in a third partially straightened position 1230 to an optic fiber in a fully straightened position 1240. Illustratively, a compression of actuation structure 920 may be configured to gradually extend housing tube 220 relative to wire 240. In one or more embodiments, a gradual extension of housing tube 220 relative to wire 240 may be configured to gradually extend housing tube distal end 221 over a portion of pre-formed curve 245 causing the portion of pre-formed curve 245 to gradually straighten. Illustratively, a gradual straightening of a portion of pre-formed curve 245, e.g., due to a compression of actuation structure 920, may be configured to gradually straighten flexible tube 230. In one or more embodiments, a gradual straightening of flexible tube 230 may be configured to gradually straighten optic fiber 250, e.g., from an optic fiber in a third partially straightened position 1230 to an optic fiber in a fully straightened position 1240. Illustratively, a line tangent to optic fiber distal end 251 may be parallel to a line tangent to housing tube proximal end 202, e.g., when optic fiber 250 comprises an optic fiber in a fully straightened position 1240.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 900 to orient flexible tube 230 in an orientation configured to cause a curvature of flexible tube 230 within the particular transverse plane of the inner eye and varying an amount of decompression of actuation structure 920. Illustratively, a surgeon may aim optic fiber distal end 251 at any target within a particular sagittal plane of the inner eye by, e.g., rotating handle 900 to orient flexible tube 230 in an orientation configured to cause a curvature of flexible tube 230 within the particular sagittal plane of the inner eye and varying an amount of decompression of actuation structure 920. In one or more embodiments, a surgeon may aim optic fiber distal end 251 at any target within a particular frontal plane of the inner eye by, e.g., varying an amount of decompression of actuation structure 920 to orient a line tangent to optic fiber distal end 251 wherein the line tangent to optic fiber distal end 251 is within the particular frontal plane of the inner eye and rotating handle 900. Illustratively, a surgeon may aim optic fiber distal end 251 at any target located outside of the particular transverse plane, the particular sagittal plane, and the particular frontal plane of the inner eye, e.g., by varying a rotational orientation of handle 900 and varying an amount of decompression of actuation structure 920. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. A laser probe comprising:
   a handle having a handle distal end and a handle proximal end;
   an actuation structure of the handle having an actuation structure distal end and an actuation structure proximal end, the actuation structure manufactured from a shape memory material;
   a plurality of actuation arms of the actuation structure, each actuation arm of the plurality of actuation arms having an extension mechanism;
   a handle base of the handle, the handle base having a handle base distal end and a handle base proximal end wherein the handle base distal end is adjacent to the actuation structure proximal end and the handle base proximal end is the handle proximal end;
   an actuation ring of the handle having an actuation ring distal end and an actuation ring proximal end wherein the actuation ring proximal end is adjacent to the actuation structure distal end and the actuation ring distal end is the handle distal end;
   a housing tube platform of the handle;
   a platform base of the handle;
   an actuation mechanism guide of the platform base;
   an actuation mechanism housing of the actuation ring wherein the actuation mechanism housing houses an actuation mechanism that is disposed in the actuation mechanism housing and wherein the actuation mechanism is configured to actuate relative to the handle base within the actuation mechanism guide;

a wire proximal end housing of the handle, the wire proximal end housing disposed within the actuation structure;

a housing tube having a housing tube distal end and a housing tube proximal end, the housing tube proximal end disposed in the housing tube platform wherein a portion of the housing tube is fixed in the housing tube platform;

a flexible tube having a flexible tube distal end and a flexible tube proximal end, the flexible tube disposed in the housing tube wherein the flexible tube distal end extends from the housing tube distal end;

a wire having a wire distal end and a wire proximal end, the wire disposed in the housing tube, the flexible tube, and the wire proximal end housing;

a pre-formed curve of the wire; and an optic fiber having an optic fiber distal end and an optic fiber proximal end, the optic fiber disposed in the flexible tube wherein the optic fiber distal end is adjacent to the flexible tube distal end.

2. The laser probe of claim 1 wherein an application of a compressive force to a particular actuation arm of the plurality of actuation arms is configured to actuate the particular actuation arm.

3. The laser probe of claim 2 wherein the application of the compressive force to the particular actuation arm is configured to actuate every actuation arm of the plurality of actuation arms.

4. The laser probe of claim 3 wherein the application of the compressive force to the particular actuation arm is configured to extend the extension mechanism of the particular actuation arm.

5. The laser probe of claim 4 wherein the application of the compressive force to the particular actuation arm is configured to extend the actuation ring relative to the handle base.

6. The laser probe of claim 1 further comprising:
an inner bore of the handle.

7. The laser probe of claim 1 further comprising:
an inner bore proximal taper of the handle.

8. The laser probe of claim 1 further comprising:
an inner bore distal chamber of the handle.

9. The laser probe of claim 1 further comprising:
an optic fiber guide of the handle.

10. The laser probe of claim 1 further comprising:
a wire guide of the handle.

11. The laser probe of claim 1 further comprising:
a light source interface.

12. The laser probe of claim 1 wherein the wire is manufactured from nitinol.

13. The laser probe of claim 1 wherein a compression of the actuation structure is configured to actuate the actuation ring away from the handle proximal end.

14. The laser probe of claim 13 wherein the compression of the actuation structure is configured to actuate the actuation ring towards the housing tube platform.

15. The laser probe of claim 13 wherein the compression of the actuation structure is configured to extend the actuation mechanism relative to the handle base.

16. The laser probe of claim 13 wherein the compression of the actuation structure is configured to extend the wire relative to the housing tube.

17. The laser probe of claim 13 wherein the compression of the actuation structure is configured to extend the pre-formed curve into a portion of the flexible tube.

18. The laser probe of claim 13 wherein the compression of the actuation structure is configured to curve the flexible tube.

19. The laser probe of claim 13 wherein the compression of the actuation structure is configured to curve the optic fiber.

20. The laser probe of claim 19 wherein the compression of the actuation structure is configured to curve the optic fiber at least 45 degrees.

* * * * *